(12) United States Patent
Nguyen et al.

(10) Patent No.: US 10,983,946 B2
(45) Date of Patent: *Apr. 20, 2021

(54) SCALABLE COMMUNICATION SYSTEM

(71) Applicant: CareFusion 303, Inc., San Diego, CA (US)

(72) Inventors: Ryan Nguyen, San Diego, CA (US); Nick Trung Nguyen, San Marcos, CA (US); Richard Warren Massey, Carlsbad, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/512,239

(22) Filed: Jul. 15, 2019

(65) Prior Publication Data

US 2019/0340151 A1    Nov. 7, 2019

Related U.S. Application Data

(63) Continuation of application No. 13/421,776, filed on Mar. 15, 2012, now Pat. No. 10,353,856.

(Continued)

(51) Int. Cl.
   *G06F 15/16* (2006.01)
   *H04L 12/58* (2006.01)
   (Continued)

(52) U.S. Cl.
   CPC ............. *G06F 15/16* (2013.01); *G06Q 10/10* (2013.01); *G16H 80/00* (2018.01); *H04L 51/36* (2013.01); *H04L 12/184* (2013.01)

(58) Field of Classification Search
   CPC ............................. H04L 1/00; H04L 2201/00
   (Continued)

(56) References Cited

U.S. PATENT DOCUMENTS 2,141,006 A    12/1938  Marinsky
3,724,455 A     4/1973  Unger
(Continued)

FOREIGN PATENT DOCUMENTS

CA    2472098 A1    7/2003
CA    2554903 A1    4/2005
(Continued)

OTHER PUBLICATIONS

U.S. Appl. No. 90/009,912, filed Aug. 12, 2013, Schlotterbeck et al.
(Continued)

*Primary Examiner* — Karen C Tang
(74) *Attorney, Agent, or Firm* — Morgan, Lewis & Bockius LLP

(57) ABSTRACT

A centralized communication system (CCS) is disclosed that provides a modular, extendible, and scalable communication system that can exchange information between any information systems or networked devices. Information from a single source device or system can be selectively broadcast to one or more predetermined destination devices and systems rather than broadcast to every device on the network. Information may be filtered and processed at one or more selectable points in the communication flow between systems. In certain embodiments, an incoming message is received from the source device in the native message format using the native protocol of the source device and converted to an internal messaging format for internal handling within the CCS, then converted to the native message format of a receiving system and sent to the receiving system using its native protocol. In certain embodiments, a graphical representation of the topology of the CCS may be provided.

24 Claims, 26 Drawing Sheets

Related U.S. Application Data

(60) Provisional application No. 61/555,820, filed on Nov. 4, 2011, provisional application No. 61/453,853, filed on Mar. 17, 2011.

(51) Int. Cl.
*G06Q 10/10* (2012.01)
*G16H 80/00* (2018.01)
*G06F 15/173* (2006.01)
*H04L 12/18* (2006.01)

(58) Field of Classification Search
USPC .................................................. 709/217, 231
See application file for complete search history.

(56) References Cited

U.S. PATENT DOCUMENTS

| | | |
|---|---|---|
| 3,831,006 A | 8/1974 | Chaffin, III et al. |
| 3,848,112 A | 11/1974 | Weichselbaum et al. |
| 3,872,448 A | 3/1975 | Mitchell, Jr. |
| 3,898,984 A | 8/1975 | Mandel et al. |
| 3,910,260 A | 10/1975 | Sarnoff et al. |
| 3,921,196 A | 11/1975 | Patterson |
| 3,970,996 A | 7/1976 | Yasaka et al. |
| 4,051,522 A | 9/1977 | Healy et al. |
| 4,135,241 A | 1/1979 | Stanis et al. |
| 4,164,320 A | 8/1979 | Irazoqui et al. |
| 4,216,462 A | 8/1980 | McGrath et al. |
| 4,237,344 A | 12/1980 | Moore |
| 4,315,309 A | 2/1982 | Coli |
| 4,321,461 A | 3/1982 | Walter, Jr. et al. |
| 4,360,125 A | 11/1982 | Martindale et al. |
| 4,373,527 A | 2/1983 | Fischell |
| 4,476,381 A | 10/1984 | Rubin |
| 4,604,847 A | 8/1986 | Moulding, Jr. et al. |
| 4,636,950 A | 1/1987 | Caswell et al. |
| 4,674,652 A | 6/1987 | Aten et al. |
| 4,676,776 A | 6/1987 | Howson |
| 4,688,026 A | 8/1987 | Scribner et al. |
| 4,695,954 A | 9/1987 | Rose et al. |
| 4,696,671 A | 9/1987 | Epstein et al. |
| 4,731,726 A | 3/1988 | Allen |
| 4,733,364 A | 3/1988 | Yamagata |
| 4,741,732 A | 5/1988 | Crankshaw et al. |
| 4,756,706 A | 7/1988 | Kerns et al. |
| 4,778,449 A | 10/1988 | Weber et al. |
| 4,785,969 A | 11/1988 | McLaughlin |
| 4,803,625 A | 2/1989 | Fu et al. |
| 4,810,243 A | 3/1989 | Howson |
| 4,828,545 A | 5/1989 | Epstein et al. |
| 4,831,562 A | 5/1989 | McIntosh et al. |
| 4,835,372 A | 5/1989 | Gombrich et al. |
| 4,839,806 A | 6/1989 | Goldfischer et al. |
| 4,847,764 A | 7/1989 | Halvorson |
| 4,850,009 A | 7/1989 | Zook et al. |
| 4,853,521 A | 8/1989 | Claeys et al. |
| 4,855,909 A | 8/1989 | Vincent et al. |
| 4,857,713 A | 8/1989 | Brown |
| 4,857,716 A | 8/1989 | Gombrich et al. |
| 4,865,584 A | 9/1989 | Epstein et al. |
| 4,882,575 A | 11/1989 | Kawahara |
| 4,899,839 A | 2/1990 | Dessertine et al. |
| 4,916,441 A | 4/1990 | Gombrich et al. |
| 4,918,604 A | 4/1990 | Baum |
| 4,925,444 A | 5/1990 | Orkin et al. |
| 4,942,544 A | 7/1990 | McIntosh et al. |
| 4,950,246 A | 8/1990 | Muller |
| 4,967,928 A | 11/1990 | Carter |
| 4,970,669 A | 11/1990 | McIntosh et al. |
| 4,978,335 A | 12/1990 | Arthur, III |
| 5,001,630 A | 3/1991 | Wiltfong |
| 5,006,699 A | 4/1991 | Felkener et al. |
| 5,036,462 A | 7/1991 | Kaufman et al. |
| 5,036,852 A | 8/1991 | Leishman |
| 5,041,086 A | 8/1991 | Koenig et al. |
| 5,072,383 A | 12/1991 | Brimm et al. |
| 5,077,666 A | 12/1991 | Brimm et al. |
| 5,078,683 A | 1/1992 | Sancoff et al. |
| 5,088,056 A | 2/1992 | McIntosh et al. |
| 5,088,981 A | 2/1992 | Howson et al. |
| 5,100,380 A | 3/1992 | Epstein et al. |
| 5,126,957 A | 6/1992 | Kaufman et al. |
| 5,142,484 A | 8/1992 | Kaufman et al. |
| 5,153,416 A | 10/1992 | Neeley |
| 5,153,827 A | 10/1992 | Coutre et al. |
| 5,164,575 A | 11/1992 | Neeley et al. |
| 5,166,498 A | 11/1992 | Neeley |
| 5,171,977 A | 12/1992 | Morrison |
| 5,181,910 A | 1/1993 | Scanlon |
| 5,190,522 A | 3/1993 | Wojcicki et al. |
| 5,207,642 A | 5/1993 | Orkin et al. |
| 5,235,507 A | 8/1993 | Sackler et al. |
| 5,256,157 A | 10/1993 | Samiotes et al. |
| 5,258,906 A | 11/1993 | Kroll et al. |
| 5,265,010 A | 11/1993 | Evans-Paganelli et al. |
| 5,267,174 A | 11/1993 | Kaufman et al. |
| 5,291,399 A | 3/1994 | Chaco |
| 5,292,029 A | 3/1994 | Pearson |
| 5,307,263 A | 4/1994 | Brown |
| 5,312,334 A | 5/1994 | Hara et al. |
| 5,314,243 A | 5/1994 | McDonald et al. |
| 5,315,505 A | 5/1994 | Pratt et al. |
| 5,317,506 A | 5/1994 | Coutre et al. |
| H1324 H | 6/1994 | Dalke et all. |
| 5,331,547 A | 7/1994 | Laszlo |
| 5,356,378 A | 10/1994 | Doan |
| 5,367,555 A | 11/1994 | Isoyama |
| 5,368,554 A | 11/1994 | Nazarian et al. |
| 5,371,692 A | 12/1994 | Draeger et al. |
| 5,374,813 A | 12/1994 | Shipp |
| 5,376,070 A | 12/1994 | Purvis et al. |
| 5,378,231 A | 1/1995 | Johnson et al. |
| 5,382,232 A | 1/1995 | Hague et al. |
| 5,390,238 A | 2/1995 | Kirk |
| 5,401,059 A | 3/1995 | Ferrario |
| 5,404,384 A | 4/1995 | Colburn et al. |
| 5,408,443 A | 4/1995 | Weinberger |
| 5,412,372 A | 5/1995 | Parkhurst et al. |
| 5,412,564 A | 5/1995 | Ecer |
| 5,416,695 A | 5/1995 | Stutman et al. |
| 5,456,691 A | 10/1995 | Snell |
| 5,460,605 A | 10/1995 | Tuttle et al. |
| 5,465,082 A | 11/1995 | Chaco |
| 5,472,614 A | 12/1995 | Rossi |
| 5,502,944 A | 4/1996 | Kraft et al. |
| 5,515,426 A | 5/1996 | Yacenda et al. |
| 5,522,798 A | 6/1996 | Johnson et al. |
| 5,533,079 A | 7/1996 | Colburn et al. |
| 5,536,084 A | 7/1996 | Curtis et al. |
| 5,538,006 A | 7/1996 | Heim et al. |
| 5,542,420 A | 8/1996 | Goldman et al. |
| 5,544,649 A | 8/1996 | David et al. |
| 5,544,661 A | 8/1996 | Davis et al. |
| 5,547,470 A | 8/1996 | Johnson et al. |
| 5,561,412 A | 10/1996 | Novak et al. |
| 5,562,232 A | 10/1996 | Pearson |
| 5,564,803 A | 10/1996 | McDonald et al. |
| 5,573,506 A | 11/1996 | Vasko |
| 5,582,593 A | 12/1996 | Hultman |
| 5,583,758 A | 12/1996 | McIlroy et al. |
| 5,592,374 A | 1/1997 | Fellagara et al. |
| 5,594,786 A | 1/1997 | Chaco |
| 5,597,995 A | 1/1997 | Williams et al. |
| 5,601,445 A | 2/1997 | Schipper et al. |
| 5,622,429 A | 4/1997 | Heinz |
| 5,628,309 A | 5/1997 | Brown |
| 5,630,710 A | 5/1997 | Tune et al. |
| 5,633,910 A | 5/1997 | Cohen |
| 5,643,212 A | 7/1997 | Coutre et al. |
| 5,644,778 A | 7/1997 | Burks et al. |
| 5,645,531 A | 7/1997 | Thompson et al. |
| 5,651,775 A | 7/1997 | Walker et al. |
| 5,655,118 A | 8/1997 | Hendel et al. |

(56) References Cited

U.S. PATENT DOCUMENTS

| | | |
|---|---|---|
| 5,657,236 A | 8/1997 | Conkright |
| 5,658,250 A | 8/1997 | Blomquist et al. |
| 5,672,154 A | 9/1997 | Sillen et al. |
| 5,681,285 A | 10/1997 | Ford et al. |
| 5,683,367 A | 11/1997 | Jordan et al. |
| 5,685,844 A | 11/1997 | Marttila |
| 5,689,229 A | 11/1997 | Chaco et al. |
| 5,692,640 A | 12/1997 | Caulfield et al. |
| 5,699,038 A | 12/1997 | Ulrich et al. |
| 5,700,998 A | 12/1997 | Palti |
| 5,703,786 A | 12/1997 | Conkright |
| 5,704,352 A | 1/1998 | Tremblay et al. |
| 5,710,551 A | 1/1998 | Ridgeway |
| 5,712,913 A | 1/1998 | Chaum |
| 5,713,856 A | 2/1998 | Eggers |
| 5,721,913 A | 2/1998 | Ackroff et al. |
| 5,733,259 A | 3/1998 | Valcke et al. |
| 5,737,539 A | 4/1998 | Edelson |
| 5,738,102 A | 4/1998 | Lemelson |
| 5,752,235 A | 5/1998 | Kehr et al. |
| 5,758,095 A | 5/1998 | Albaum et al. |
| 5,758,096 A | 5/1998 | Barsky et al. |
| 5,760,704 A | 6/1998 | Barton et al. |
| 5,764,034 A | 6/1998 | Bowman et al. |
| 5,772,585 A | 6/1998 | Lavin et al. |
| 5,774,865 A | 6/1998 | Glynn |
| 5,781,442 A | 7/1998 | Engelson et al. |
| 5,790,409 A | 8/1998 | Fedor et al. |
| 5,795,327 A | 8/1998 | Wilson et al. |
| 5,803,906 A | 9/1998 | Pratt et al. |
| 5,807,321 A | 9/1998 | Stoker et al. |
| 5,807,336 A | 9/1998 | Russo et al. |
| 5,819,229 A | 10/1998 | Boppe |
| 5,822,418 A | 10/1998 | Yacenda et al. |
| 5,822,544 A | 10/1998 | Chaco et al. |
| 5,832,488 A | 11/1998 | Eberhardt |
| 5,833,599 A | 11/1998 | Schrier et al. |
| 5,842,173 A | 11/1998 | Strum et al. |
| 5,842,976 A | 12/1998 | Williamson |
| 5,845,253 A | 12/1998 | Rensimer et al. |
| 5,845,254 A | 12/1998 | Lockwood et al. |
| 5,845,255 A | 12/1998 | Mayaud |
| 5,845,264 A | 12/1998 | Nelhaus |
| 5,848,593 A | 12/1998 | McGrady et al. |
| 5,850,344 A | 12/1998 | Conkright |
| 5,852,408 A | 12/1998 | Christiansen et al. |
| 5,855,550 A | 1/1999 | Lai et al. |
| 5,867,821 A | 2/1999 | Ballantyne et al. |
| 5,871,465 A | 2/1999 | Vasko |
| 5,883,806 A | 3/1999 | Meador et al. |
| 5,885,245 A | 3/1999 | Lynch et al. |
| 5,894,273 A | 4/1999 | Meador et al. |
| 5,895,371 A | 4/1999 | Levitas et al. |
| 5,985,371 A | 4/1999 | Levitas et al. |
| 5,899,998 A | 5/1999 | McGauley et al. |
| 5,903,211 A | 5/1999 | Flego et al. |
| 5,905,653 A | 5/1999 | Higham et al. |
| 5,907,490 A | 5/1999 | Oliver |
| 5,911,132 A | 6/1999 | Sloane |
| 5,911,687 A | 6/1999 | Sato et al. |
| 5,912,818 A | 6/1999 | McGrady |
| 5,920,054 A | 6/1999 | Uber, III |
| 5,920,263 A | 7/1999 | Huttenhoff et al. |
| 5,928,329 A | 7/1999 | Clark et al. |
| 5,930,145 A | 7/1999 | Yuyama et al. |
| 5,935,099 A | 8/1999 | Peterson et al. |
| 5,941,710 A | 8/1999 | Lampotang et al. |
| 5,942,986 A | 8/1999 | Shabot et al. |
| 5,950,630 A | 9/1999 | Portwood et al. |
| 5,950,632 A | 9/1999 | Reber et al. |
| 5,953,099 A | 9/1999 | Walach |
| 5,954,641 A | 9/1999 | Kehr et al. |
| 5,957,885 A | 9/1999 | Bollish et al. |
| 5,961,036 A | 10/1999 | Michael et al. |
| 5,961,446 A | 10/1999 | Beller et al. |
| 5,971,593 A | 10/1999 | McGrady |
| 5,995,077 A | 11/1999 | Wilcox et al. |
| 6,000,828 A | 12/1999 | Leet |
| 6,003,006 A | 12/1999 | Colella |
| 6,009,333 A | 12/1999 | Chaco |
| 6,017,318 A | 1/2000 | Gauthier et al. |
| 6,021,392 A | 2/2000 | Lester et al. |
| 6,024,699 A | 2/2000 | Surwit et al. |
| 6,032,155 A | 2/2000 | de la Huerga |
| 6,039,251 A | 3/2000 | Holowko et al. |
| 6,047,203 A | 4/2000 | Sackner et al. |
| 6,048,087 A | 4/2000 | Laurent et al. |
| 6,053,887 A | 4/2000 | Levitas et al. |
| 6,063,026 A | 5/2000 | Schauss et al. |
| 6,082,776 A | 7/2000 | Feinberg |
| 6,112,182 A | 8/2000 | Akers et al. |
| RE36,871 E | 9/2000 | Epstein et al. |
| 6,112,502 A | 9/2000 | Frederick et al. |
| 6,134,582 A | 10/2000 | Kennedy |
| 6,135,949 A | 10/2000 | Russo et al. |
| 6,202,923 B1 | 3/2001 | Boyer et al. |
| 6,228,057 B1 | 5/2001 | Vasko |
| 6,241,704 B1 | 6/2001 | Peterson et al. |
| 6,269,340 B1 | 7/2001 | Ford et al. |
| 6,282,441 B1 | 8/2001 | Raymond et al. |
| 6,290,681 B1 | 9/2001 | Brown |
| 6,292,698 B1 | 9/2001 | Duffin et al. |
| 6,302,844 B1 | 10/2001 | Walker et al. |
| 6,312,378 B1 | 11/2001 | Bardy |
| 6,314,556 B1 | 11/2001 | DeBusk et al. |
| 6,319,200 B1 | 11/2001 | Lai et al. |
| 6,322,502 B1 | 11/2001 | Schoenberg et al. |
| 6,338,007 B1 | 1/2002 | Broadfield et al. |
| 6,339,732 B1 | 1/2002 | Phoon et al. |
| 6,406,426 B1 | 6/2002 | Reuss et al. |
| 6,409,684 B1 | 6/2002 | Wilk |
| 6,421,650 B1 | 7/2002 | Goetz et al. |
| 6,493,747 B2 | 12/2002 | Simmon et al. |
| 6,519,569 B1 | 2/2003 | White et al. |
| 6,529,892 B1 | 3/2003 | Lambert |
| 6,540,672 B1 | 4/2003 | Simonsen et al. |
| 6,558,352 B1 | 5/2003 | Hogan |
| 6,571,128 B2 | 5/2003 | Lebel et al. |
| 6,581,606 B2 | 6/2003 | Kutzko et al. |
| 6,671,563 B1 | 12/2003 | Engelson et al. |
| 6,745,764 B2 | 6/2004 | Hickle |
| 6,757,898 B1 | 7/2004 | Ilsen et al. |
| 6,785,589 B2 | 8/2004 | Eggenberger et al. |
| 6,796,956 B2 | 9/2004 | Hartlaub et al. |
| 6,799,149 B2 | 9/2004 | Hartlaub |
| 6,847,861 B2 | 1/2005 | Lunak et al. |
| 6,856,247 B1 | 2/2005 | Wallace |
| 6,873,268 B2 | 3/2005 | Lebel et al. |
| 6,993,402 B2 | 1/2006 | Klass et al. |
| 7,034,691 B1 | 4/2006 | Rapaport et al. |
| 7,054,844 B2 | 5/2006 | Fletcher et al. |
| 7,060,059 B2 | 6/2006 | Keith et al. |
| 7,096,072 B2 | 8/2006 | Engleson et al. |
| 7,201,734 B2 | 4/2007 | Hickle |
| 7,204,823 B2 | 4/2007 | Estes et al. |
| 7,215,991 B2 | 5/2007 | Besson et al. |
| 7,229,430 B2 | 6/2007 | Hickle et al. |
| 7,230,529 B2 | 6/2007 | Ketcherside, Jr. et al. |
| 7,256,708 B2 | 8/2007 | Rosenfeld et al. |
| 7,263,492 B1 | 8/2007 | Suresh et al. |
| 7,379,885 B1 | 5/2008 | Zakim |
| 7,384,420 B2 | 6/2008 | Dycus et al. |
| 7,398,183 B2 | 7/2008 | Holland et al. |
| 7,421,709 B2 | 9/2008 | Watson et al. |
| 7,433,853 B2 | 10/2008 | Brockway et al. |
| 7,471,994 B2 | 12/2008 | Ford et al. |
| 7,526,769 B2 | 4/2009 | Watts et al. |
| 7,587,415 B2 | 9/2009 | Gaurav et al. |
| 7,612,679 B1 | 11/2009 | Fackler et al. |
| 7,693,697 B2 | 4/2010 | Westenskow et al. |
| 7,769,601 B1 | 8/2010 | Bleser et al. |
| 7,771,385 B2 | 8/2010 | Eggers et al. |
| 7,771,386 B2 | 8/2010 | Eggers et al. |
| 7,776,031 B2 | 8/2010 | Hartlaub et al. |

(56) References Cited

U.S. PATENT DOCUMENTS

| | | |
|---|---|---|
| 7,787,946 B2 | 8/2010 | Stahmann et al. |
| 7,796,045 B2 | 9/2010 | Spear et al. |
| 7,835,927 B2 | 11/2010 | Schlotterbeck et al. |
| 7,847,970 B1 | 12/2010 | McGrady |
| 7,860,583 B2 | 12/2010 | Condurso et al. |
| 7,935,927 B2 | 5/2011 | Miyamoto et al. |
| 7,962,544 B2 | 6/2011 | Torok et al. |
| 7,970,550 B2 | 6/2011 | Arakelyan et al. |
| 7,983,995 B2 | 7/2011 | Murphy et al. |
| 8,005,688 B2 | 8/2011 | Coffman et al. |
| 8,024,200 B2 | 9/2011 | Jennings et al. |
| 8,160,895 B2 | 4/2012 | Schmitt et al. |
| 8,197,437 B2 | 6/2012 | Kalafut et al. |
| 8,284,059 B2 | 10/2012 | Ross |
| 8,291,337 B2 | 10/2012 | Gannin et al. |
| 8,340,792 B2 | 12/2012 | Condurso et al. |
| 8,630,722 B2 | 1/2014 | Condurso |
| 8,689,008 B2 | 4/2014 | Rangadass |
| 8,863,156 B1 * | 10/2014 | Lepanto ............ G06F 9/44521 719/328 |
| 2001/0037083 A1 | 11/2001 | Hartlaub et al. |
| 2001/0044731 A1 | 11/2001 | Coffman et al. |
| 2002/0010679 A1 | 1/2002 | Felsher |
| 2002/0016568 A1 | 2/2002 | Lebel et al. |
| 2002/0016923 A1 | 2/2002 | Knaus et al. |
| 2002/0022973 A1 | 2/2002 | Sun et al. |
| 2002/0026223 A1 | 2/2002 | Riff et al. |
| 2002/0033548 A1 | 3/2002 | Brodkin et al. |
| 2002/0035484 A1 | 3/2002 | McCormick |
| 2002/0038392 A1 | 3/2002 | De La Huerga |
| 2002/0042636 A1 | 4/2002 | Koshiol et al. |
| 2002/0046346 A1 | 4/2002 | Evans |
| 2002/0077849 A1 | 6/2002 | Baruch et al. |
| 2002/0087114 A1 | 7/2002 | Hartlaub |
| 2002/0116509 A1 | 8/2002 | De La Huerga |
| 2002/0120350 A1 | 8/2002 | Klass et al. |
| 2002/0169636 A1 | 11/2002 | Eggers et al. |
| 2002/0198624 A1 | 12/2002 | Greenwald et al. |
| 2003/0009244 A1 | 1/2003 | Engleson et al. |
| 2003/0036683 A1 | 2/2003 | Kehr et al. |
| 2003/0045858 A1 | 3/2003 | Struys et al. |
| 2003/0051737 A1 | 3/2003 | Hickle et al. |
| 2003/0063524 A1 | 4/2003 | Niemiec et al. |
| 2003/0069481 A1 | 4/2003 | Hervy et al. |
| 2003/0105389 A1 | 6/2003 | Noonan et al. |
| 2003/0105555 A1 | 6/2003 | Lunak et al. |
| 2003/0106553 A1 | 6/2003 | Vanderveen |
| 2003/0114836 A1 | 6/2003 | Estes et al. |
| 2003/0121517 A1 | 7/2003 | McFarland |
| 2003/0129578 A1 | 7/2003 | Mault |
| 2003/0135087 A1 | 7/2003 | Hickle et al. |
| 2003/0135388 A1 | 7/2003 | Martucci et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0149599 A1 | 8/2003 | Goodall et al. |
| 2003/0156143 A1 | 8/2003 | Westenskow et al. |
| 2003/0158746 A1 | 8/2003 | Forrester |
| 2003/0163223 A1 | 8/2003 | Blomquist |
| 2003/0205897 A1 | 11/2003 | Kaufman |
| 2003/0236683 A1 | 12/2003 | Henderson et al. |
| 2004/0015858 A1 * | 1/2004 | Seto ................ G06F 9/449 717/120 |
| 2004/0068229 A1 | 4/2004 | Jansen et al. |
| 2004/0073329 A1 | 4/2004 | Engleson et al. |
| 2004/0107118 A1 | 6/2004 | Harnsberger |
| 2004/0122702 A1 | 6/2004 | Sabol |
| 2004/0122705 A1 | 6/2004 | Sabol |
| 2004/0122719 A1 | 6/2004 | Sabol |
| 2004/0122790 A1 | 6/2004 | Walker |
| 2004/0128162 A1 | 7/2004 | Schlotterbeck et al. |
| 2004/0152622 A1 | 8/2004 | Keith et al. |
| 2004/0167465 A1 | 8/2004 | Mihai et al. |
| 2004/0167804 A1 | 8/2004 | Simpson et al. |
| 2004/0172283 A1 | 9/2004 | Vanderveen et al. |
| 2004/0172300 A1 | 9/2004 | Mihai et al. |
| 2004/0172302 A1 | 9/2004 | Martucci et al. |
| 2004/0176297 A1 | 9/2004 | Cheung et al. |
| 2004/0188998 A1 | 9/2004 | Henthorn |
| 2004/0193325 A1 | 9/2004 | Bonderud et al. |
| 2004/0193446 A1 | 9/2004 | Mayer et al. |
| 2004/0260478 A1 | 12/2004 | Schwamm |
| 2005/0010166 A1 | 1/2005 | Hickle |
| 2005/0010269 A1 | 1/2005 | Lebel et al. |
| 2005/0020996 A1 | 1/2005 | Hartlaub et al. |
| 2005/0021297 A1 | 1/2005 | Hartlaub |
| 2005/0022274 A1 | 1/2005 | Campbell et al. |
| 2005/0033606 A1 | 2/2005 | Miller |
| 2005/0049179 A1 | 3/2005 | Davidson et al. |
| 2005/0055242 A1 | 3/2005 | Bello et al. |
| 2005/0088296 A1 | 4/2005 | Lee |
| 2005/0096941 A1 | 5/2005 | Tong |
| 2005/0097566 A1 | 5/2005 | Watts et al. |
| 2005/0107914 A1 | 5/2005 | Engleson et al. |
| 2005/0108057 A1 | 5/2005 | Cohen et al. |
| 2005/0113945 A1 | 5/2005 | Engleson et al. |
| 2005/0119788 A1 | 6/2005 | Engleson et al. |
| 2005/0144043 A1 | 6/2005 | Holland et al. |
| 2005/0145010 A1 | 7/2005 | Vanderveen et al. |
| 2005/0148890 A1 | 7/2005 | Hastings |
| 2005/0171815 A1 | 8/2005 | Vanderveen |
| 2005/0224083 A1 | 10/2005 | Crass et al. |
| 2005/0278194 A1 | 12/2005 | Holland et al. |
| 2006/0026205 A1 | 2/2006 | Butterfield |
| 2006/0047538 A1 | 3/2006 | Condurso et al. |
| 2006/0053036 A1 | 3/2006 | Coffman et al. |
| 2006/0079831 A1 | 4/2006 | Gilbert |
| 2006/0101072 A1 | 5/2006 | Busche et al. |
| 2006/0122481 A1 | 6/2006 | Sievenpiper et al. |
| 2006/0190302 A1 | 8/2006 | Eggers et al. |
| 2006/0200369 A1 | 9/2006 | Batch et al. |
| 2006/0206356 A1 | 9/2006 | Vanderveen |
| 2006/0217628 A1 | 9/2006 | Huiku |
| 2006/0218015 A1 | 9/2006 | Walker et al. |
| 2006/0229551 A1 | 10/2006 | Martinez et al. |
| 2006/0249423 A1 | 11/2006 | Reijonen |
| 2006/0262915 A1 * | 11/2006 | Marascio ............ H04Q 11/0414 379/201.01 |
| 2006/0271401 A1 | 11/2006 | Lassetter et al. |
| 2006/0287890 A1 | 12/2006 | Stead et al. |
| 2007/0015972 A1 | 1/2007 | Wang et al. |
| 2007/0043767 A1 | 2/2007 | Osborne et al. |
| 2007/0061266 A1 | 3/2007 | Moore |
| 2007/0061393 A1 | 3/2007 | Moore |
| 2007/0083389 A1 | 4/2007 | Dyer et al. |
| 2007/0106457 A1 | 5/2007 | Rosenberg |
| 2007/0106753 A1 | 5/2007 | Moore |
| 2007/0106754 A1 | 5/2007 | Moore |
| 2007/0129647 A1 | 6/2007 | Lynn |
| 2007/0156452 A1 | 7/2007 | Batch |
| 2007/0156860 A1 | 7/2007 | Nedelcu et al. |
| 2007/0168301 A1 | 7/2007 | Eisner et al. |
| 2007/0185615 A1 | 8/2007 | Bossi et al. |
| 2007/0208454 A1 | 9/2007 | Forrester et al. |
| 2007/0210157 A1 | 9/2007 | Miller |
| 2007/0286466 A1 | 12/2007 | Heffernan |
| 2007/0293843 A1 | 12/2007 | Ireland et al. |
| 2008/0015549 A1 | 1/2008 | Maughan |
| 2008/0025230 A1 | 1/2008 | Patel et al. |
| 2008/0034323 A1 | 2/2008 | Blomquist |
| 2008/0040151 A1 | 2/2008 | Moore |
| 2008/0046292 A1 | 2/2008 | Myers |
| 2008/0141272 A1 | 6/2008 | Borgendale et al. |
| 2008/0162254 A1 | 7/2008 | Herger et al. |
| 2008/0164998 A1 | 7/2008 | Scherpbier et al. |
| 2008/0169045 A1 | 7/2008 | Tribble et al. |
| 2008/0195246 A1 | 8/2008 | Tribble et al. |
| 2008/0272138 A1 | 11/2008 | Ross et al. |
| 2008/0317672 A1 | 12/2008 | Viertio-Oja |
| 2009/0012812 A1 | 1/2009 | Rausch et al. |
| 2009/0012813 A1 | 1/2009 | Berzansky et al. |
| 2009/0043253 A1 | 2/2009 | Podaima |
| 2009/0054754 A1 | 2/2009 | McMahon et al. |
| 2009/0062727 A1 | 3/2009 | Woo |

(56) References Cited

U.S. PATENT DOCUMENTS

| | | |
|---|---|---|
| 2009/0099867 A1 | 4/2009 | Newman |
| 2009/0112333 A1 | 4/2009 | Sahai |
| 2009/0125335 A1 | 5/2009 | Manetta et al. |
| 2009/0150484 A1 | 6/2009 | Roberts |
| 2009/0210252 A1 | 8/2009 | Silver |
| 2009/0240651 A1 | 9/2009 | Fletcher et al. |
| 2009/0270810 A1 | 10/2009 | DeBelser et al. |
| 2009/0306585 A1 | 12/2009 | Pang et al. |
| 2009/0306944 A1 | 12/2009 | Willmann et al. |
| 2009/0319623 A1 | 12/2009 | Srinivasan et al. |
| 2010/0037067 A1 | 2/2010 | Rangadass |
| 2010/0094653 A1 | 4/2010 | Tribble et al. |
| 2010/0121654 A1 | 5/2010 | Portnoy et al. |
| 2010/0161113 A1 | 6/2010 | Tribble et al. |
| 2010/0169120 A1 | 7/2010 | Herbst et al. |
| 2010/0169771 A1 | 7/2010 | Pelegrin et al. |
| 2010/0174552 A1 | 7/2010 | Hawkes et al. |
| 2010/0174553 A1 | 7/2010 | Kaufman et al. |
| 2010/0179825 A1 | 7/2010 | Hanov et al. |
| 2010/0241453 A1 | 9/2010 | Malec |
| 2010/0241456 A1 | 9/2010 | Miller et al. |
| 2010/0271218 A1 | 10/2010 | Hoag et al. |
| 2010/0280840 A1 | 11/2010 | Fukushi et al. |
| 2010/0323397 A1 | 12/2010 | Reavy et al. |
| 2011/0015941 A1 | 1/2011 | Backhaus |
| 2011/0046975 A1 | 2/2011 | Hoffman |
| 2011/0060758 A1 | 3/2011 | Schlotterbeck et al. |
| 2011/0078608 A1 | 3/2011 | Gannon et al. |
| 2011/0119612 A1 | 5/2011 | Gannon et al. |
| 2011/0179405 A1 | 7/2011 | Dicks |
| 2011/0202495 A1 | 8/2011 | Gawlick |
| 2011/0282691 A1 | 11/2011 | Coffman et al. |
| 2011/0288882 A1 | 11/2011 | Halow |
| 2011/0313787 A1 | 12/2011 | Rangadass |
| 2012/0011253 A1 | 1/2012 | Friedman et al. |
| 2012/0016215 A1 | 1/2012 | Condurso et al. |
| 2012/0041775 A1 | 2/2012 | Cosentino et al. |
| 2012/0053533 A1 | 3/2012 | Butterfield et al. |
| 2012/0075061 A1 | 3/2012 | Barnes |
| 2012/0136673 A1 | 5/2012 | Presley et al. |
| 2012/0173264 A1 | 7/2012 | Brush et al. |
| 2012/0179006 A1 | 7/2012 | Jansen et al. |
| 2012/0182939 A1 | 7/2012 | Rajan |
| 2012/0185267 A1 | 7/2012 | Kamen et al. |
| 2012/0191052 A1 | 7/2012 | Rao |
| 2012/0239824 A1 | 9/2012 | Nguyen et al. |
| 2012/0241043 A1 | 9/2012 | Perazzo et al. |
| 2012/0247480 A1 | 10/2012 | Varga |
| 2012/0253835 A1 | 10/2012 | Tracy et al. |
| 2012/0265549 A1 | 10/2012 | Virolainen |
| 2012/0310205 A1 | 12/2012 | Lee et al. |
| 2013/0018356 A1 | 1/2013 | Prince et al. |
| 2013/0085771 A1 | 4/2013 | Ghanbari et al. |
| 2013/0096444 A1 | 4/2013 | Condurso et al. |
| 2013/0197927 A1 | 8/2013 | Vanderveen et al. |
| 2013/0197928 A1 | 8/2013 | Vanderveen et al. |
| 2013/0197929 A1 | 8/2013 | Vanderveen et al. |
| 2013/0197930 A1 | 8/2013 | Garibaldi et al. |
| 2013/0197931 A1 | 8/2013 | Gupta et al. |
| 2013/0204433 A1 | 8/2013 | Gupta et al. |
| 2013/0204637 A1 | 8/2013 | Vanderveen et al. |
| 2013/0262138 A1 | 10/2013 | Jaskela et al. |
| 2014/0028464 A1 | 1/2014 | Garibaldi |
| 2014/0031976 A1 | 1/2014 | Reinhardt et al. |
| 2014/0100868 A1 | 4/2014 | Condurso et al. |
| 2014/0278466 A1 | 9/2014 | Simmons et al. |
| 2014/0297313 A1 | 10/2014 | Condurso et al. |
| 2014/0350950 A1 | 11/2014 | Jaskela et al. |
| 2015/0250948 A1 | 9/2015 | Gupta et al. |
| 2016/0000997 A1 | 1/2016 | Batch et al. |

FOREIGN PATENT DOCUMENTS

| | | |
|---|---|---|
| CN | 1421810 A | 6/2003 |
| CN | 1759398 A | 4/2006 |
| CN | 1803103 A | 7/2006 |
| CN | 101116077 A | 1/2008 |
| CN | 101146055 A | 3/2008 |
| CN | 201110955 Y | 9/2008 |
| CN | 101331491 A | 12/2008 |
| CN | 101689320 A | 3/2010 |
| CN | 101890193 A | 11/2010 |
| CN | 102068725 A | 5/2011 |
| CN | 10 2521394 A | 6/2012 |
| CN | 102508877 A | 6/2012 |
| CN | 102688532 A | 9/2012 |
| CN | 102799783 A | 11/2012 |
| DE | 4023785 | 1/1992 |
| EP | 0192786 | 9/1986 |
| EP | 0384155 | 8/1990 |
| EP | 0595474 | 5/1994 |
| EP | 0649316 | 4/1995 |
| EP | 0652528 | 5/1995 |
| EP | 0784283 | 7/1997 |
| EP | 0921488 | 6/1999 |
| EP | 1003121 | 5/2000 |
| EP | 1018347 | 7/2000 |
| EP | 1237113 | 9/2002 |
| EP | 1750573 A1 | 2/2007 |
| GB | 2141006 | 12/1984 |
| JP | 62114562 | 5/1987 |
| JP | 5168708 | 7/1993 |
| JP | 11-505352 | 5/1999 |
| JP | 2002-520718 | 7/2002 |
| JP | 2003085283 A | 3/2003 |
| JP | 2004287616 A | 10/2004 |
| JP | 2005165442 A | 6/2005 |
| JP | 2005296428 A | 10/2005 |
| JP | 2006155070 A | 6/2006 |
| JP | 2006521183 A | 9/2006 |
| JP | 2008508616 A | 3/2008 |
| JP | 2008516303 A | 5/2008 |
| JP | 2011201311 A | 1/2011 |
| JP | 2012200430 A | 10/2012 |
| KR | 102007004561 | 5/2007 |
| KR | 102008001312 | 2/2008 |
| KR | 100847397 B1 | 7/2008 |
| KR | 102010012597 | 12/2010 |
| KR | 102011007082 | 6/2011 |
| KR | 102012007661 | 7/2012 |
| KR | 102012007663 | 7/2012 |
| NZ | 522631 A | 7/2004 |
| WO | WO1993/022735 | 11/1993 |
| WO | WO1994/005344 | 3/1994 |
| WO | WO1994/008647 | 4/1994 |
| WO | WO1994/013250 | 6/1994 |
| WO | WO1995/023378 | 8/1995 |
| WO | WO1996/020745 | 7/1996 |
| WO | WO-199620745 A1 | 7/1996 |
| WO | WO1996/025214 | 8/1996 |
| WO | WO-199625214 A1 | 8/1996 |
| WO | WO1996/036923 | 11/1996 |
| WO | WO1997/004712 | 2/1997 |
| WO | WO1998/013783 | 4/1998 |
| WO | WO1998/028676 | 7/1998 |
| WO | WO1999/009505 | 2/1999 |
| WO | WO1999/010829 | 3/1999 |
| WO | WO1999/010830 | 3/1999 |
| WO | WO1999/035588 | 7/1999 |
| WO | WO1999/044167 | 9/1999 |
| WO | WO1999/045490 | 9/1999 |
| WO | WO1999/046718 | 9/1999 |
| WO | WO1999/067732 | 12/1999 |
| WO | WO2000/003344 | 1/2000 |
| WO | WO2000/004521 | 1/2000 |
| WO | WO2000/018449 | 4/2000 |
| WO | WO2000/032088 | 6/2000 |
| WO | WO2000/032098 | 6/2000 |
| WO | WO2001/086506 | 11/2001 |
| WO | WO2001/088828 | 11/2001 |
| WO | WO2002/036044 | 5/2002 |
| WO | WO2002/069099 | 9/2002 |
| WO | WO2003/038566 | 5/2003 |
| WO | WO2003/053503 | 7/2003 |

(56) References Cited

FOREIGN PATENT DOCUMENTS

| WO | WO2003/092769 | 11/2003 |
|---|---|---|
| WO | WO2003/094091 | 11/2003 |
| WO | WO2004/060443 | 7/2004 |
| WO | WO2004/061745 | 7/2004 |
| WO | WO-2002053209 A1 | 10/2004 |
| WO | WO-2008087982 A1 | 5/2010 |
| WO | WO-2010124016 A1 | 10/2010 |
| WO | WO-2010124328 A1 | 11/2010 |
| WO | WO-2012095829 A2 | 7/2012 |
| WO | WO-2014159280 A1 | 10/2014 |

OTHER PUBLICATIONS

U.S. Appl. No. 90/011,697, filed Aug. 12, 2013, Schlotterbeck et al.
U.S. Appl. No. 09/860,865, filed May 18, 2001, Damon J. Coffman, et al.
U.S. Appl. No. 10/750,032, filed Dec. 31, 2003, Timothy W. Vanderveen.
U.S. Appl. No. 10/361,704, filed Feb. 9, 2003, Timothy W. Vanderveen, et al.
U.S. Appl. No. 13/185,427, filed Jul. 18, 2011, Damon J. Coffman, et al.
U.S. Appl. No. 13/246,782, filed Sep. 27, 2011, Joseph Condurso, et al.
U.S. Appl. No. 13/559,537, filed Jul. 26, 2012, Federico Garibaldi.
U.S. Appl. No. 13/802,663, filed Mar. 13, 2013, Federico Garibaldi.
U.S. Appl. No. 13/802,443, filed Mar. 13, 2013, Timothy W. Vanderveen, et al.
U.S. Appl. No. 13/802,679, filed Mar. 13, 2013, Vikas Gupta, et al.
U.S. Appl. No. 13/802,683, filed Mar. 13, 2013, Vikas Gupta, et al.
U.S. Appl. No. 13/802,446, filed Mar. 13, 213, Timothy W. Vanderveen, et al.
U.S. Appl. No. 13/802,433, filed Mar. 13, 2013, Timothy W. Vanderveen, et al.
U.S. Appl. No. 13/802,454, filed Mar. 13, 2013, Timothy W. Vanderveen, et al.
U.S. Appl. No. 13/901,504, filed May 23, 2013, Maria Consolacion Jaskela, et al.
Evans, R. S. et al., "Enhanced notification of infusion pump programming errors", Studies in health technology and informatics, Jan. 1, 2010, pp. 734-738, XP055305644, Netherlands DOI: 10.3233/978-1-60750-588-4-734 Retrieved from the Internet: URL:http://booksonline.iospress.nl/Extern/EnterMedLine.aspx?ISSN=0926-9630&Volume=160&SPage=734 [retrieved on Sep. 26, 2016].
Extended European Search Report and Written Opinion for Application No. 14772937.0, dated Oct. 10, 2016, 9 pages.
Extended European Search Report and Written Opinion for Application No. 14779139.6, dated Nov. 7, 2016, 7 pages.
"'Smart' Infusion Pumps Join CPOE and Bar Coding as Important Ways to Prevent Medication Errors," ISMP—Medication Safety Alert, Feb. 7, 2002, 2 pgs., Institute for Safe Medication Practices.
"General-Purpose Infusion Pumps," Evaluation—Health Devices, Oct. 2002, pp. 353-387, vol. 31(10), ECRI Institute.
"Infusion Pump Technology," Health Devices, Apr.-May 1998, pp. 150-170, vol. 27(4-5), ECRI Institute.
"Infusion Pumps, General-Purpose," Healthcare Product Comparison System, 2007, pp. 1-54, ECRI Institute.
"Infusion Pumps, Large-Volume," Healthcare Product Comparison System, 2010, pp. 1-51, ECRI Institute.
Anonymous, Guardrails® Safety Software—Medley TM Medication Safety System, Alaris Medical Systems XP-00234431; 2002 Alaris Medical Systems Inc. Nov. 2002, SSM @2159C.
Baldauf-Sobez et al., "How Siemens' Computerized Physician Order Entry Helps Prevent the Human Error," Electromedica, vol. 71, No. 1, 2003, pp. 2-10.
Calabrese, et al., "Medication administration errors in adult patients in the ICU," Intensive Care Med, 2001, pp. 1592-1598, vol. 27, Springer-Verlag.
Eskew, James et al., Using Innovative Technologies to Set New Safety Standards for the Infusion of Intravenous Medications, Hospital Pharmacy, vol. 37, No. 11, pp. 1179-1189, 2002, Facts and Comparisons.
Kohn, et al., "To Err is Human—Building a Safer Health System," National Academy Press, 2002, pp. i-287, 1-287, National Academy of Sciences.
Lesar, "Recommendations for Reducing Medication Errors," Medscape Pharmacists, posted Jul. 24, 2000, 10 pgs, vol. 1(2), Medscape Pharmacists, <http://www.medscape.com>.
Meier, "Hospital Products Get Seal of Approval at a Price," The New York Times, Apr. 23, 2002, 5 pgs.
Shabot, et al., "Wireless clinical alerts for critical medication, laboratory and physiologic data," System Sciences 2000. Proceedings of the 33rd Annual Conference on Jan. 4-7, 2000, Piscataway, NJ, IEEE, Jan. 4, 2000.
Williams, et al., "Reducing the Risk of User Error with Infusion Pumps," Professional Nurse—Safe Practice—Infusion Devices, Mar. 2000, pp. 382-384, vol. 15(6).
Yokoi, "Prevention of Errors in Injection/Drip Infusion—No excuse for ignorance!—Essential Points of Accident Prevention, IV Infusion Pump, Syringe-pump Accident Prevention," JIN Special, Igaku Shoin K.K., Dec. 1, 2001, pp. 109-120, No. 70.
Queensland Health. Use of returned or unused dispensed medicines, Jan. 5, 2005, Queensland Government. pp. 1-2.
International Search Report and Written Opinion for PCT/US2012/029544 dated Sep. 28, 2012 in 8 pages.
Canadian Office Action for Application No. 2551903, dated Mar. 28, 2017, 7 pages.
European Office Action for Application No. 12756903.6, dated Apr. 19, 2017, 5 pages.
Office Action for United Arab Emirates Application No. UAE/P/0962/2013, dated Apr. 17, 2017, 18 pages.
Australian Examination Report No. 1 for Application No. 2016216550, dated Sep. 20, 2017, 3 pages.
Chinese Office Action for Application No. 201480015147.6, dated Nov. 16, 2017, 8 pages.
European Communication of the Board of Appeal for Application No. 05791269.3, dated Nov. 10, 2017, 7 pages.
European Office Action for Application No. 14775918.7, dated Dec. 20, 2017, 8 pages.
European Office Action for Application No. 14779655.1, dated Jul. 28, 2017, 6 pages.
Memo concerning Mexican Office Action for Application No. MX/a/2015/015959, dated Sep. 21, 2017, 4 pages.
Chinese Office Action for Application No. 2012800136388, dated Jul. 18, 2016, 2 pages excluding machine translation.
Extended European Search Report for Application No. 14779655.1, dated Jul. 14, 2016, 8 pages.
Extended European Search Report for Application No. 14780320.9, dated Jul. 1, 2016, 7 pages.
Extended European Search Report for Application No. 14801713.0, dated Jan. 16, 2017, 8 pages.
Chinese Office Action for Application No. 201480015025.7, dated Jan. 23, 2018, 11 pages excluding English summary.
Chinese Office Action for Application No. 201480015036.5, dated Jan. 23, 2018, 13 pages excluding English translation.
European Office Action for Application No. 14779655.1, dated Mar. 8, 2018, 7 pages.
Japanese Office Action in Application No. 2016-501081, dated Feb. 9, 2018, 4 pages.
Memo concerning Mexican Office Action for Application No. MX/a/2015/015959, memo dated Mar. 2, 2018, 1 page.
Canadian Office Action for Application No. 2512991, dated Jan. 10, 2018, 4 pages.
Canadian Office Action for Application No. 2828898, dated Jan. 11, 2018, 8 pages.
Australian Examination Report No. 2 for Application No. 2012228997, dated Dec. 11, 2015, 3 pages.
Chinese Second Office Action for Application No. 2012800136388, dated Feb. 15, 2016, 8 pages excluding translation.
U.S. Appl. No. 13/901,501, filed May 23, 2013.

(56) References Cited

OTHER PUBLICATIONS

Extended European Search Report for Application No. 14775918.7, dated Sep. 13, 2016, 10 pages.
Chinese First Office Action for Application No. 2012800136388, dated Jul. 23, 2015, 15 pages.
Canadian Office Action for Application No. 2551903, dated Mar. 5, 2018, 8 pages.
Chinese Office Action for Application No. 201480015147.6, dated May 3, 2018, 6 pages.
European Office Action for Application No. 14772937.0, dated Apr. 19, 2018, 9 pages.
Chinese Office Action for Application No. 201480015147.6, dated Mar. 10, 2017, 10 pages excluding translation.
Canadian Office Action for Application No. 2512991, dated Mar. 2, 2017, 4 pages.
Extended European Search Report for Application No. 14801726.2, dated Jan. 5, 2017, 8 pages.
Australian Office Action for Application No. 2014241022, dated Feb. 7, 2019, 4 pages.
Australian Office Action for Application No. 2014241019, dated Feb. 6, 2019, 3 pages.
Chinese Office Action for Application No. 201480015025.7, dated Oct. 9, 2018, 27 pages.
Chinese Office Action for Application No. 201480015036.5, dated Sep. 29, 2018, 20 pages.
Chinese Office Action for Application No. 201480041362.3, dated Oct. 18, 2018, 13 pages.
Japanese Office Action for Application No. 2016-501081, dated Nov. 2, 2018, 6 pages.
Canadian Office Action for Application No. 2828898, dated Dec. 7, 2018, 5 pages.
Chinese Office Action for Application No. 201480015093.3, dated Jul. 16, 2018, 16 pages.
Non-Final Office Action dated Oct. 14, 2014, issued in U.S. Appl. No. 11/326,145.
Australian Office Action for Application No. 2014241019, dated Dec. 5, 2019, 5 pages.
Australian Office Action for Application No. 2014268828, dated Nov. 25, 2019, 3 pages.
Canadian Office Action for Application No. 2828898, dated Dec. 3, 2019, 6 pages.
Canadian Office Action for Application No. 2901024, dated Jan. 27, 2020, 5 pages.
Chinese Office Action for Application No. 201480015025.7, dated Nov. 12, 2019, 20 pages.
Chinese Office Action for Application No. 201480015093.3, dated Dec. 4, 2019, 17 pages.
European Office Action for Application No. 14801713.0, dated Dec. 11, 2019, 6 pages.
United Arab Emirates Office Action from KIPO for Application No. UAE/P/1554/2015, first received Nov. 21, 2019, 11 pages.
Australia Office Action for Application No. 2014268828, dated Jul. 3, 2020, 5 pages.
Chinese Office Action for Application No. 201480041985.0, dated May 15, 2020, 23 pages.
India Office Action for Application No. 4041/KOLNP/2015, dated Jul. 8, 2020, 8 pages.
Australian Office Action for Application No. 2020201641, dated Oct. 9, 2020, 4 pages.
Canadian Office Action for Application No. 2551903, dated Aug. 18, 2020, 3 pages.
Canadian Office Action for Application No. 2828898, dated Oct. 7, 2020, 7 pages.
Chinese Office Action for Application No. 201480041985.0, dated Sep. 3, 2020, 38 pages.
Canada Office Action for Application No. 2900564, dated Jan. 28, 2020, 4 pages.
Brazil Office Action for Application No. BR112015029135-0, dated Feb. 12, 2020, 5 pages.
Brazil Office Action for Application No. BR112015019758-2, dated Feb. 20, 2020, 5 pages.
India Office Action for Application No. 7050/CHENP/2013, dated Sep. 18, 2019, 7 pages.
Australian Office Action for Application No. 2014241019, dated Aug. 12, 2019, 4 pages.
Australian Office Action for Application No. 2014241022, dated Jun. 25, 2019, 3 pages.
Australian Office Action for Application No. 2014268828, dated Jul. 26, 2019, 4 pages.
Australian Office Action for Application No. 2018232958, dated Aug. 7, 2019, 3 pages.
Chinese Office Action for Application No. 201480015025.7, dated Jun. 24, 2019, 25 pages.
Chinese Office Action for Application No. 201480015036.5, dated Jun. 24, 2019, 20 pages.
European Summons to attend oral proceedings pursuant to Rule 115(1) EPC for Application No. 14772937.0, dated Jul. 17, 2019, 12 pages.
Australian Office Action for Application No. 2014241022, dated Sep. 30, 2019, 4 pages.
Chinese Office Action for Application No. 201480015036.5, dated Nov. 5, 2019, 12 pages.
Chinese Office Action for Application No. 201480041985.0, dated Sep. 23, 2019, 24 pages.
European Communication for Application No. 14779655.1, dated Oct. 2, 2019, 12 pages.
Japanese Office Action for Application No. 2016501081, dated Nov. 12, 2019, 6 pages.
Japanese Office Action for Application No. 2019-030891, dated May 27, 2020, 8 pages.
India Office Action for Application No. 2625/KOLNP/2015, dated Jul. 8, 2020, 7 pages.
Canadian Office Action for Application No. 2900564, dated Nov. 19, 2020, 4 pages.
Canadian Office Action for Application No. 2901024, dated Nov. 20, 2020, 6 pages.
Extended European Search Report for Application No. 20191537.8, dated Dec. 17, 2020, 9 pages.
Japanese Office Action for Application No. 2019-030891, dated Nov. 26, 2020, 5 pages including English translation.

* cited by examiner

SCALABLE COMMUNICATION SYSTEM

CROSS-REFERENCE TO RELATED APPLICATIONS

This application is a continuation of U.S. application Ser. No. 13/421,776, entitled "SCALABLE COMMUNICATION SYSTEM," filed on Mar. 15, 2012, which is a nonprovisional of U.S. Application Ser. No. 61/453,853, entitled "COMMUNICATION USER INTERFACE," filed on Mar. 17, 2011, and U.S. Application Ser. No. 61/555,820, entitled "COMMUNICATION INTERFACE," filed on Nov. 4, 2011, the entirety of each of which is incorporated herein by reference.

BACKGROUND

Field

The present disclosure is related to intersystem communications, and more particularly, to messaging conversion systems and methods to provide intersystem communication between multiple systems.

Hospitals and other caregiving institutions typically employ a number of different electronic device and data systems to carry out many of the functions of the hospital. These different data systems often utilize incompatible signaling and communication protocols for the various types of systems, which can include Admit-Discharge-Transfer (ADT), physician order entry (POE), electronic Medicine Administration Record (eMAR), and others. Certain data systems, for example a medication management system such as the Pyxis MedStation™ system, receive information from one or more of these other systems on a continuous basis. As each data system may use a different message protocol or data structure, messages cannot be sent directly from one data system to another without customizing one or both data systems. Further, different manufacturers will also use different protocols, making control and communication between data systems very difficult. The maintenance and updating of multiple customized data systems to communicate within a complicated interconnected network of data systems within a hospital is a complex and sizeable task.

One approach that has been taken to integrate multiple systems within a hospital environment is to use a messaging conversion system that receives messages from different external sending data systems in formats native to each of the external sending data systems, interprets the content of the message, creates a new message in the native format of an external destination data system, and sends the new message to the external destination data system. The messaging traffic passing through this messaging conversion system may be sizeable, depending on what systems are installed in a hospital. For a hospital using an exemplary Pyxis MedStation™ system, every new entry or modification of an existing entry in any of the ADT, POE, eMAR, Material Management Information System (MMIS), Pharmacy Information System (PIS), Operating Room Information System (ORIS), and Anesthesia Information System (AIS) needs to be provided to the Pyxis MedStation™ system so that current information is available to the nurse at each of the Pyxis MedStation™ Automated Dispensing Machines (ADMs). In addition, information on each dispensed medication must be provided by the Pyxis MedStation™ system to at least the eMAR and patient billing systems. In a 500-bed hospital, for example, where the average patient is receiving 10-12 medications multiple times per day with the physician's orders changing daily, the number of messages that require conversion can exceed 100,000 messages per day. In addition, the messages are not evenly spread through the 24 hours of a day and tend to be generated at certain peak times, such as the time of the daily rounds or the regular medication administration times (such as 8 am, noon, 4 pm, and 8 pm) for that hospital. The messaging load at peak times can be very high and yet it is still critical to maintain low latency on the availability of the information to the nurses, so messaging conversion systems are frequently designed to handle the peak loads.

One drawback to traditional messaging conversion systems is that the conversion solution is not readily scalable or extendible. Some messaging conversion systems require that a specific conversion software module be written for each connection between external data systems, requiring multiple software modules to be created if one data system is providing information to multiple other data systems, or if there are multiple interconnections between multiple data systems. The conversion software modules may be hosted on individual machines if the messaging software is not configured to efficiently manage multiple conversion software modules running in parallel. In a large hospital, there may be fifty or more of these one-to-one direct conversion systems in place to integrate multiple data systems across multiple sites. Therefore, the hospital's information technology (IT) system may have fifty or more servers each running one conversion software module. Maintaining this many systems, both from hardware and software perspectives, is challenging. As each one-to-one conversion link passes through a different server, each of the sending data systems must be provided with the identification of the server linked to each destination data system.

Some traditional data systems provide "durable messaging" in that each message that passes through the conversion system is stored for some period of time. In many implementations, this is provided as a circular buffer in the nonvolatile memory of the server that stores a copy of the as-received message. This provides a message recovery capability in the event of a component or system failure. After the failure is corrected, the messages that were received within a defined period of time prior to the failure, such as one hour, can be re-converted and re-sent to ensure receipt by the destination data system. When the messaging conversion system includes multiple independent modules running on multiple servers, the coordination of this buffering and validation so that it works properly for all modules can be a challenge.

Modifying, upgrading, or extending a system of the complexity described above can eventually become extremely difficult to perform and even harder to validate, which may lead to a reduction in service or reliability of the data exchange for the large hospital systems that depend the most upon this type of integration to provide quality care to their patients.

SUMMARY

It is desirable to provide a system and method of converting messages being sent between data systems using different communication protocols and message structures that is easily scalable and extensible to new data systems. The systems and methods disclosed herein utilize, in certain embodiments, a system having an interface module for each data system. Each interface module comprises information on the communication protocol and data structure used by that data system and is configured to both receive messages from and transmit messages to a particular data system. In certain embodiments, an interface module for a first data system will comprise information about which other systems receive messages from the first data system.

In certain embodiments, a communication system is disclosed that includes an interface module configured to accept a first message from an external data system in a native message format of the external data system, convert at least a portion of the first message into a message in an internal messaging format, and provide the internal messaging format message.

In certain embodiments, a communication system is disclosed that includes an interface module that is configured to be coupled to a first external data system. The interface module includes an input queue, a message queue, and an output queue. The interface module is configured to accept a first message from the first external data system in a first native message format, store the accepted first message in the first native message format in the input queue, retrieve the first message from the input queue, convert the retrieved first message into an internal messaging format, provide the first message in the internal messaging format to another interface module, accept a second message in the internal messaging format from another interface module, store the accepted second message in the internal messaging format in the message queue, retrieve the second message from the message queue and convert the retrieved second message into the first native message format, store the converted second message in the first native message format in the output queue, and retrieve the second message from the output queue and provide the second message in the first native message format to the first external data system.

In certain embodiments, an adapter configured to adapt message communications between a first external data system and other different external data systems is disclosed, wherein at least some of the different external data systems have different native message formats from the first external data system. The adapter includes a transport component configured to send a message to and receive a message from the first external data system. The messages comprise information. The adapter also includes a protocol component coupled to the transport component. The protocol component is configured to interpret the received message and extract at least a portion of the information in the received message. The adapter also includes a mapping component configured to transform at least a portion of the extracted information into a message comprising an internal messaging format.

In certain embodiments, a centralized communication system is disclosed that includes a plurality of adapters configured to communicate with a respective plurality of external data systems in a plurality of native message formats of the respective plurality of external data systems and provide and accept internal messaging format messages in an internal messaging format and a core coupled to the plurality of adapters. The core is configured to receive an internal messaging format message in the internal messaging format from a first adapter and provide the internal messaging format message in the internal messaging format to at least one second adapter.

In certain embodiments, a method of interfacing a plurality of external data systems is disclosed. The method includes the steps of receiving from a first external data system a message in a first native message format of the first external data system, mapping at least as portion of the received message into an internal messaging format, mapping at least a portion of the internal messaging format message into a second message in a second native message format of a second external system, and providing the second message to the second external data system.

In certain embodiments, a system for managing a communication system is disclosed. The system includes a memory and a processor. The memory may be configured to store message routing information related to internal messages transmitted between a plurality of adapters of a centralized communication system. The internal messages may correspond to external messages received from one of a plurality of external systems, wherein the internal messages are formatted in accordance with an internal messaging format, and the external messages are formatted in accordance with a plurality of external messaging formats native to the plurality of external systems. The processor may be configured to determine a topology of the centralized communication system based on the message routing information related to the internal messages transmitted between the plurality of adapters. The processor may also be configured to provide a graphical representation of the determined topology of the centralized communication system.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Interoperability has become complex and challenging within the healthcare environment as many hospitals typically employ many different applications and devices developed by many different vendors on an everyday basis. An integration solution that allows data or information exchanged between the systems at both the vendor's and the user's ends and allows all systems working together seamlessly is desired. The vendor's end may include, for example, a HIS such as any, or any combination of, an ADT system, a patient order data system, a formulary data system, an ORIS, an electronic medical record (EMR) system, an MMIS, a billing system, and a packaging system. The user's end may include various application or patient devices such as a dispensing device, an infusing device, and a ventilator operated by a nurse, a caregiver, or even the patient himself or herself.

A hospital requires a number of systems to manage the large number of medications and supplies that constantly flow through a hospital. It is critical to the hospital's ability to provide quality care for their patients that the proper medications and supplies are available at all times to the staff. It is also important that the inventory of medications and supplies be carefully managed to reduce the costs associated with the amount of on-hand inventory and expiration of medications and supplies. Simultaneously achieving both of these objectives requires specialized computer systems to track and manage specific types of medications and supplies. The consoles that manage each system and the interface gateways that then link these consoles and some individual systems to the hospital's EHR are collectively grouped as the data and communication system 100 of the hospital.

Figure 1A:
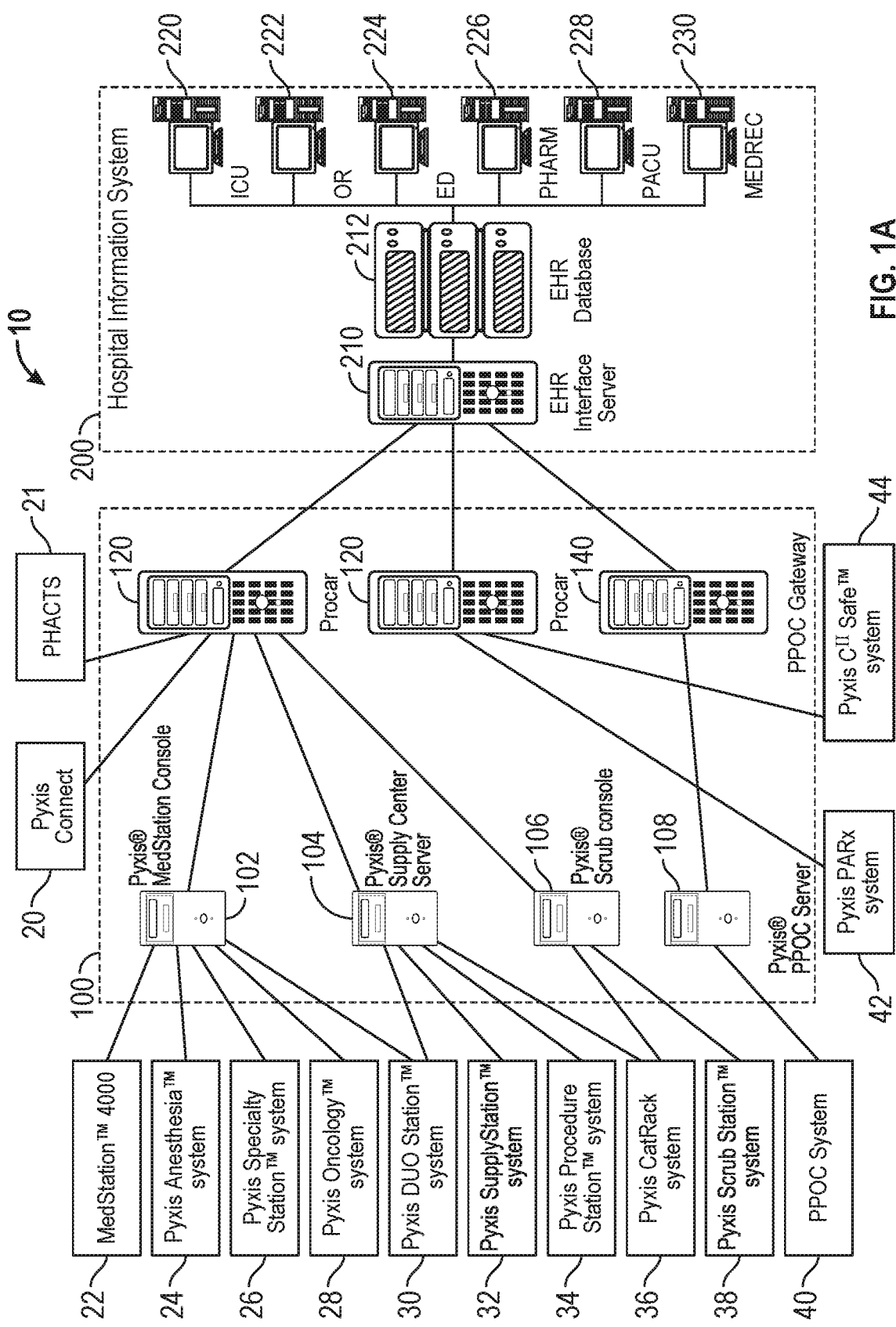
FIG. 1A depicts a system architecture of a hospital data system.
Figure 1B:
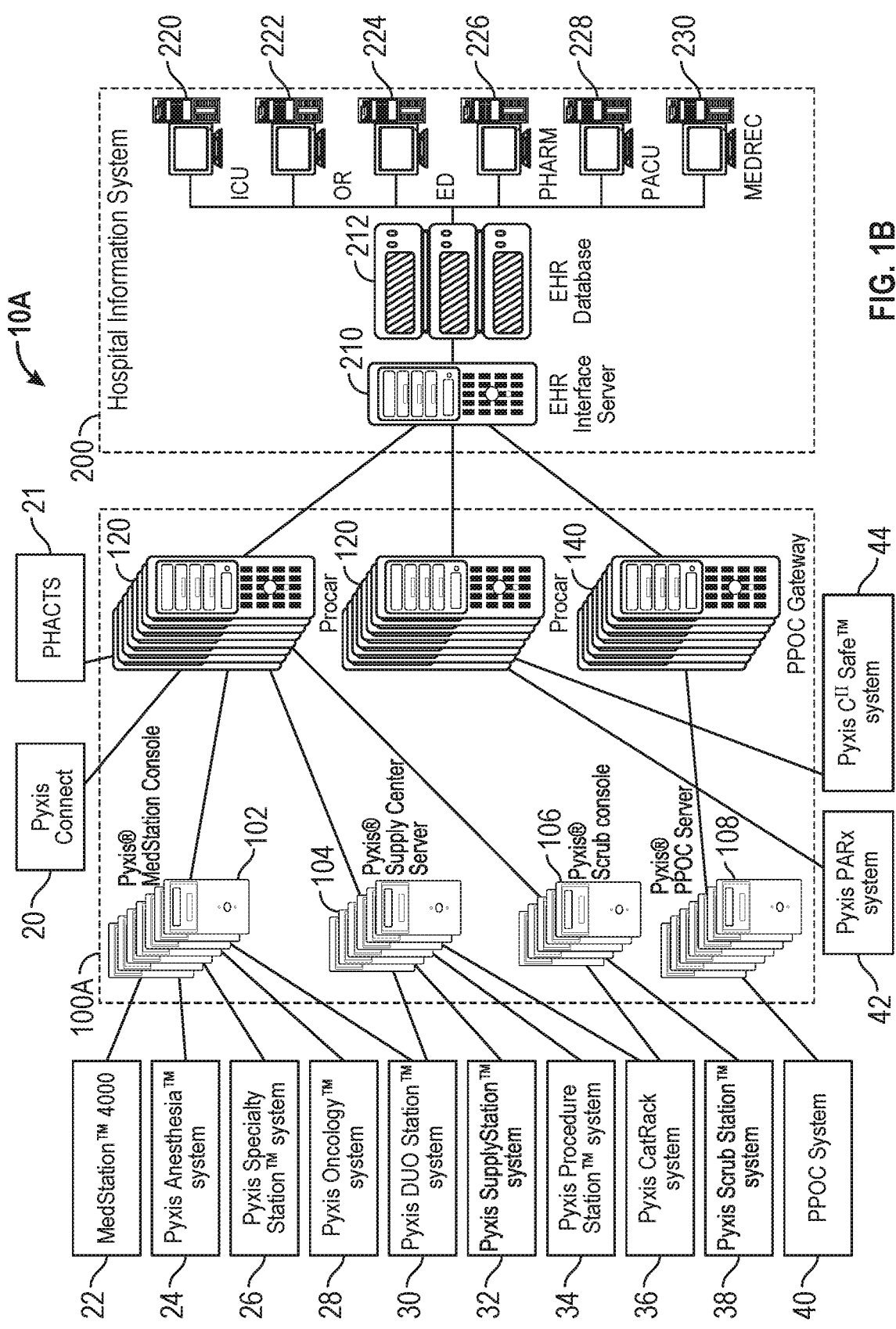
FIG. 1B depicts an example of a system architecture deployed at a healthcare Integrated Delivery Network (IDN) having forty hospital sites.

FIGS. 1A and 1B provide highly schematic depictions of hospital data systems 10. Although a relatively large number of interconnections are shown in these figures, this is schematic only, as the physical implementation is much more complex, requiring a significantly larger number of interconnections than illustrated. Each of the hospital data systems 10 has a hospital information system (HIS) 200. The HIS 200 has, in this example, a number of separate electronic health record (EHR) systems, including an intensive care unit (ICU) system 220, an operating room (OR) system 222, an emergency department (ED) system 224, a pharmacy (PHARM) system 226, a post-anesthesia care unit (PACU) system 228, and a medical records (MEDREC) system 230. Each of these systems is networked to a EHR database 212. The HIS 200 also has an EHR interface server 210 to communicate with other data systems in the hospital.

In FIGS. 1A and 1B, a number of different specific data systems are shown for explanatory purposes. Such data systems are well-known, so that further details regarding the individual specific data systems are not provided. In this example, the hospital has deployed Pyxis Medstations™ 22 to store and dispense medications at the nurses stations, providing distributed access to the medications needed to treat the patients. In this example, the hospital also uses one or more Pyxis® Anesthesia Systems 24 to store and manage the medications used by anesthesiologists in the operating room, Pyxis SpecialtyStations™ 26 to store specific medications and supplies in individual treatment areas, and Pyxis OncologyStations™ 28 in oncology departments to manage the specialized and hazardous medications used to treat cancer. Pyxis DuoStations 30 are used in areas that require storage of both medications and supplies. All of these medication management devices 22, 24, 26, 28, 30 are controlled from a Pyxis MedStation console or server 102.

Supplies in the hospital in this example are managed by similar devices controlled from a Pyxis Supply Center server 104. Pyxis DuoStations 30 are linked to the Supply Center server 104 as well as the MedStation console 102. Pyxis Supply Station systems 32 are used to store supplies at points of care around the hospital. Pyxis Procedure Station systems 34 provide storage for equipment and supplies used in specialized areas such as perioperative environments and procedural suites. The hospital uses one or more Pyxis CatRacks 36 to store the supplies used in cardiac units and radiology labs, including such items as pacemakers, stents, and catheters. The scrubs worn by the doctors and nurses are dispensed and collected using Pyxis ScrubStations® systems 38 that may be placed near operating rooms as well as staff locker rooms. Both the Pyxis CatRacks 36 and the Pyxis ScrubStations 38 are linked to both the Supply Center server 104 and a Pyxis Scrub server 106.

In this example, the hospital uses a Pyxis Patient Point of Care (PPOC) verification system 40 to manage the administration of medications. This data system 40 communicates with its own Pyxis PPOC server 108 which, in turn, communicates through a dedicated PPOC Gateway 140 to the HIS 200.

Each of the servers 102, 104, 106 and 108 communicates with the HIS 200 through a message forwarding device called a Procar 120. In this example, the Procar 120 communicates with the various EHR systems 220, 222, 224, 226, 228, 230 through the EHR interface server 210. The Procar 120 includes custom translation packages for each of the servers 102, 104, 106, and 108 that convert the information flowing from the respective consoles to the format needed by the respective EHR system with which each console exchanges information.

The hospital also uses several data systems that do not have dedicated servers or consoles. The Pyxis Connect system 20 captures medication orders from physicians and transfers them to the pharmacy, where a pharmacist reviews the orders and releases them in the medication management system. The hospital uses the PHACTS® system 21 to manage medications within the pharmacy and pharmacy-managed devices. The exemplary hospital uses a Pyxis PARx® system 42 within the pharmacy to gather medications to replenish the distributed dispensing devices within the hospital. The pharmacy also uses a Pyxis CII Safe™ system 44 to store controlled substances within the hospital. All of these data systems 20, 21, 42, 44 communicate through a PROCAR 120 to the HER systems 220, 222, 224, 226, 228, 230.

It can be seen that the communication system 100 contains redundant elements, such as multiple consoles or servers 102, 104, 106, 108 managing devices with similar or overlapping capabilities, as well as multiple interface systems 120, 140 that are each tailored to linking specific consoles 102, 104, 106, 108 and independent systems 20, 21, 42, 44 to specific EHR systems 220, 222, 224, 226, 228, 230. While the function of each of the gateways 120, 140 is similar if not identical, the customized nature of the translation packages requires a significant amount of labor to rewrite and validate the new translation package that would be required to enable a change from one gateway to another. Maintaining such a complex system that includes multiple generations of products as well as similar devices from multiple companies is difficult and expensive, which may result in a reduction in system reliability as well as increased support costs. Furthermore, the introduction of any new devices into the system may require a large amount of effort and expenditure to create new translation packages so that communication may be had between the existing devices in the system and the new devices.

FIG. 1B depicts an example of a conventional communication system 100A deployed in a data system 10A at an Integrated Delivery Network (IDN) having forty hospital sites. This system 10A uses the same architecture as the system 10 of FIG. 1A, but replicated across the sites. As each server 102, 104, 106, and 108 may be limited to handling devices 22, 24, 26, 28, 30, 32, 34, 36, 38, and 40 that are on a local network, the servers 102, 104, 106, and 108 may need to replicated at each of the forty hospital sites.

In this example, the various gateways 120, 140 may be unable to handle multiple connections from the replicated servers 102, 104, 106, and 108 due to the processing requirements of the individual custom translation packages. The software of some systems may be configured to be the sole software running on a given processor, requiring that each new copy of a translation package be deployed on its own hardware platform. This results in the replication of the gateways 120, and 140 within the communication system 100A. A single hospital may require dozens of identical servers running parallel translation packages. This is characteristic of a system that is neither scalable or extendible, as each new connection, for example a connection between a new MedStation console 102 and the PHARM EHR system 226, requires a complete replication of the hardware and software of the Procar 120. This is neither cost effective nor straightforward to implement and may lead to additional support costs.

Within the following description, the centralized communication system (CCS) is described as being connected to a variety of external devices and data systems. In the examples and discussion presented herein, a "data system" is interchangeable with a "device," especially with regard to the external devices and data systems connected to the CCS.

Figure 2A:
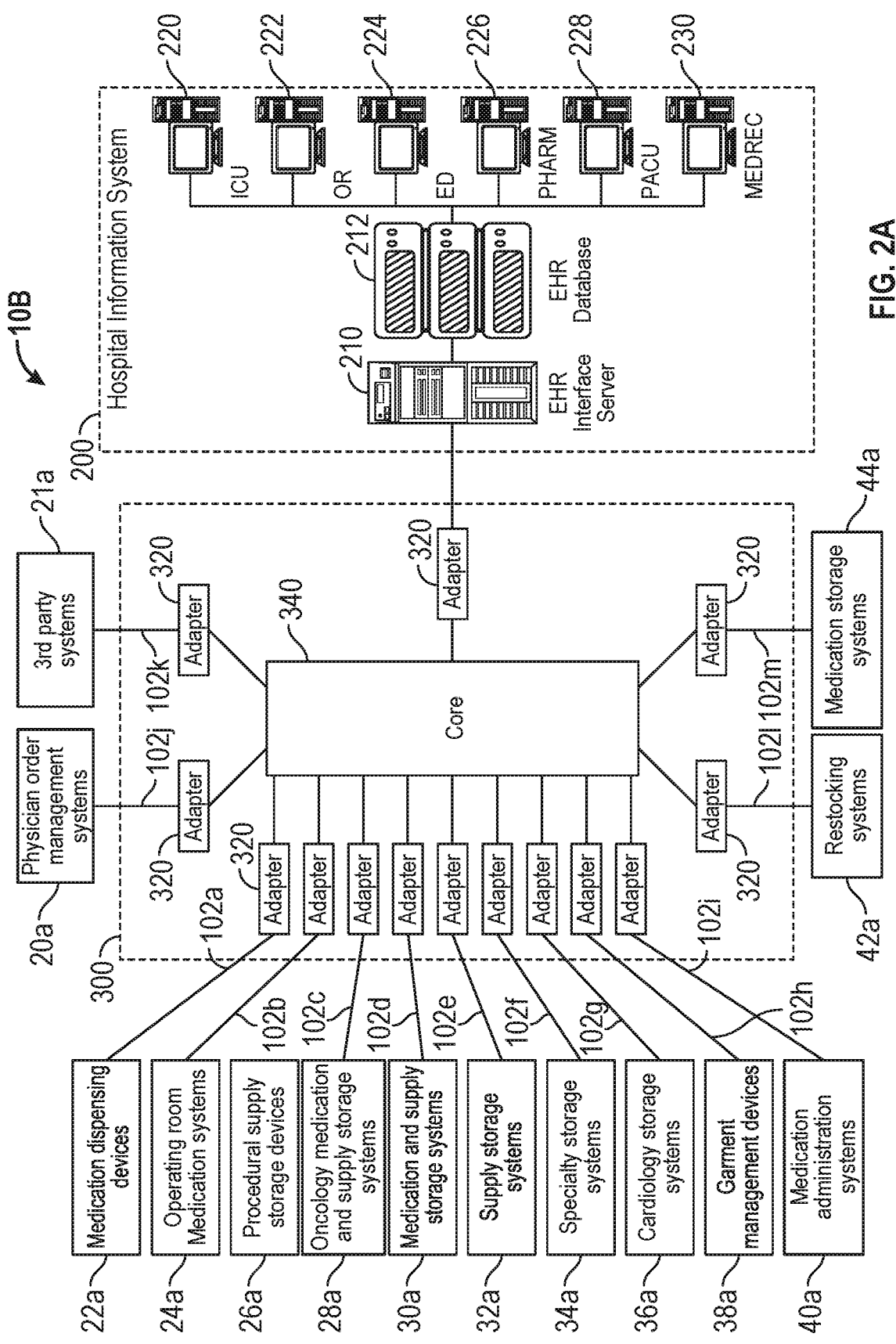
FIG. 2A depicts an exemplary system architecture for a centralized communication system (CCS) as it would be deployed at the same IDN of FIG. 1B according to certain aspects of the present disclosure.

FIG. 2A depicts an exemplary system architecture for a CCS 300 deployed within a hospital system 10B within the same IDN as for the hospital data system of FIG. 1B according to certain aspects of the present disclosure. It is to be noted that the hospital system the following description is exemplary only, made for illustration purposes. The systems and methods of the present disclosure are not limited to the specific devices or configurations that are illustrated and described. As one of ordinary skill in the art will appreciate, the CCS systems and methods presently disclosed are applicable to other configurations and devices to provide an intercommunication system. The CCS 300 creates a layer of abstraction between the medical devices and data systems 20a, 21a, 22a, 24a, 26a, 28a, 30a, 38a, 40a, 42a and 44a, such that each sending or destination device or data system does not have to know the details of the other devices and data systems in the hospital system or the IDN, but only needs to know about the data and protocols with which it is normally configured to operate. (The medical devices and data systems are referenced with a suffix "a" in FIGS. 2A and 2B to designate generic systems without regard to source.) For example, an automated dispensing machine (ADM) contains data related to inventory but the infusion system may only care about the inventory information of the drugs that are infusing through an infusion pump in an infusion system. As another example, the Point of Care (POC) system 40 may only be configured to be concerned about alerts of a medication override but nothing else from a dispensing system.

The CCS 300 includes an adapter 320, i.e. an interface module 320, for each external device or data system that is part of the hospital's data system 10B. In certain embodiments, an adapter can have more than one interface module. Each adapter 320 is built from a common basic structure, or "framework", and customized according to the particular native message format used by the external device to be connected to that adapter 320. The structure of adapter 320 is discussed in greater detail with respect to later figures. The CCS 300 also includes a core 340 that transfers messages in an internal messaging format between the adapters 320. The internal messaging format is common to all internal messaging format messages regardless of which adapter 320 is providing the internal messaging format message or which adapter 320 is receiving the internal messaging format message. The internal messaging format is described in greater detail with respect to at least FIG. 13.

In certain embodiments, the core 340 transfers internal messaging format messages from a first adapter 320 to one or more second adapters 320 according to information provided by the first adapter 320, thereby functioning in a "push" communication mode. In certain embodiments, the core 340 functions only to transfer internal messaging format messages between adapters 320 and does not process the internal messaging format messages. In certain embodiments, there may be more than one core 340 provided in the hospital system 10B or within an IDN. For example, an IDN having forty hospital sites may have a CCS 300 deployed at each of the forty hospital sites, with the cores 340 of each of the CCSs 300 configured to transfer the internal messaging format messages between the cores 340 when an adapter 320 of a CCS 300 at one hospital site is sending an internal messaging format message to an adapter 320 of the CCS 300 at another hospital site. In certain embodiments, a CCS 300 includes an adapter 320 connected to external devices at multiple physical sites. Alternatively, or in addition, the adapters 320 may be implemented in a web service architecture.

The CCS 300 can be extended to a new external device by adding a new adapter 320. The new adapter 320 is created starting with the adapter framework and adding elements to at least identify the other one or more external devices to which the internal messaging format messages are to be sent.

In certain embodiments, the CCS 300 comprises a non-volatile memory (not shown in FIG. 2A), for example one or more magnetically encoded hard disks or flash memory. In certain embodiments, messages that have been received by the adapters 320 are stored in the as-received format, i.e. the native message format of the external device that provided the message to the adapter 320, in the non-volatile memory. In certain embodiments, the internal messaging format messages are stored at one or more steps in the transfer process in the non-volatile memory. In certain embodiments, messages that are to be provided by the CCS 300 to external devices are stored in the native format of the destination external device prior to being provided to the external device. The storage of incoming, internal, and outbound messages in the non-volatile memory provides a "durable messaging" capability, i.e. messages will not be lost if the CCS 300 suffers a power loss or other interruption of operation. In certain embodiments, the core 340 resumes the transfer of internal messaging format messages by retrieving the in-process messages from the non-volatile storage. In certain embodiments, the adapters 320 resume providing outbound messages to external devices by retrieving in-process messages from the non-volatile memory. In certain embodiments, the CCS 300 stores the messages in a database (not shown in FIG. 2A) that is stored on the non-volatile memory. In certain embodiments, the storage of messages within the CCS 300 is implemented as queues at various points in the flow of messages through the CCS 300. The queues are described in greater detail with respect to at least FIGS. 7, 8, 9A, and 9B.

Figure 2B:
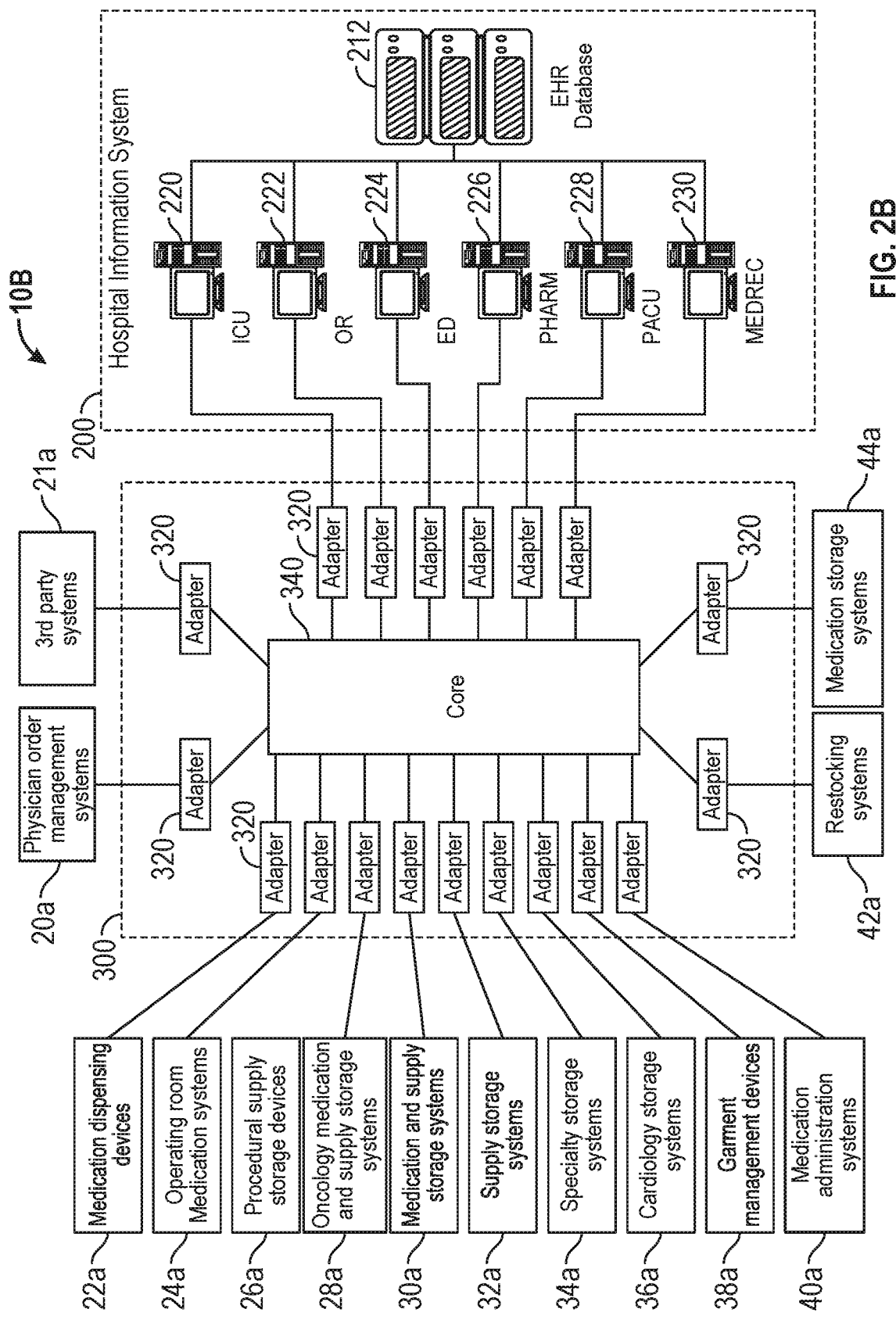
FIG. 2B depicts another exemplary system architecture for a CCS according to certain aspects of the present disclosure.

FIG. 2B depicts another exemplary system architecture for a CCS 300 according to certain aspects of the present disclosure. In this embodiment, individual adapters 320 are provided for each of the EHR systems 220, 222, 224, 226, 228, 230 of the HIS 200. In certain embodiments, an adapter 320 attached to a medical device, for example a medication dispensing device 22a, can send a message directly to a particular EHR system, for example the PHARM system 226.

The CCS 300 greatly simplifies the connections that are required to provide intersystem communication between diverse devices, relative to conventional communication arrangements. This feature of the systems and methods of the present disclosure is even more appreciated when the number of devices in the hospital system and/or IDN is increased.

Figure 3:
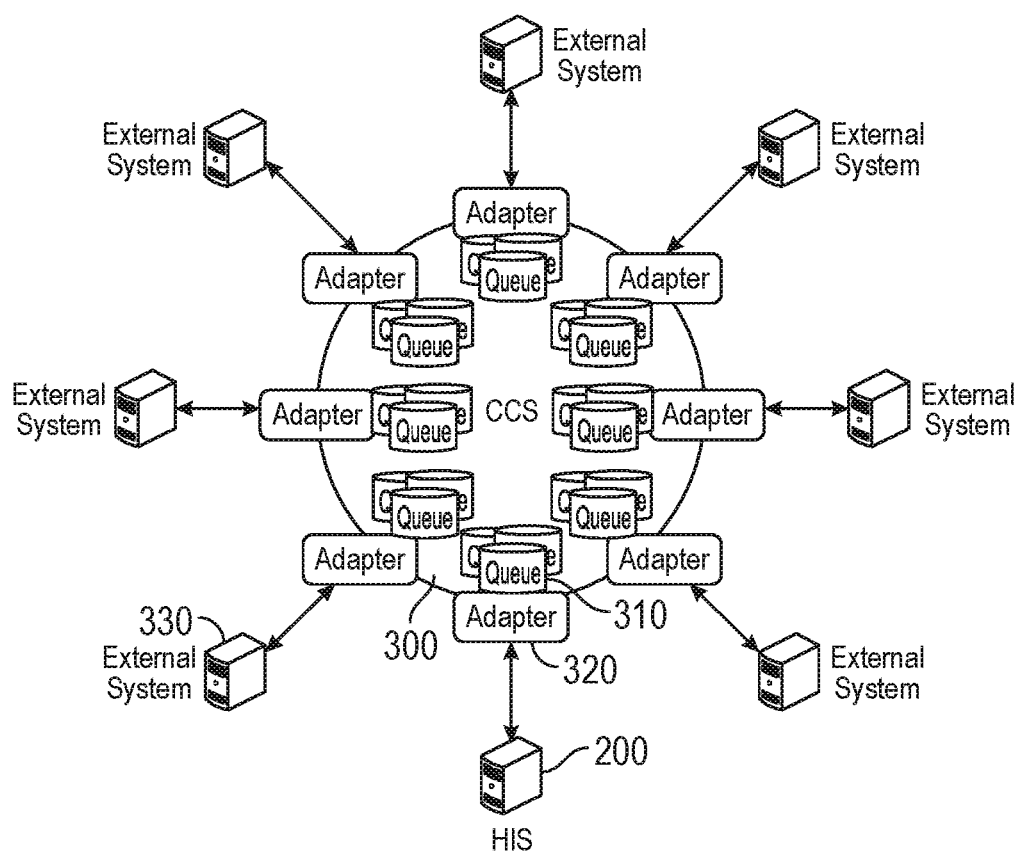
FIG. 3 is an overview of a CCS providing a central integration point between medical products and Hospital Information Systems (HISs) according to certain aspects of the present disclosure.

FIG. 3 is a conceptual depiction of the CCS 300 providing a central integration point between external data systems (generally referred to by reference numeral 330) and the Hospital Information System (HIS) 200 according to certain aspects of the present disclosure. Data in different formats from the external data systems 330 are mapped and/or transformed into a common messaging system (CMS) format, also referred to herein as an "internal messaging format." Once data from a sending external data system 330 is provided by an adapter 320 in the internal messaging format, this data can be changed (or "converted" or "mapped" or "translated", "transformed", etc.) by the CCS 300, for example, into any of the other formats of the receiving (or "destination" or "target") data systems 330 according to certain aspects of the present disclosure. Hence, the sending data systems 330 and the receiving data systems 330 are still able to operate according to their own native data format and protocols, with the CCS 300 performing the translation to allow a sending data system 330 to communicate with a receiving data system 330.

As will be explained in more detail later, queues 310 and adapters 320 are employed to regulate and/or direct the flow of messages and provide the translations of the data and messages that are needed. Each device or data system 330, and the HIS 200, connected to the CCS 300, has its own queue(s) 310 and adapter 320, in accordance with certain aspects of the present disclosure. The individual adapters 320 provide the translations that are specific for each device 330, and translate the specific data formats of the device 330 to the internal messaging format.

Figure 4:
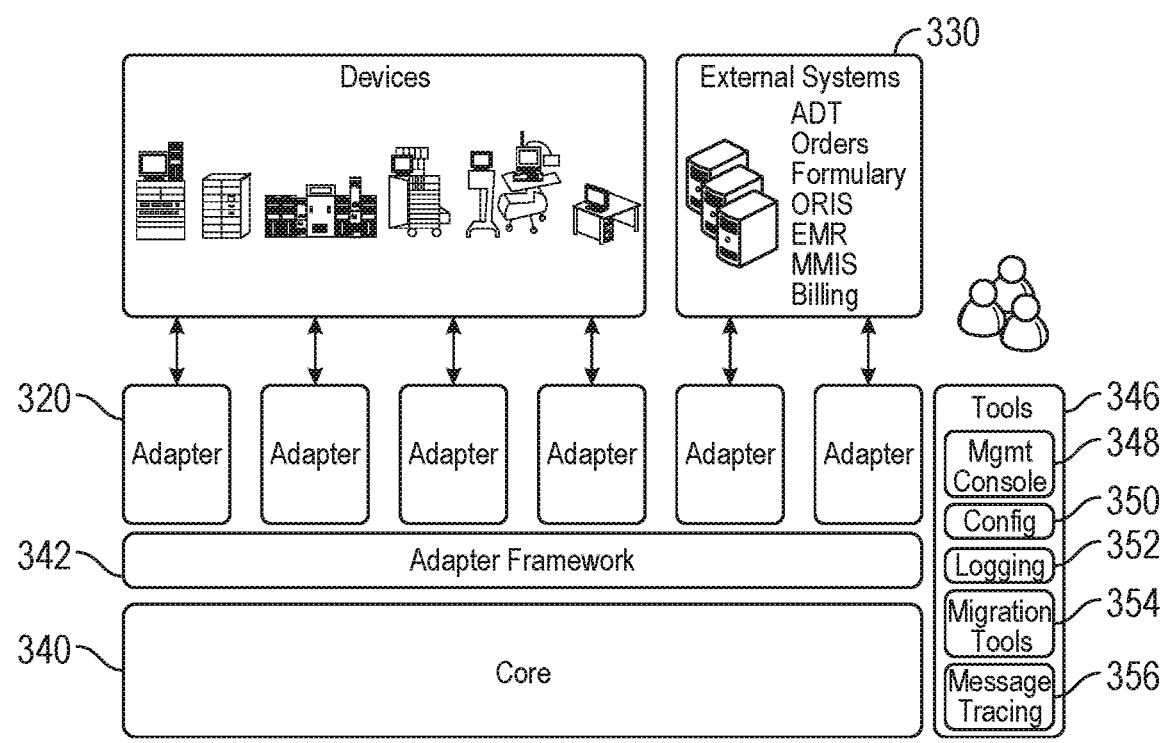
FIG. 4 depicts an overview of the CCS architecture according to certain aspects of the present disclosure.

FIG. 4 depicts an overview of the architecture of the CCS 300 according to certain aspects of the present disclosure. The CCS 300 includes a core 340 and an adapter framework 342 that supports a plurality of the adapters 320. The CCS 300 also includes tools 346, including a management console tool 348, a configuration tool 350, a logging tool 352, migration tools 354 and message tracing tool 356. In FIG. 4, the devices and external data systems are depicted separately, but with the same reference number 330.

The core 340 and adapter framework 342 allows the adapters 320 to be integrated into and connected to the core 340. As shown, each of the adapters 320 can connect devices 330 or data systems 330 to the core 340. In certain aspects, an empty adapter framework 342 is provided to readily enable additional adapters 320 to plug in without the need for changing the core 340.

Figure 5:
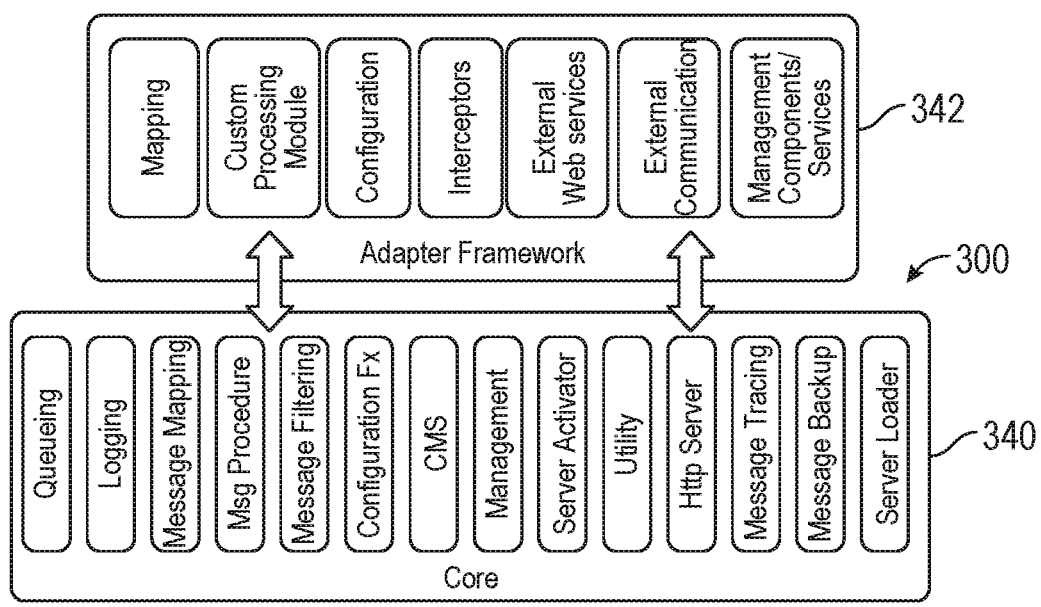
FIG. 5 depicts details of the core and adapter framework of FIG. 4 according to certain aspects of the present disclosure.

FIG. 5 depicts in greater detail the core 340 and adapter framework 342 of the CCS 300 according to certain aspects of the present disclosure. In the core 340, the messaging system is a "push-type" messaging system. The messaging system uses message queues (310 in FIG. 3) in a database for persistent storage of the messages. Every message that is pushed to the CCS 300 will pass through a message queue 310 before being routed to its destination. In push-type messaging, message destinations are determined by the sender which means that as the message arrives at a particular CCS adapter 320, this adapter 320 will determine where this message will be sent to through configuration. In other embodiments, the messaging system 300 may be a "publish-subscribe system" where a destination selects what message it wants to receive.

The CCS 300 features durable messaging or reliable messaging. The adapter framework 342 implements a mechanism whereby each message will not be automatically removed from a queue 310 until the sending data system 330 acknowledges that it has been received by the destination data system 330. Messages in the CCS 300 are processed by default in the order in which they are received. However, the order in which the messages in the CCS 300 are processed may vary by implementation.

As seen in FIG. 5, the core 340 may include, in certain aspects, various message components of queuing, logging, message mapping, message procedure, message filtering, common message system, management services, server component adaptor, utility, Http server, message tracking, message backup, and server component loaders. These components can be dynamically loaded at run-time based on component registration or global assembly cache. Each of the components is pluggable and implements at least one interface, defines its interface identity (ID) and its class ID. A component loader loads a component dynamically based on the class id and interface id thereof. In certain embodiments, one component can implement multiple different interfaces where each interface has its own interface id.

The adapter framework 342 includes the components of message mapping, custom message processing, configuration, interceptors, external web service, external communication, and management components/services.

Figure 6:
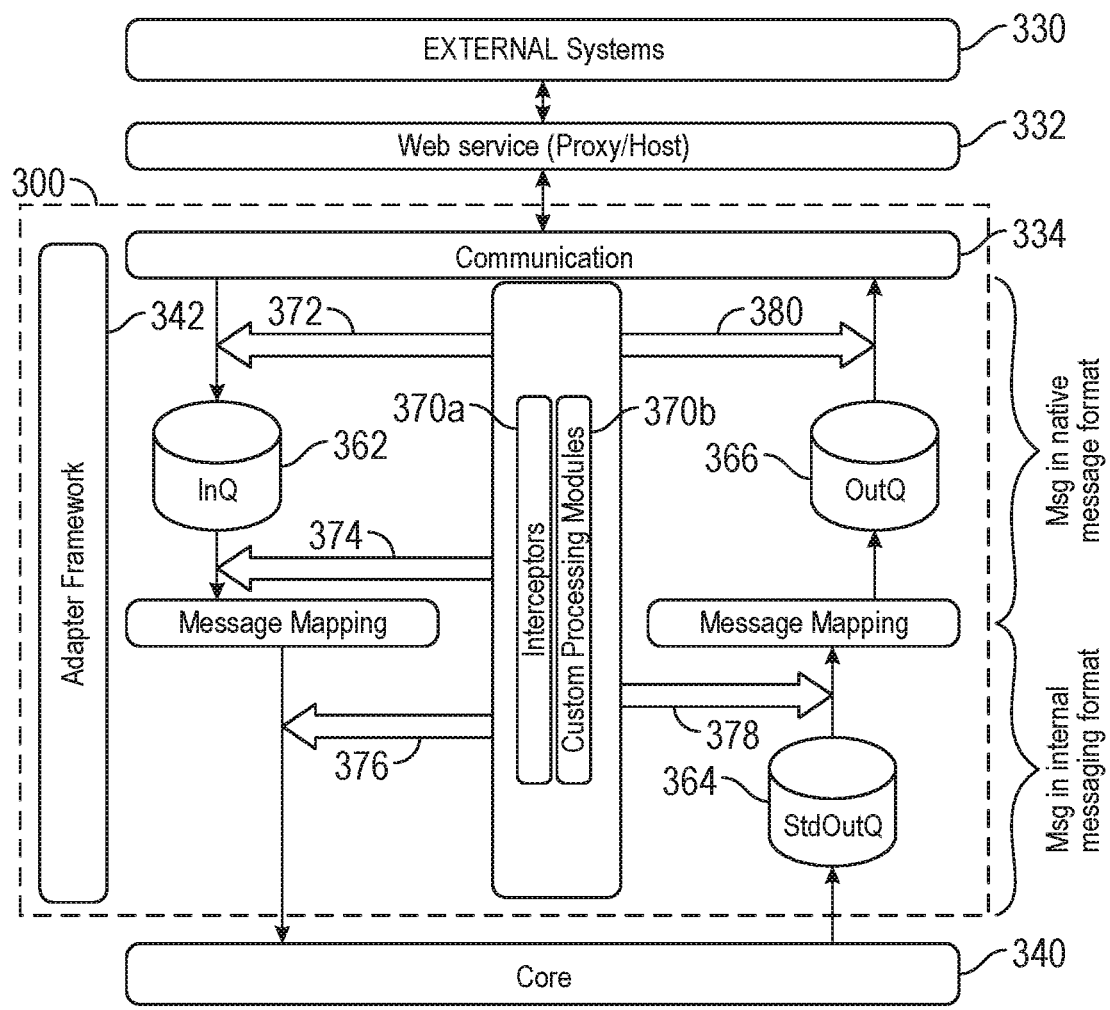
FIG. 6 depicts a message life-cycle according to certain aspects of the present disclosure.

FIG. 6 depicts a message life-cycle according to certain aspects of the present disclosure. There are three check points that, in a default configuration, are part of a message life-cycle These checkpoints are the In-Queue (InQ) 362, the Standard-Out-Queue (StdOutQ) 364, and the Out-Queue (OutQ) 366. These queues 362-366 were collectively referenced as message queues 310 in FIG. 3. If the CCS 300 shuts down at any time, the processing of the messages will re-start at the previous checkpoint of each message due to the use of the queues 362-366. The CCS 300 supports asynchronous message patterns between adapters 320. The core 340 and adapter framework 342 provides extendible message flow control to provide a consistent message processing within the entire CCS 300 no matter what type of adapters 320 will be developed in the future, for use with new types of devices or systems, for example.

The adapter framework 342 implements a set of processing modules 370 that allow interactions with the messages that flow through the CCS 300. These interfaces are divided into two categories: "interceptors" 370A & "custom processing modules" (CPMs) 370B as depicted in FIG. 6. Both interceptors 370A and CPMs 370B have the ability to interact with messages at the same plug-in points in the message flow path. Hence, the messages can be processed, manipulated, translated, copied, stored, etc., at certain plug-in points. In the exemplary embodiment of FIG. 6, the various plug-in points are referenced by reference numerals 372, 374, 376, 378, and 380.

According to certain aspects of the disclosure, multiple interceptors 370A can be applied at a particular plug-in point, for example plug-in point 374, and the order in which the multiple interceptors 370A execute can be configured, for example, at the time of implementation of the CCS 300. Interceptors 370A can be applied across more than one adapter 320 to provide an aspect-type of data processing which means that the same interceptor 370A can be used for multiple adapters 320. For example, a message backup interceptor 370A can be used for many adapters 320 to provide a generic backup mechanism. According to certain aspects of the disclosure, a CPM 370B has a higher precedence than an interceptor 370A. This means that a CPM 370B can overwrite what an interceptor 370A has done to a message. In certain embodiments, CPMs 370B cannot be shared across multiple adapters 320.

Interceptors 370A and CPMs 370B are both allowed to interact with the flow of the message at the following locations, according to certain aspects of the disclosure.

Pre-InQueue 362, at plug-in point 372: as a message in the native message format arrives from a sending external data system 330 through a web service 332, and prior to persisting, this plug-in point 372 allows the adapter 342 to perform custom processing on the native format message, i.e. the format of the message native to the sending external data system 330.

Post InQueue 362, at plug-in point 374: as the native format message is persisted in InQueue 362 and prior to mapping/transforming to the CMS format, this plug-in point 374 allows the adapter 320 to perform any custom processing on the native format message, i.e. the format of the message native to the sending external data system 330.

Post message mapping, at plug-in point 376: after the sending native message is mapped and/or transformed into the internal messaging format, also referred to as the CMS format, and before the now internal messaging format message leaves the receive adapter 320, this plug-in point 376 allows the adapter 320 to perform any custom processing on the internal messaging format message.

Post StdOutQueue 364, at plug-in point 378: before the internal messaging format message is mapped and/or transformed to a destination native message format, this plug-in point 378 allows the adapter 320 to perform any custom processing on the internal messaging format message while it is in the internal messaging format.

Post OutQueue 366, at plug-in point 380: before the now destination native format message is sent to the external data system 330 by a communication component 334, this plug-in point 380 allows the adapter 320 to perform any custom processing on this destination native format message in the destination native format, i.e. the format of the message native to the destination external data system 330.

Since the plug-in points 376, 378 allow messages to be processed in the internal messaging format, any interceptors 370A or CPMs 370B that process messages at plug-in points 376, 378 may be able to process the messages irrespective of the particular sending external data system 330, and irrespective of the messaging format native to the particular sending external data system 330. Thus, any interceptors 370A or CPMs 370B that process messages at plug-in points 376, 378 may be reusable across any of the external data systems 330, in addition to any external data systems added in the future, without having to rewrite, or customize any such interceptors 370A or CPMs 370B for each external data system 330.

Figure 7:
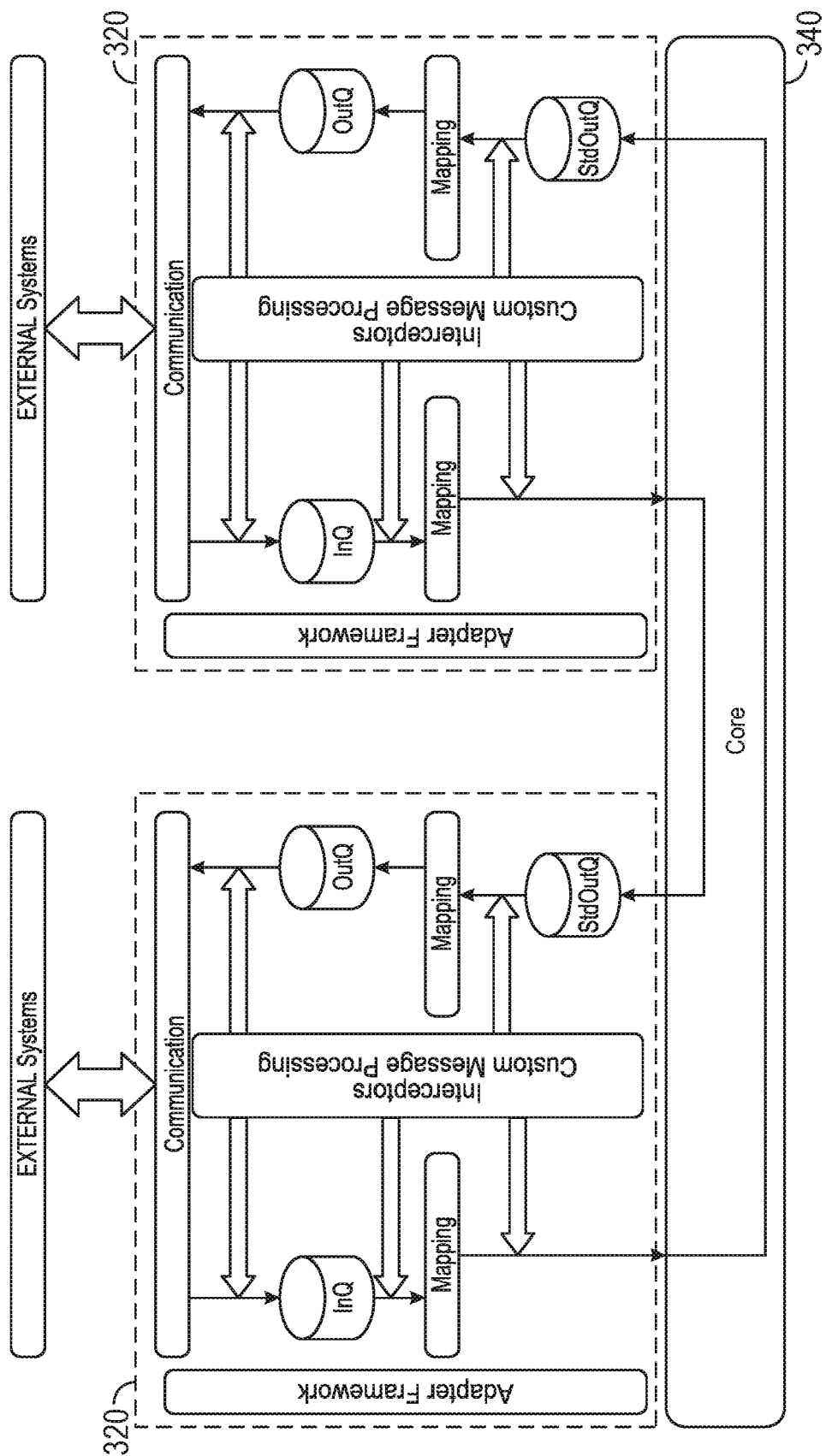
FIG. 7 depicts the flow of messages between two CCS adapters through the core according to certain aspects of the present disclosure.

FIG. 7 depicts the flow of messages between two adapters 320 through the core 340 according to certain aspects of the present disclosure. This figure depicts two adapters 320 communicating through the core 340 for illustration purposes. In practice, a greater number of adapters 320 are generally coupled to the core 340, enabling a multitude of devices and data systems 330 to communicate with each other.

Figure 8:
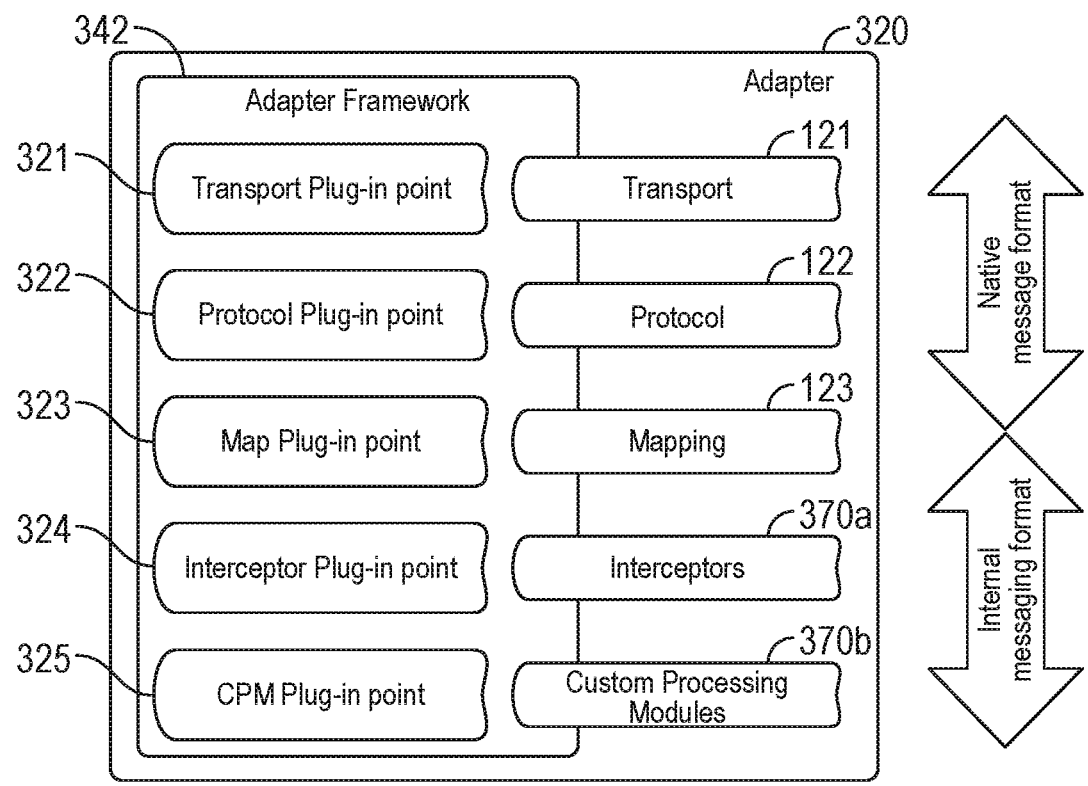
FIG. 8 depicts the elements and connection of various elements of an adapter according to certain aspects of the present disclosure.

FIG. 8 depicts elements and connections of various elements of an adapter 320 according to certain aspects of the present disclosure. As discussed previously, an interceptor 370A is a set of components that can be plugged into the adapter framework to perform particular operations such as storing a copy of a message, replicate a message into multiple copies, or perform custom processing for particular system. A particular interceptor 370A may be used at multiple different plug-in points within an adapter or across multiple adapters.

Adapters 320 are sets of components that provide plug-in points between external data systems and the CCS 300. According to certain aspects of the disclosure, each adapter 320 comprises transport, protocol, map and business logics plug-in points.

Transport logic (component) 121 is responsible for sending and receiving data streams to and from external data systems 330. The transport component 121 deals with bits and bytes. Each transport component will have to implement a set of software interfaces so that it can be plugged into the adapter framework 342 via the transport plug-in point 321.

Protocol logic (component) 122 is responsible for interpreting data streams by implementing particular communication hand shakes between two endpoints. The protocol component 122 detects the beginning and the end of the message so that messages can be extracted from data streams. In addition to extracting messages from data streams, the protocol component 122 also is responsible for detecting error conditions and recovering from errors if the errors are recoverable. Each protocol component 122 implements a set of software interfaces so that it can be plugged into the adapter framework 342 via a protocol plug-in 322.

Map logic (component) 123 is responsible for transforming a message in native message format from an external data system 330 to the internal messaging format (CMS) or from the internal messaging format to a native message format. The map component 123 will be plugged in at deployment time. The map component 123 comprises translation tables, data element mapping and message structure definition. The map component needs to understand the native message format, know how to convert (map, translate, transform, etc.) the native message format to the internal messaging format and know how to map individual data elements in native message format to the internal messaging format. The map component 123 plugs into the map plug-in point 323.

Figure 9A:
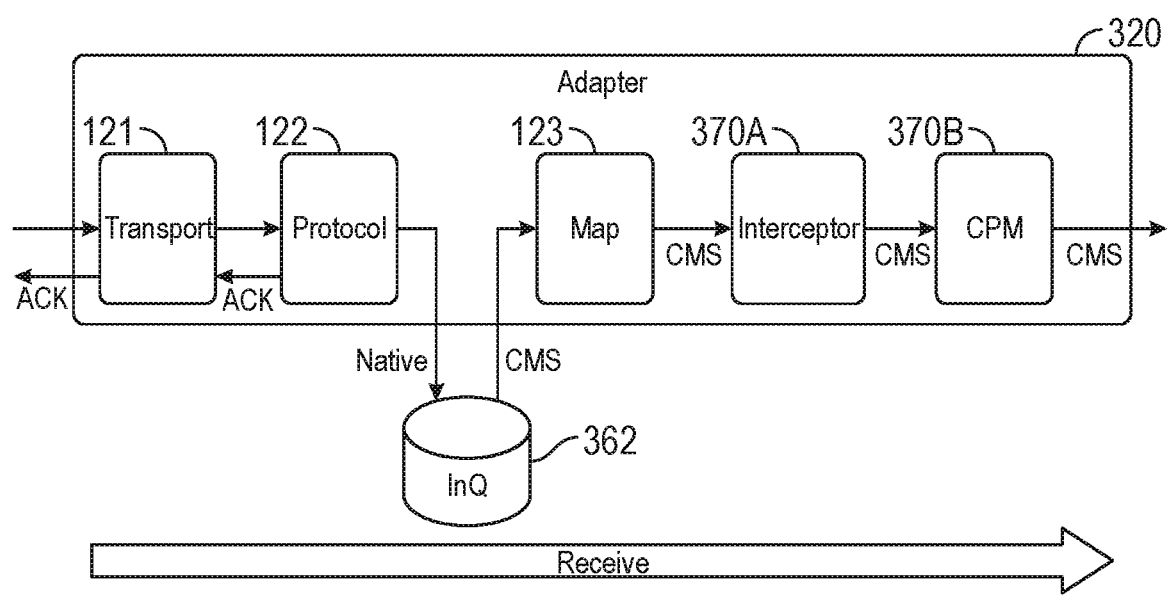
FIGS. 9A and 9B depict the message flow through a CCS adapter according to certain aspects of the present disclosure.
Figure 9B:
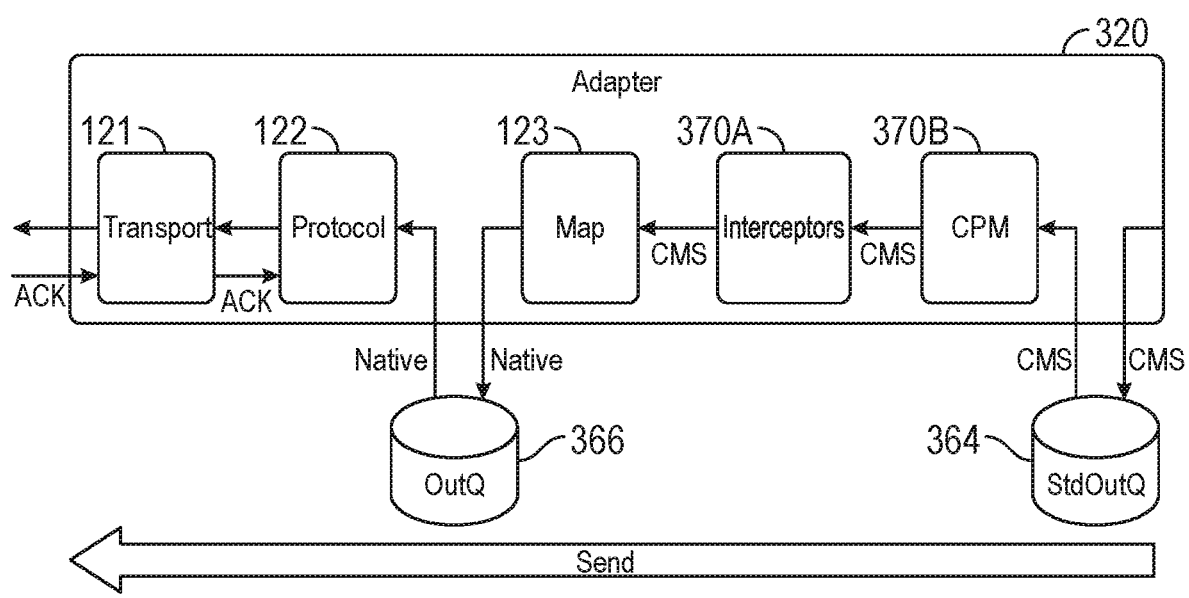

FIGS. 9A and 9B depict an exemplary message flow through an adapter 320 according to certain aspects of the present disclosure. The depiction is similar to that shown in FIG. 6, but also shows the transport, protocol, map, interceptor and CPM modules. FIG. 9A depicts the flow of received messages that are received at the core 340 from a sending external data system. The transport component 121 receives a native message format message in a native message format from an input port (TCP/IP or Serial) and the native message format message is passed to the protocol component 122. The protocol component 122 extracts the information in the native message format message, stores the native message format message in the native message format in the InQueue 362, and sends an acknowledgement to the transport logic 121. The native message format message is pulled out from the InQueue 362 and mapped by the map component 123 to an internal messaging format message, i.e. a message in the format used in the CMS. This internal messaging format message is then passed through series of one or more interceptors 370A and CPMs 370B. The internal messaging format message is then provided to a message transfer system, i.e. the core 340 (not shown in FIG. 9A), for routing.

In the outbound flow path of FIG. 9B, the CPM 370B receives an internal messaging format message in the internal messaging format from the core 340 (not shown in FIG. 9B) and stores the internal messaging format message in the StdOutQueue 364. The internal messaging format message is then retrieved from the StdOutQueue 364 and passed to one or more interceptors 370A and to the CPM 370B. Once processing is completed, the internal messaging format message is mapped by the map component 123 into the native message format of the destination data system 330 and is stored into the OutQueue 366. The protocol component 122 retrieves the native message format message from the OutQueue 366 and adds necessary message protocol framing. The transport component 121 sends the protocol framed message to the external data system 330. Once the external data system 330 acknowledges the message, the protocol component 122 removes the native message format message from the OutQueue 366.

Once the core 340 receives an internal messaging format message from the adapter 320, the core 340 uses its configurable routing table to find out which of the adapters 320 are the recipients of the internal messaging format message. The core 340 will push the internal messaging format message to the destination adapter(s) 320. Since, in one example, the core 340 is a push messaging system, the routing tables are determined by the sending (or source) adapter 320. The sending adapter 320 determines where the internal messaging format message shall be routed. It is up to the destination adapter 320 to determine whether it wants to accept the internal messaging format message or not. If the destination adapter 320 does not want to accept a particular internal messaging format message, the destination adapter 320 is configurable to send a signal to inform the messaging system whether the specific internal messaging format message is acceptable or should be blocked. This allows the destination external data system 330 to select desired communications and filter out unwanted communications, regardless of where the communication is generated.

Figure 10A:
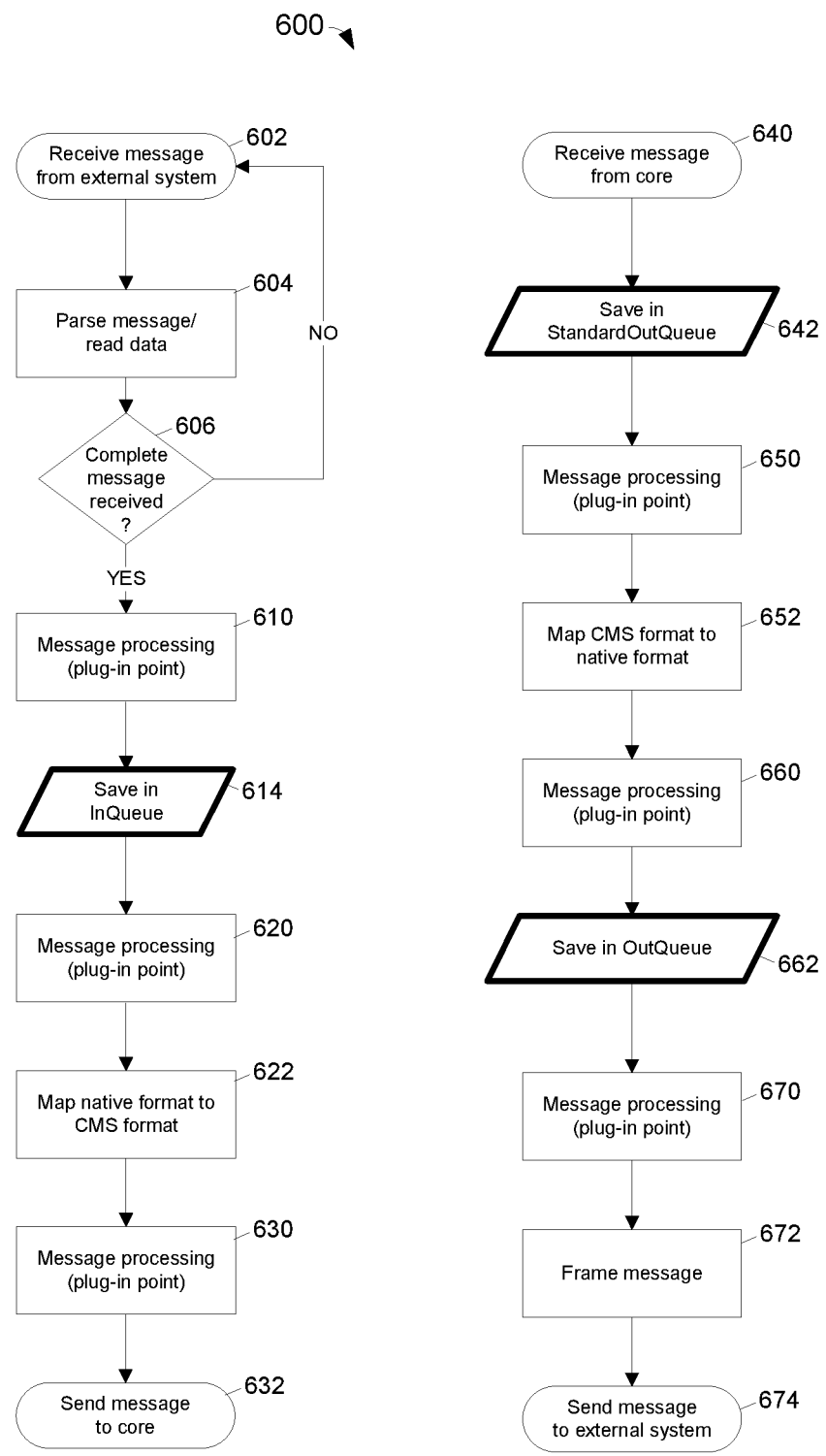
FIG. 10A is an exemplary message processing flowchart according to certain aspects of the present disclosure.

FIG. 10A is an exemplary message processing flowchart 600 according to certain aspects of the present disclosure. Steps 602-632 are related to processing and handling of in-bound messages from external data systems, and steps 640-674 are related to processing and handling of out-bound messages to external data systems. In certain embodiments, all of the steps of process 600 are performed by a single adapter 320, such as shown in FIG. 2, and connected to a single external data system that communicates in a native format according to a native protocol. In certain embodiments, an adapter 320 is configured to communicate with multiple external devices and data systems in a native message format used by all of the multiple external devices and data systems. In certain embodiments, an adapter 320 is configured to communicate with multiple external devices and data systems in their respective native message formats.

The in-bound process starts at step 602 with the receipt of a message from the external system. The message is parsed and interpreted in step 604 according to the native message format and protocol used by the external data system 330. Step 606 determines whether the message was successfully received. If not, the process branches along the 'no' path back to step 602 to request a repetition of the transmission.

If the message was successfully received, the process branches along the 'yes' path to step 610.

Step 610 is the first plug-in point in the message process 600. The adapter framework 342 provides a plurality of plug-in points at various points in the process. Step 610 is a post-receipt processing point prior to saving the incoming native message format message in the InQueue 362. There may be no processing of the native message format message at step 610. The details of the processing in step 610 are discussed in greater detail with respect to FIG. 13B. After the native message format message is processed, or not, in step 610, the native message format message is saved in step 614 in the native format in the InQueue 362.

The native message format message is retrieved from the InQueue 362 and made available at a plug-in point 620. Again, there may be no processing or they may be one or more processes that occur at step 620. The native message format message is then mapped to the internal messaging format, i.e. the CMS format, in step 622 and then there is another plug-in point 630 for further processing. The internal messaging format message is then sent to the core 340 to be transferred to one or more destination adapters 320.

The out-bound process starts at step 640 with the receipt of an internal messaging format message in the internal messaging format from the core 340. The internal messaging format message is immediately saved in the StandardOutQueue 364. The internal messaging format message is then retrieved from the StandardOutQueue 364 and made available at a fourth plug-in point 650 for processing. After the processing, if any, is completed in step 650, the internal messaging format message is mapped to the native message format of the external data system in step 652. The native message format message is then available for further processing at plug-in point 660, and then is saved into the OutQueue 366. The native message format message is retrieved from the OutQueue 366 and processed in step 670, if the system is configured to do so, and then framed in step 672 and sent to the external data system in step 674.

In certain embodiments, one or more plug-in points 610, 620, 630, 650, 660, and 670 are omitted in the adapter framework 342. For example, plug-in point 660 is omitted in the embodiments of FIGS. 6 and 7. In certain embodiments, additional plug-in points may be provided at other message flow points not identified herein, for example after receipt of an internal messaging format message from the core 340 and prior to storing the received internal messaging format message in the StandardOutQueue 364.

Figure 10B:
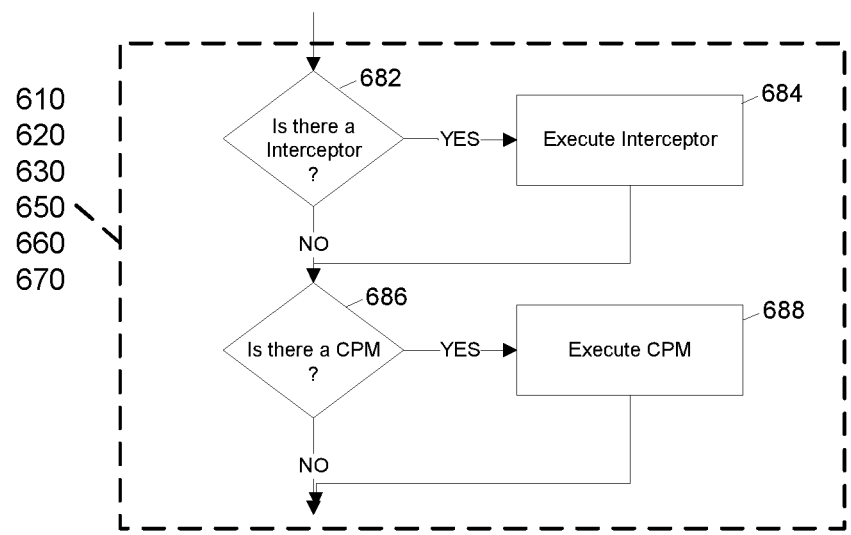
FIG. 10B is an expanded view of a portion of the message processing flowchart of FIG. 10A according to certain aspects of the present disclosure.

FIG. 10B is an expanded view of a portion of the message processing flowchart 600 of FIG. 10A according to certain aspects of the present disclosure. The box marked 610/620/630/650/660/670 in FIG. 10B is an exemplary flow of the processing within any of the plug-in steps of flowchart 600. Two types of processing modules 370 are provided in this example, an interceptor 370A and a custom processing module (CPM) 370B. In this example, the process first determines in step 682 whether an interceptor 370A is configured to process the message in the particular step 610/620/630/650/660/670. If there is, the process branches along the 'yes' path to step 684 and executes the interceptor 370A. In certain embodiments, there is more than one interceptor 370A. In certain embodiments, there is no interceptor 370A configured for the particular step 610/620/630/650/660/670. If there is no interceptor 370A, or after executing an interceptor 370A in step 684, the process arrives at step 686 where it determines whether there is a CPM 370B. If yes, the process branches along the 'yes' path to step 688 and executes the CPM 370B. In certain embodiments, there is only a single CPM 370B in a particular step 610/620/630/650/660/670. In certain embodiments, step 686 and 688 are executed before step 682.

In this example, interceptors 370A are configured to execute algorithms that are used at more than one of steps 610/620/630/650/660/670, or used at a particular step in multiple adapters 320. In this example, CPMs 370B are configured to execute algorithms unique to a particular step 610/620/630/650/660/670 in a CCS 300. In other embodiments, other configuration guidelines are used to determine the number of types of processing modules provided and how they are designated.

In certain embodiments, data can be injected into the message by an interceptor 370A or CPM 370B. For example, a field may be added that identifies the source device or system based on header information received with the message.

Figure 11:
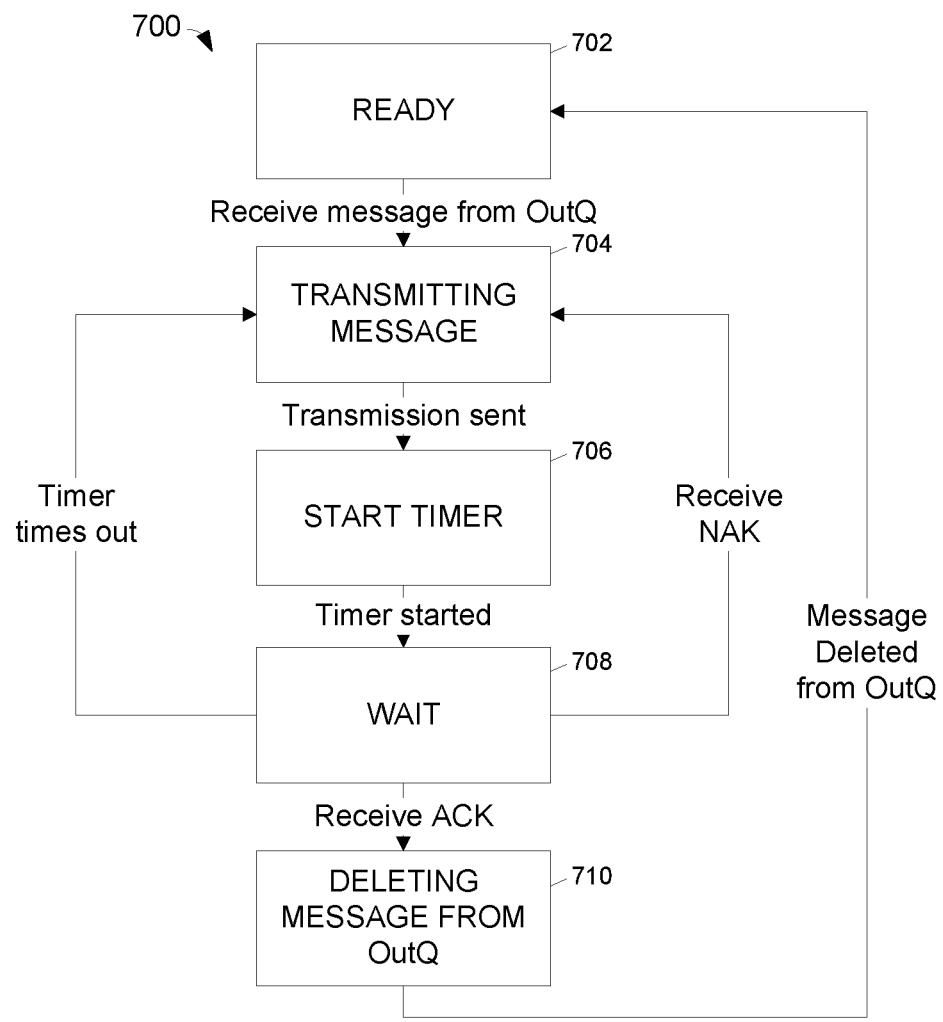
FIG. 11 is a state diagram of the handling of outbound messages according to certain aspects of the present disclosure.

FIG. 11 is a state diagram of the handling of outbound messages according to certain aspects of the present disclosure. The process starts in the ready state 702. Upon receipt of a native message format message from the OutQueue 366, the system transitions to state 704 where the native message format message is transmitted. Upon completion of the transmission, the system transitions to state 706 and starts a timer, then further transitions to wait state 708. If the system receives a NAK, i.e. a message that the transmission was not successfully received, from the external data system 330, or if the timer started in state 706 times out before an ACK or NAK message is received, then the system returns to state 704 and repeats the transmission. If the system receives an ACK from the external data system 330, the system transitions to state 710 wherein the system deletes the native message format message from the OutQueue 366. Upon completion of the erasure, the system transitions back to the ready state and awaits a new native message format message.

The process shown in FIG. 11 is typical of the message handling subsequent to any of the InQueue 362, the StandardOutQueue 364, and the OutQueue 366. As the message is not erased from the respective queue until the message has been confirmed to be received at the next processing step, whether internal or external, the system can repeat the retrieval and transfer of the message in case of power loss or other interruption in the transfer. This provides data persistence and a data recovery capability in the case of a system interruption.

Figure 12:
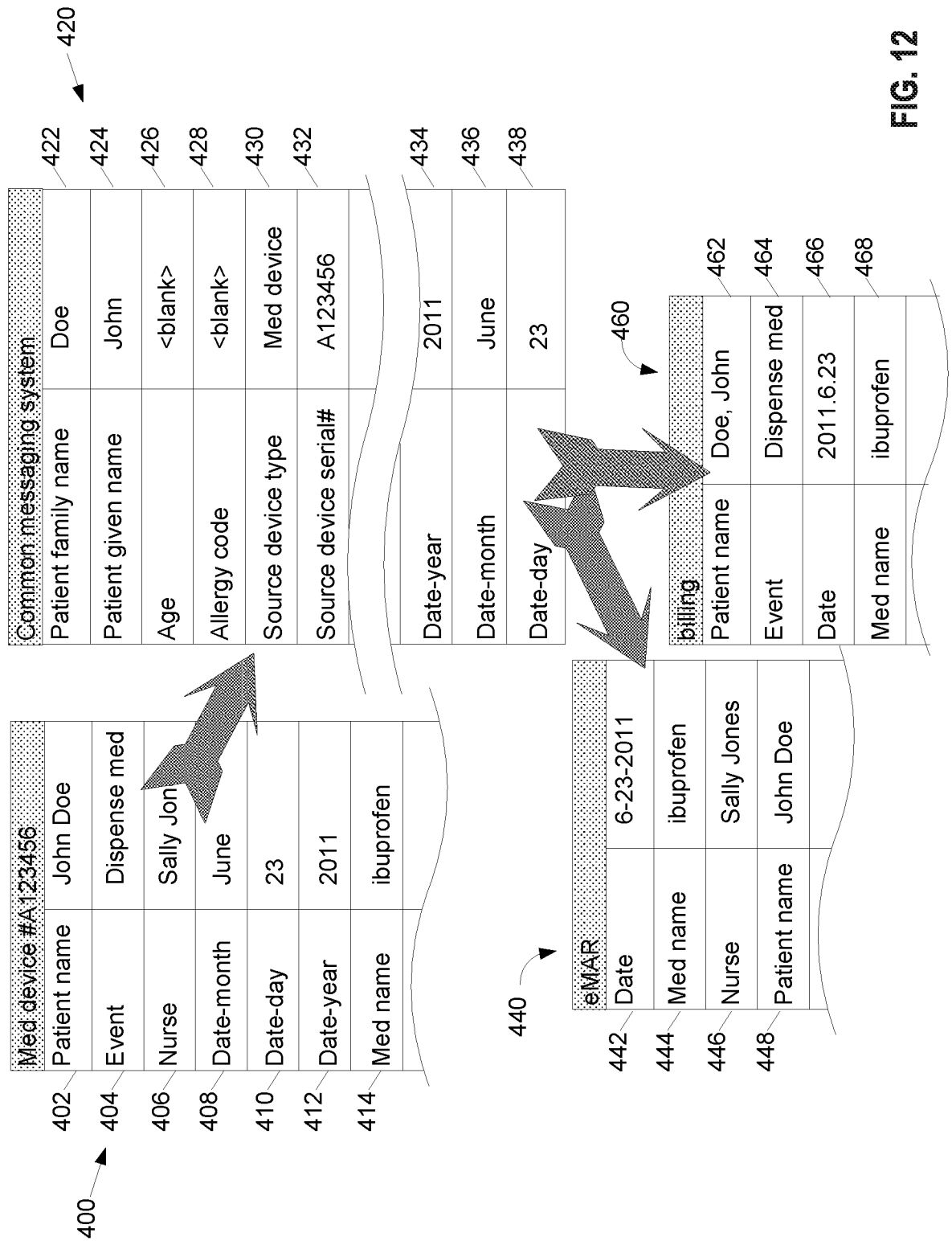
FIG. 12 illustrates the conversion of an inbound message in a first native message format into an internal messaging format message and then into a first outbound message in a second native message format and a second outbound message in a third native message format according to certain aspects of the present disclosure.

FIG. 12 illustrates the conversion of an inbound message 400 in a first native message format (i.e., a native message format message) into an internal messaging format message 420 and then into a first outbound message 440 in a second native message format and a second outbound message 460 in a third native message format according to certain aspects of the present disclosure. In this example, the inbound message is from a device serial #A123456 and reports a medication dispensed for a patient. The device may be an automated dispensing machine, for example. Field 402 is the patient name, which is in a first-last format. Field 404 is the event and field 406 is the name of the patient for whom the medication was dispensed. Fields 408, 410, and 412 are separate fields for the month, day, and year, respectively. Field 414 is the name of the medication that was dispensed.

In this example, the CCS 300 uses the internal messaging format shown for the internal messaging format message 420. The patient name from field 402 of the inbound message 400 has been split into the last name in field 422 and first name in field 424. The internal messaging format has fields 426 for the patient's age and field 428 to identify an allergy of the patient. While the patient has an age and may have an allergy, the inbound (native message format) message 400 does not contain this information so that fields 426 and 428 are blank. Field 430 is the source device type and field 432 is the serial number of the device, extracted from the header of the inbound native message format message 400. The internal messaging format message 420 includes a plurality of other fields, and records the year, month, and day separately in fields 434, 436, and 438 at the end of the message. It can be seen that the order of the date fields has been changed from the month-day-year sequence of the inbound native message format message 400 to the year-month-day sequence of the internal messaging format message 420.

Portions of the information of the internal messaging format message 420 are provided to the eMAR system in message 440 and the billing system in message 460. In certain embodiments, only a first portion of the information of the internal messaging format message 420 is provided in message 440. In certain embodiments, a second and different portion of the information of the internal messaging format message 420 is provided in message 460.

In message 440, the date information of fields 434, 436, and 438 of the internal messaging format message 420 has been concatenated into a month-day-year string in field 442. The third field is the nurse's name. The patient's first and last names from the first and second fields 422 and 424 of internal messaging format message 420 have been concatenated into a first-last string in the fourth field 448 of message 440.

In message 460, the date information of fields 434, 436, and 438 of the CMS message 420 has been concatenated into a year-month-day string in field 466. The third field 446 is the nurse's name. The patient's first and last names from fields 422 and 424 of message 420 have been concatenated into a last-first string in the first field 462 of message 460. The medication name is now the fourth field 468 where it was originally the seventh field 414 in native message format message 400.

It can be seen in the example of FIG. 12 how information can be moved between fields in various positions within the message formats as the information is transferred from native message format message 400 to internal messaging format message 420 to messages 440 and 460. Information of a single field can be split into separate fields, such as the patient name field 402 being split into fields 422 and 444, and information from multiple fields can be concatenated or otherwise combined as in the date fields 434, 436, and 438 being combined into the month-day-year string of field 442 and the year-month-day string of field 466.

In certain embodiments, the formatting of the fields changes between messages. For example, in certain embodiments, the date-year field 412 is formatted as a 8-character ASCII string to record the year, whereas the date-year field 434 is formatted as a 16-bit binary number to record the same information as field 412. The structure of the messages and the fields of each message may be any of the data structures and data formats known to those of skill in the art.

Figure 13:
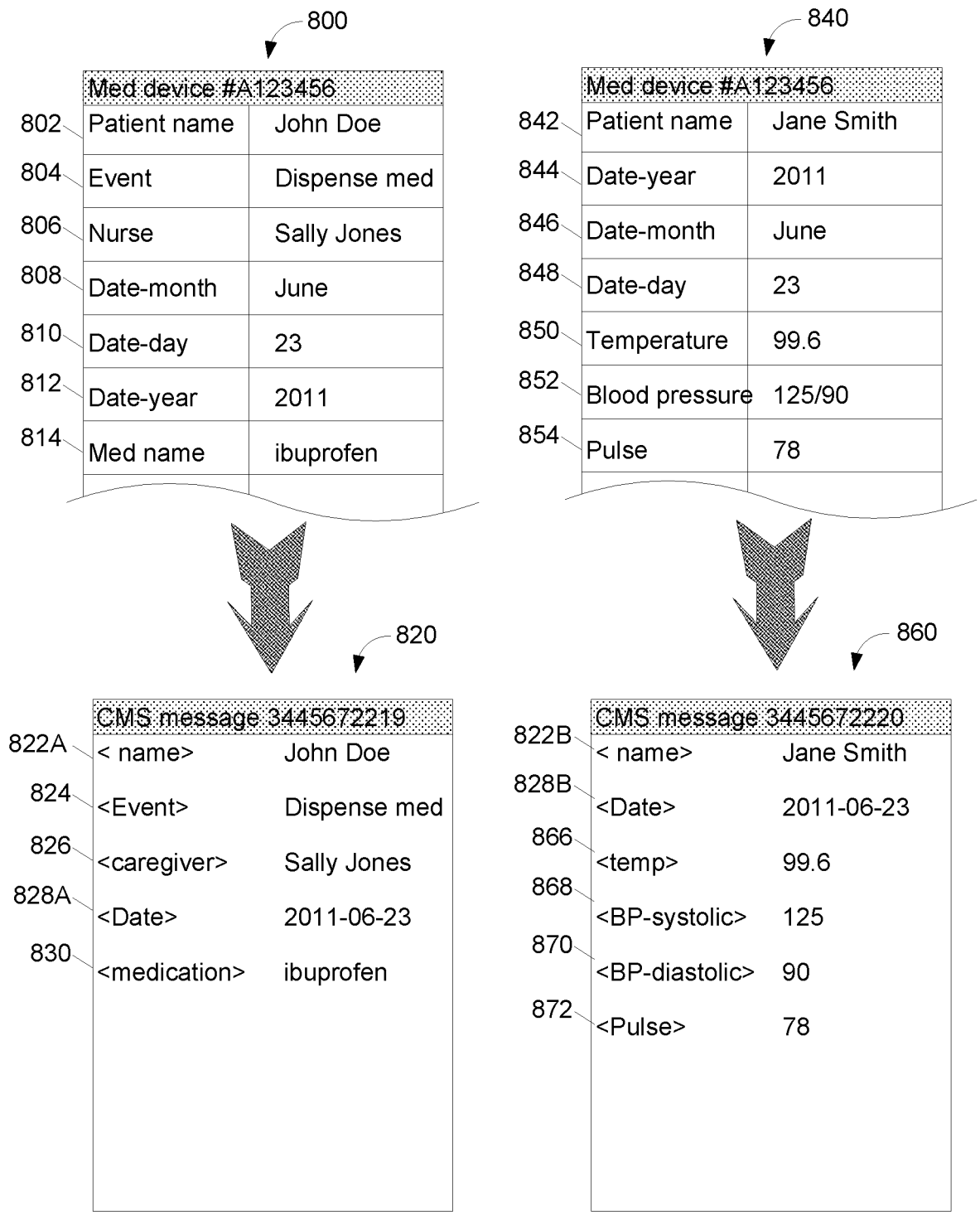
FIG. 13 illustrates the conversion of two example inbound messages in a first and second native message format into a tagged name-data format internal messaging format message according to certain aspects of the present disclosure.

FIG. 13 illustrates the conversion of two example inbound messages 800 and 840 in a first and second native message format into tagged name-data format internal messaging format messages 820 and 860 according to certain aspects of the present disclosure. Each message in the internal messaging format comprises only actively used fields, wherein each field comprises a name, or tag, portion and a data portion. Internal messaging format messages, such as messages 820 and 860, will not have the same set of field but fields having the same name are equivalent. Fields in the incoming message may be mapped into one or more internal messaging format fields, depending on the field.

In this example, the name field 802 and 842 are both mapped to a name field 822, wherein the name field of message 820 is designated 822A and the name field of message 860 is designated 822B to indicate they have different data. Other fields 804, 806, and 814 of message 800 are mapped to fields 824, 826, and 830 of message 820 but these fields 824, 826, and 830 are not found in message 860 as message 840 did not include those data. The date fields 808, 810, and 812 of message 800 and date fields 844, 846, and 848 of message 840 are both mapped to date field 828, again with suffixes 'A' and '13' to indicate the difference in data.

In certain embodiments, data in fields that are not recognized by the mapping module of the adapter 320 are stored in generic data fields, i.e. stored in a field having a system-generated label that is not related to the data. In this manner, data in the incoming message is not lost and may be processed at a later stage in the process or may be archived and available for off-line processing in the future after a modification is made to the adapter 320.

In summary, the CCS 300 provides a modular, extendible, and scalable communication system that can exchange information between any information systems or networked devices. Information from a single sending device or system can be selectively broadcast to predetermined destination devices and systems rather than broadcast to every device on the network. Information may be filtered and processed at one or more selectable points in the communication flow between systems. In certain embodiments, incoming messages are received in their native message format and protocol and converted to an internal messaging format for internal handling in the CCS 300, then converted to the native message format of a receiving system and sent to that system per its native protocol.

FIGS. 14-22 illustrate exemplary graphical user interfaces, or graphical displays, for presenting a user with a graphical representation of the topology of an exemplary CCS 300, and for providing for control and modification thereof. The graphical user interfaces illustrated in FIGS. 14-22 may allow a user, such as an administrator, to efficiently monitor and control message routing between the adapters 320 of the CCS 300 such that a user can quickly identify and handle any problems within the CCS 300 in a timely fashion. For example, the graphical user interfaces may allow a user to interact with a graphical representation of the topology of the CCS 300 in order to configure and test the routing of messages between the adapters 320. For example, the graphical user interfaces may allow a user to inject messages, such as test messages, internal messages or external messages, into the message routing of the CCS 300, such as at the plug-in points of the CCS 300.

In addition, the graphical user interfaces illustrated in FIGS. 14-22 may allow a user to view the status of, add, remove, and modify, the interceptors and CPMs applied at the plug-in points of the CCS 300, such as at pre-InQueue, post InQueue, post StdOutQueue, and post OutQueue plug-in points. In this manner, a user may efficiently add, remove, and monitor interceptors 370a and CPMs 370b that are applied at each of the plug-in points of the CCS 300.

The graphical user interfaces illustrated in FIGS. 14-22 may also allow a user to monitor, add, remove, and configure the adapters 320 in the CCS 300. For example, the graphical user interfaces may present a user with graphical elements that are indicative of the status of the adapters 320, and may allow a user to start, pause, or stop the adapters 320, such as by selecting the graphical elements that are indicative of the status of the adapters 320. In addition, the graphical user interfaces may allow a user to modify various parameters associated with the adapters 320, for example when an adapter 320 associated with an external system is added to the CCS 300, or when a change occurs in a characteristic or aspect of an external system associated with one of the adapters 320.

In one embodiment, the CCS 300 may determine the topology of the CCS 300 based on message routing information corresponding to the adapters 320 of the CCS 300. For example, the CCS 300 may process each message sent from each of the adapters 320 in order to identify the destination of each message. The CCS 300 may determine and store message routing information for each distinct destination of messages sent from each of the adapters 320. The CCS 300 may then individually process, control, and monitor the message routing information for each distinct destination of each of the adapters 320.

Alternatively, or in addition, the CCS 300 may determine the topology of the CCS 300 based on connections between the adapters 320 of the CCS 300. For example, the CCS 300 may monitor and store all active connections between the adapters 320, such as by storing connection information in a database table. The CCS 300 may process the connection information stored in the database table to determine each possible distinct destination of messages sent from each of the adapters 320. The CCS 300 may then individually process, control, and monitor the connection information and the message routing information for each distinct destination of each of the adapters 320. Accordingly, the message routing information may refer to any connection between one or more adapters 320 through which messages may be routed.

In general, the graphical user interfaces of FIGS. 14-22 present the user with high-level information and low-level information corresponding to the topology of the CCS 300, and provide for control and modification thereof. In this manner, the graphical user interfaces of FIGS. 14-22 may allow a user to efficiently monitor, modify, and control the CCS 300, regardless of the complexity and scale of the CCS 300 implementation.

Figure 14:
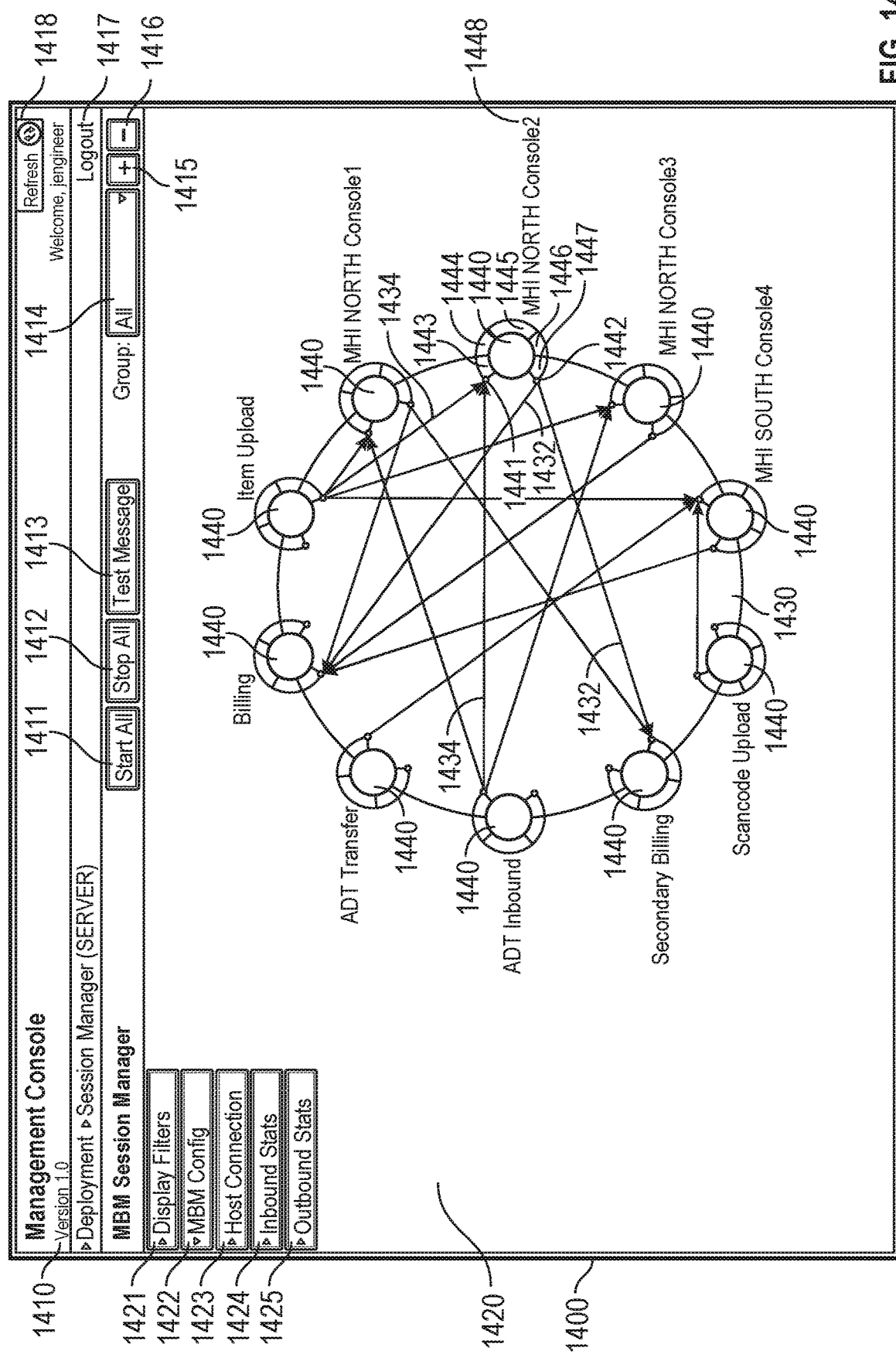
FIG. 14 is an illustration of an exemplary graphical user interface that presents a graphical representation of a topology of a CCS, and that provides for control and modification thereof, according to certain aspects of the present disclosure.

FIG. 14 is an illustration of an exemplary graphical user interface 1400 that presents a graphical representation of a topology of a CCS, and that provides for control and modification thereof, according to certain aspects of the present disclosure.

The graphical user interface 1400 may include an action area 1410 and a display area 1420. The action area 1410 may include a start all selector 1411, a stop all selector 1412, a message selector 1413, a group selector 1414, an add group selector 1415, a remove group selector 1416, a logout selector 1417, and a refresh selector 1418. The display area 1420 may include a filter information selector 1421, an adapter configuration selector 1422, a host connection information selector 1423, an inbound messages information selector 1424, an outbound messages information selector 1425, and a CCS topology display area 1430.

The CCS topology display area 1430 may include adapter icons 1440, outbound message routing 1432, and inbound message routing 1434. The adapter icons 1440 may each include an inbound message node 1441, an outbound message node 1442, a post StdOutQueue segment 1443 that may correspond to a post StdOutQueue plug-in point 378, a post OutQueue segment 1444 that may correspond to a post OutQueue plug-in point 380, a host connection segment 1445, a pre-InQueue segment 1446 that may correspond to a pre-InQueue plug-in point 372, and a post InQueue segment 1447 that may correspond to a post InQueue plug-in point 374. In addition, each adapter icon 1440 may be identified by an adapter label 1448 that may display a name, or other identifier, corresponding to the adapter icon 1440.

In operation, the topology display area 1430 may present a user with a graphical representation of the topology of a corresponding CCS 300. For example, the topology display area 1430 may present graphical representations of each of the adapters 320 of the CCS 300 (as represented by the adapter icons 1440), and of the outbound message routing 1432 and the inbound message routing 1434 of each of the adapters 320. Alternatively, or in addition, the outbound message routing 1432 and the inbound message routing 1434 of each of the adapters 320 may represent connections between the adapters 320.

The color of the adapter icons 1440 may be indicative of the status of the corresponding adapters 320. For example, an adapter icon 1440 having a color of green may indicate that the status of the corresponding adapter 320 is started, an adapter icon 1440 having a color of red may indicate that the status of the corresponding adapter 320 is stopped, and an adapter icon 1440 having a color of grey may indicate that the status of the corresponding adapter 320 is unknown. In one embodiment, in response to a user selecting an adapter icon 1440, the CCS 300 may cycle the status of the corresponding adapter 320 from started to stopped, or from stopped to started, such as by starting or stopping the corresponding adapter 320.

The adapter icons 1440 may also display additional information regarding each corresponding adapter 320. For example, when a user selects, or hovers a pointing device over, one of the segments 1443, 1444, 1445, 1446, 1447 of one of the adapter icons 1440, the graphical user interface 1400 may display additional information to the user, such as in the form of a tool tip, in the form of a pop-up window, in the form of an audio prompt, or generally in any form of presenting information to the user. Alternatively, or in addition, the color of one of the segments 1443, 1444, 1445, 1446, 1447 may change when a user selects, or hovers a pointing device over, the one of the segments 1443, 1444, 1445, 1446, 1447, such as to distinguish a selected segment from the other segments 1443, 1444, 1445, 1446, 1447. For example, the color of a selected segment may change to yellow.

Figure 16:
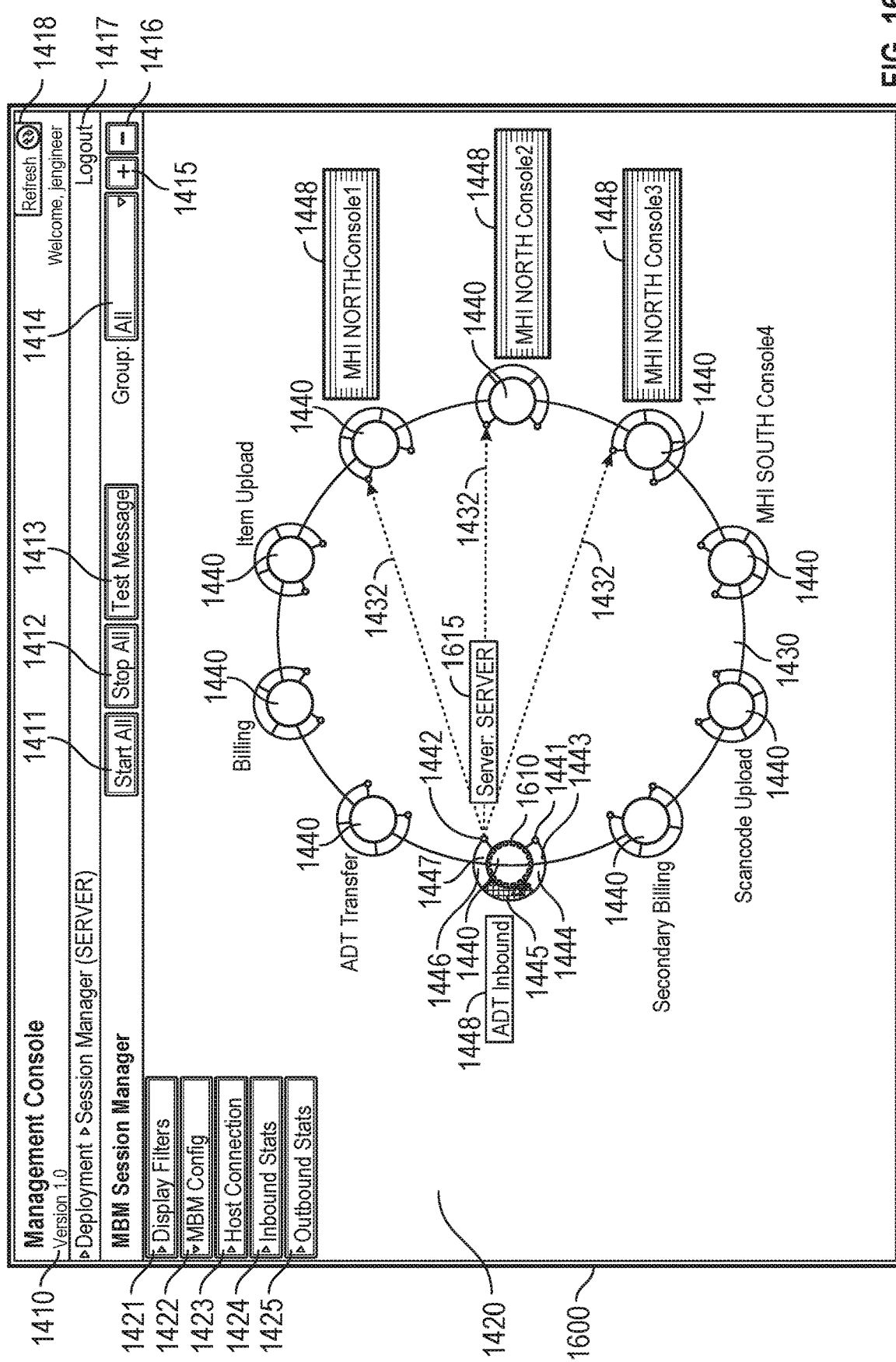
FIG. 16 is an illustration of an exemplary graphical user interface that presents a graphical representation of message routing information associated with a selected adapter of a CCS, and that provides for control and modification thereof, according to certain aspects of the present disclosure.
Figure 17:
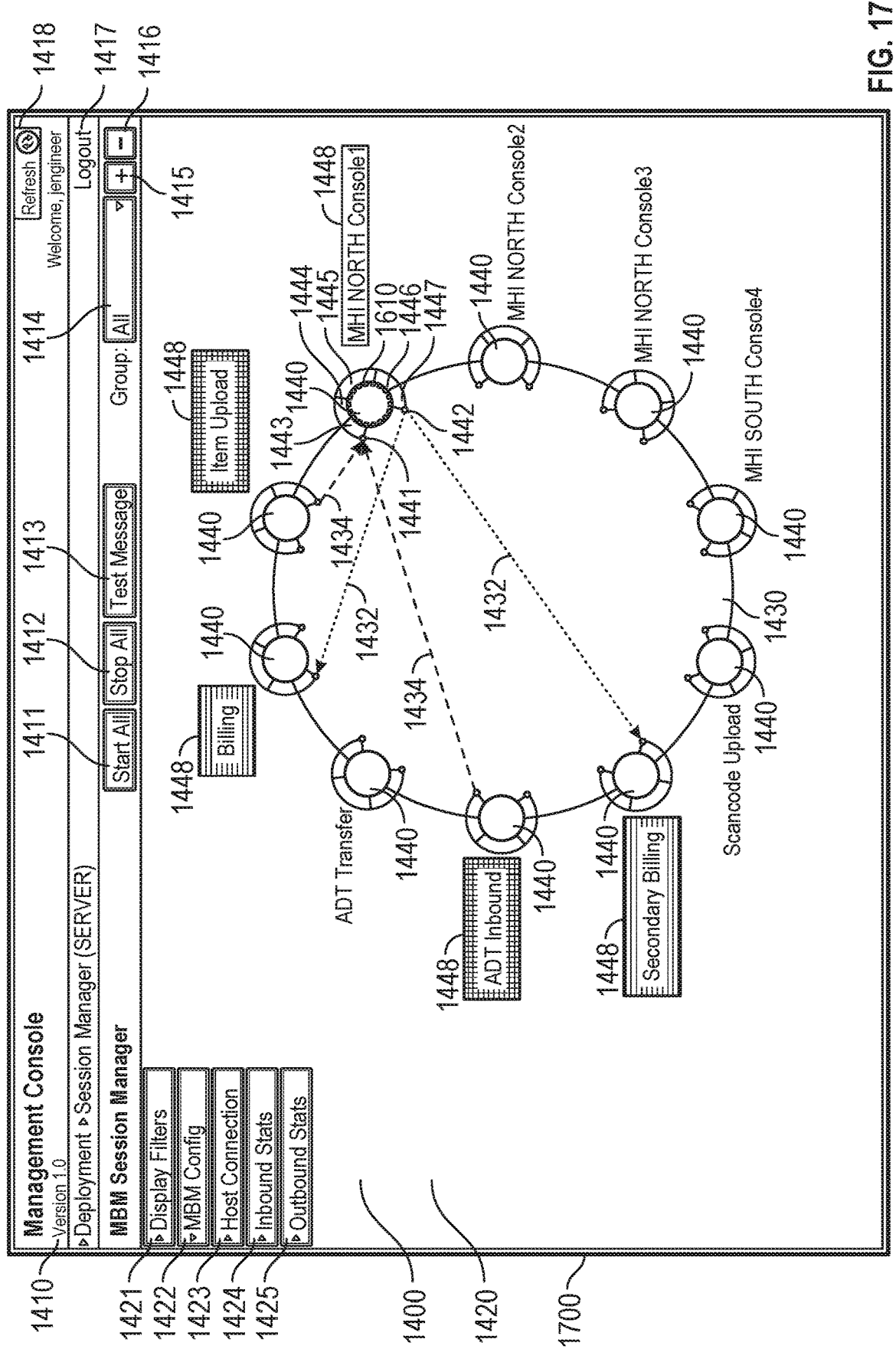
FIG. 17 is an alternative illustration of an exemplary graphical user interface that presents a graphical representation of message routing information associated with a selected adapter of a CCS, and that provides for control and modification thereof, according to certain aspects of the present disclosure.
Figure 18:
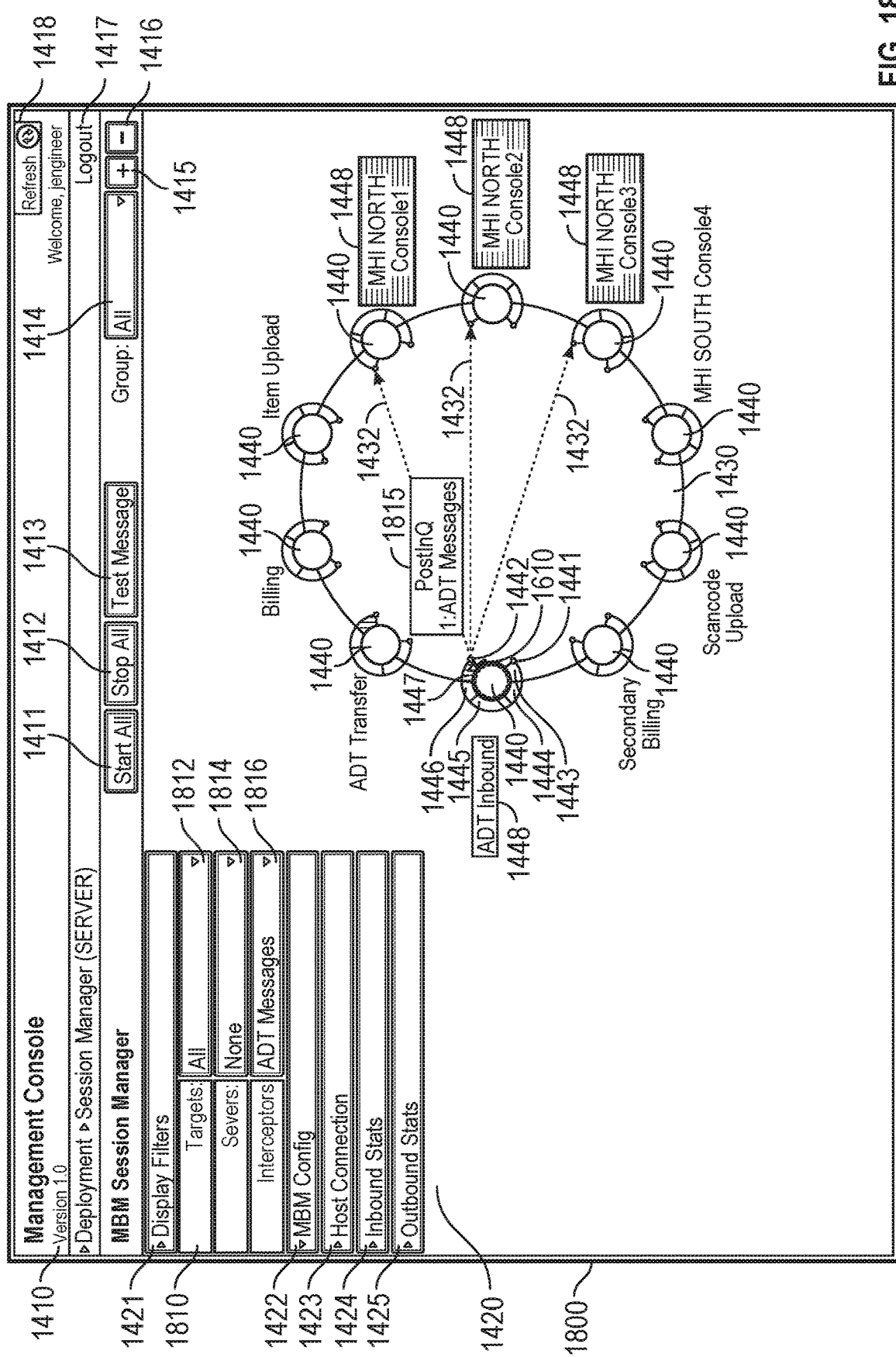
FIG. 18 is an illustration of an exemplary graphical user interface that presents filtering information associated with message routing of a selected CCS, and that provides for control and modification thereof, according to certain aspects of the present disclosure.
Figure 19:
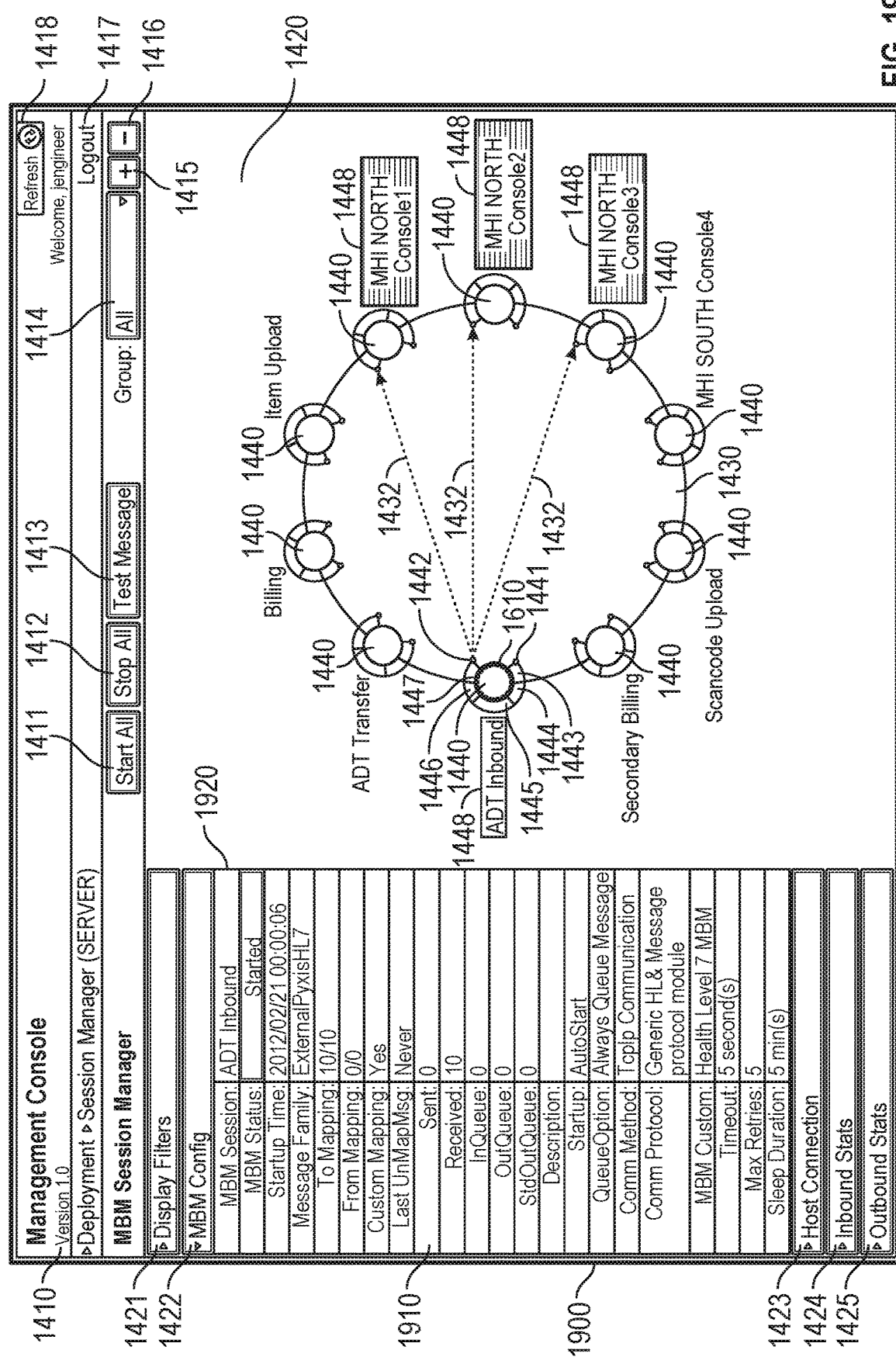
FIG. 19 is an illustration of an exemplary graphical user interface that presents information associated with a selected adapter of a CCS, and that provides for control and modification thereof, according to certain aspects of the present disclosure.
Figure 21:
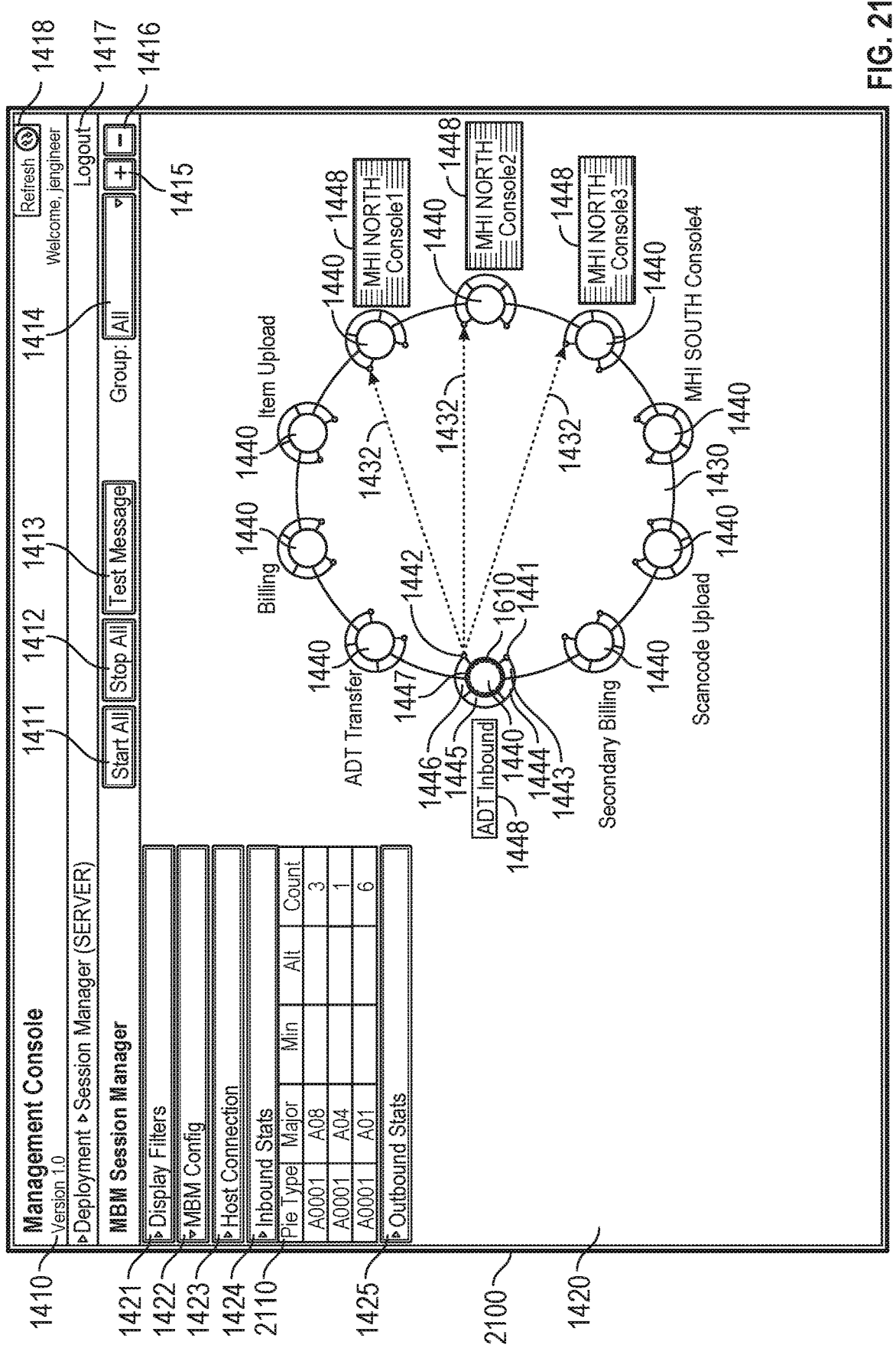
FIG. 21 is an illustration of an exemplary graphical user interface that presents inbound messaging information associated with a selected adapter of a CCS, and that provides for control and modification thereof, according to certain aspects of the present disclosure.
Figure 22:
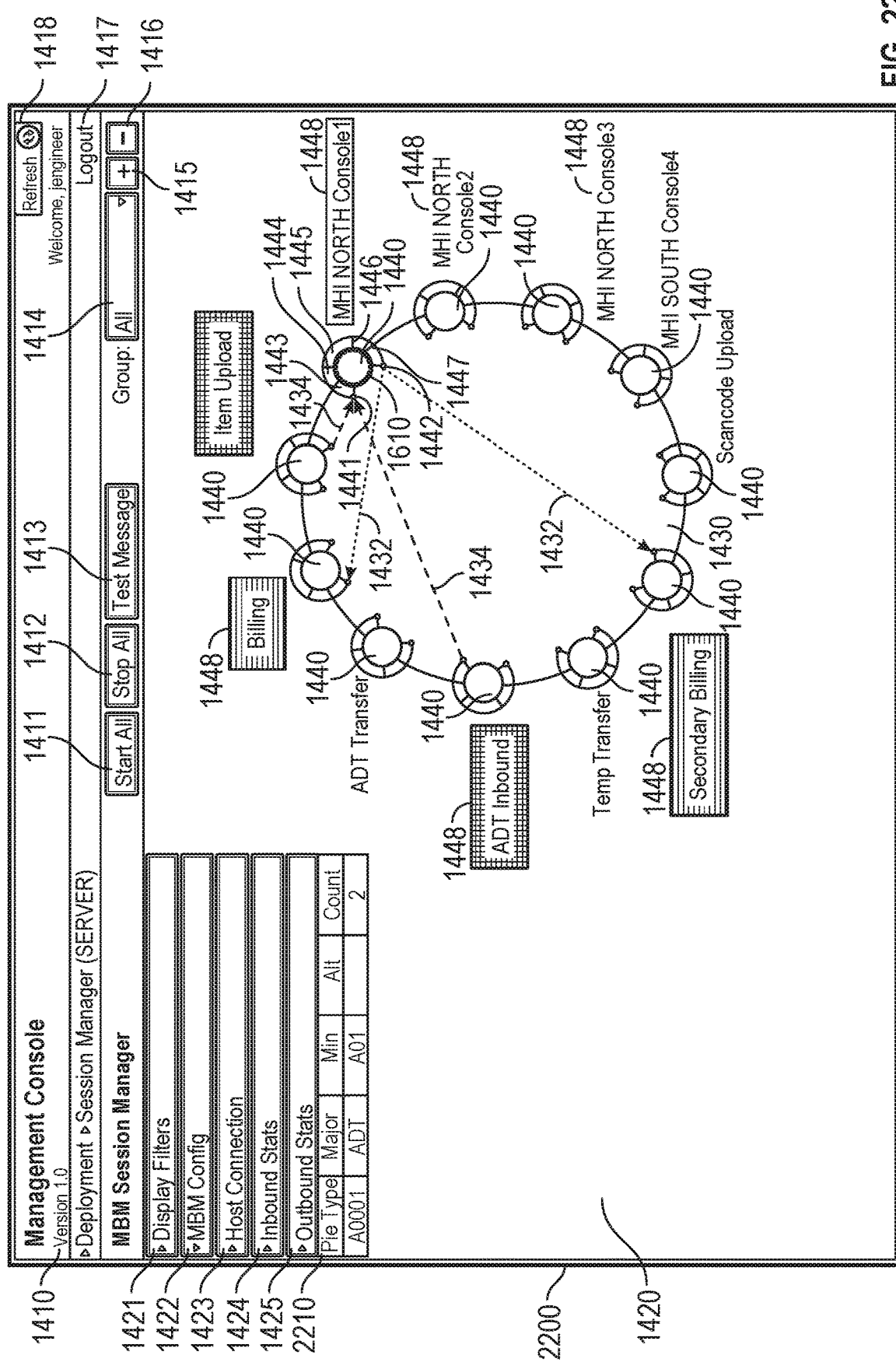
FIG. 22 is an illustration of an exemplary graphical user interface that presents outbound messaging information associated with a selected adapter of a CCS, and that provides for control and modification thereof, according to certain aspects of the present disclosure.

Since the message routing of the CCS 300 may be complex, the graphical user interface 1400 provides several mechanisms for refining, or filtering, the information displayed in the display area 1420. For example, in response to a user selecting one of the adapter icons 1440, the graphical user interface 1400 may display only the message routing of the adapter 320 corresponding to the selected adapter icon 1440, as shown in FIGS. 16 and 17 below. In addition, in response to a user selecting the filter information selector 1421, the graphical user interface may display additional filters, as shown in FIG. 18 below. Similarly, in response to a user selecting the adapter configuration selector 1422, the graphical user interface may display information and controls for the configuration of an adapter 320 corresponding to a selected adapter icon 1440, as shown in FIG. 19 below. In response to a user selecting the host connection information selector 1423, the graphical user interface may display information and controls for a device communicating with, or hosting, an adapter 320 corresponding to a selected adapter icon 1440, as shown in FIG. 21 below. In response to a user selecting the inbound messages information selector 1424, the graphical user interface 1400 may display information and controls for the inbound messages of an adapter 320 corresponding to a selected adapter icon 1440, as shown in FIG. 22 below. In response to a user selecting the outbound messages information selector 1425, the graphical user interface 1400 may display information and controls for the outbound messages of an adapter 320 corresponding to a selected adapter icon 1440, as discussed in FIG. 23 below.

The action area 1410 may provide selectors for performing actions related to the information displayed in the display area 1420, such as actions related to the adapters 320 represented by the adapter icons 1440 displayed in the display area 1420. For example, in response to a user selecting the start all selector 1411 or the stop all selector 1412, the CCS 300 may issue a start command or a stop command, respectively, to each of the adapters represented by an adapter icon 1440 in the display area 1420. In response to the user selecting the message selector 1413, a message, such as a test message or other message, may be injected into the message routing of the CCS 300. Alternatively, or in addition, in response to the user selecting the message selector 1413, the graphical user interface 1400 may display an additional selector that allows the user to identify where a message, such as a test message or other message, should be injected into the CCS 300. Alternatively, or in addition, a user may select a graphical representation in the display area 1420, such as an adapter icon 1440, or a segment corresponding to a plug-in point, to identify where a message, such as a test message or other message, should be injected into the CCS 300.

A user may be able to select a group of adapters 320 using the group selector 1414. In response to the user selecting a group of adapters 320 with the group selector 1414, the adapter icons 1440 may be filtered such that only adapter icons 1440 corresponding to adapters 320 of the selected group are displayed in the display area 1420. In response to the user selecting the add group selector 1415, the graphical user interface 1400 may display a mechanism for adding or creating a group of adapters 320, such as in the form of a pop-up window. In response to a user selecting the remove group selector 1416, any group presently selected by the group selector 1414 will be removed from the group selector 1414. Alternatively, or in addition, in response to a user selecting a group with the remove group selector 1416, the adapter icons 1440 corresponding to the adapters 320 of the selected group may be removed from the display area 1420. In response to a user selecting the refresh selector 1418, the graphical user interface 1400 may be refreshed. In response to a user selecting the logout selector 1417, the user may be logged out of the graphical user interface 1400.

Figure 15:
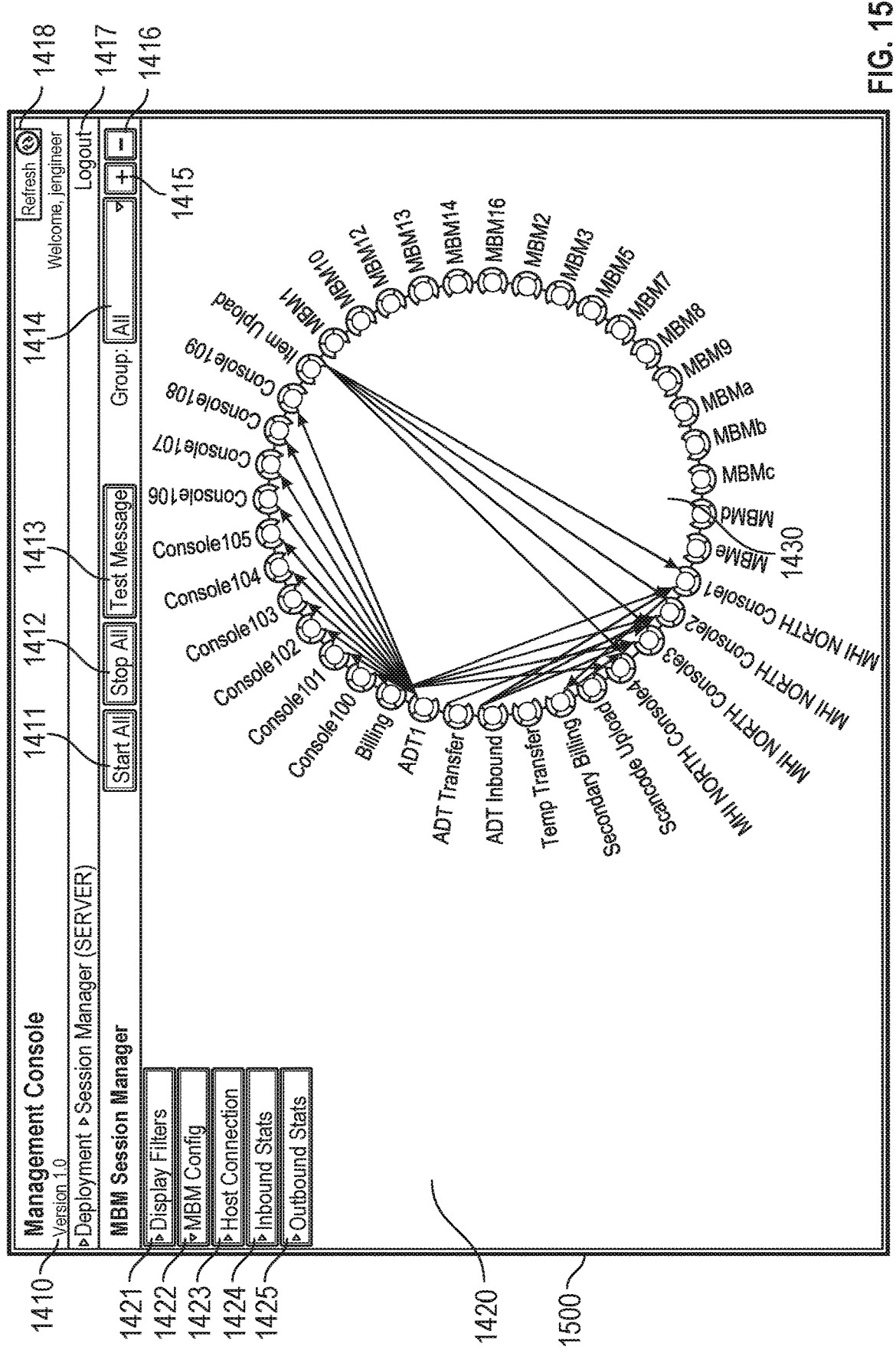
FIG. 15 is an illustration of an exemplary graphical user interface that presents a graphical representation of a topology of a scaled implementation of a CCS, and that provides for control and modification thereof, according to certain aspects of the present disclosure.

FIG. 15 is an illustration of an exemplary graphical user interface 1500 that presents a graphical representation of a topology of a scaled implementation of a CCS, and that provides for control and modification thereof, according to certain aspects of the present disclosure. The graphical user interface 1500 may present the topology of a CCS 300 that includes a large number of adapters 320 in a readable format.

For example, the graphical user interface 1400 of FIG. 14 may be transformed into the graphical user interface 1500 of FIG. 15 when the number of the adapter icons 1440 displayed in the display area 1420 exceeds a threshold. The size of the adapter icons 1440 may change proportionally to the number of adapter icons 1440 displayed in the display area 1410. In addition, when the number of displayed adapter icons 1440 exceeds a threshold, the adapter labels 1448 of the adapter icons 1440 may rotate proportionally to the number of displayed adapter icons 1440 such that the adapter labels 1448 of the adapter icons 1440 do not overlap. In this manner, the graphical user interface 1500 presents the user with the topology of a CCS 300 that includes a large number of adapters 320 in a readable format.

FIG. 16 is an illustration of an exemplary graphical user interface 1600 that presents a graphical representation of message routing information associated with a selected adapter of a CCS, and that provides for control and modification thereof, according to certain aspects of the present disclosure. The graphical user interface 1600 may be presented in response to a user selecting one of the adapter icons 1440 of FIG. 15. For example, the graphical user interface 1600 may be displayed in response to a user selecting the adapter icon 1440 having adapter label 1448 entitled "ADT Inbound." The graphical user interface 1600 may present an indicator 1610 around the circumference of a selected adapter icon 1440, such as to distinguish the selected adapter icon 1440 from the other adapter icons 1440. In addition, the adapter label 1448 of the selected adapter icon 1440 may be modified to distinguish the adapter label 1448 of a selected adapter icon 1440 from the adapter labels 1448 of the other adapter icons 1440, such as by drawing an outline around the adapter label 1448 of the selected adapter icon 1440.

As shown in the graphical user interface 1600, in response to a user selecting one of the adapter icons 1440, the outbound message routing 1432 and inbound message routing 1434 presented in the display area 1420 may be filtered to only present the outbound message routing 1432 and inbound message routing 1434 of the adapter 320 represented by the selected adapter icon 1440. Further in this regard, in order to distinguish the adapters 320 that receive messages from, or send messages to, the adapter 320 represented by the selected adapter icon 1440, the adapter labels 1448 may be highlighted for the adapter icons 1440 corresponding to the adapters 320 that receive messages from, or send messages to, the adapter 320 represented by the selected adapter icon 1440.

The graphical user interface 1600 also illustrates a host connection tool tip 1615 that is presented to the user, for example, in response to the user selecting, or hovering a pointing device over, the host connection segment 1445. Similarly, the graphical user interface 1600 may display a tool tip corresponding to one of the other segments 1443, 1444, 1446, 1447, when a user selects, or hovers a pointing device over, one of the other segments 1443, 1444, 1446, 1447. In addition, the color of the selected host connection segment 1445 may change, such as to yellow, in order to visually distinguish the selected host connection segment 1445 from the other segments 1443, 1444, 1446, 1447.

FIG. 17 is an alternative illustration of an exemplary graphical user interface 1700 that presents a graphical representation of message routing information associated with a selected adapter of a CCS, and that provides for control and modification thereof, according to certain aspects of the present disclosure. In addition to the information illustrated in FIG. 16, FIG. 17 further illustrates that the outbound message routing 1432 and inbound message routing 1434 corresponding to an adapter 320 represented by a selected adapter icon 1440 may be individually color-coded, such as to allow a user to easily distinguish between the outbound message routing 1432 and the inbound message routing 1434. For example, the inbound message routing 1434 may be represented by a first color, while the outbound message routing 1432 may be represented by a second color that is visually distinguishable from the first color.

In addition, graphical user interface 1700 illustrates that the highlighting of the adapter labels 1448 of the adapter icons 1440 corresponding to adapters 320 that send messages to, or receive messages from, the adapter 320 corresponding to the selected adapter icon 1440 may also be color-coded. For example, the adapter labels 1448 of the adapter icons 1440 corresponding to adapters 320 that send messages to the adapter 320 corresponding to the selected adapter icon 1440 may be highlighted in the same color as the inbound message routing 1434, while the adapter labels 1448 of the adapter icons 1440 corresponding to the adapters 320 that receive message from the adapter 320 corresponding to the selected adapter icon 1440 may be highlighted in the same color as the outbound message routing 1432.

FIG. 18 is an illustration of an exemplary graphical user interface 1800 that presents filtering information associated with message routing of a selected CCS, and that provides for control and modification thereof, according to certain aspects of the present disclosure. The graphical user interface 1800 may be displayed in response to a user selecting the filter information selector 1421, such as in FIG. 14. In addition to the elements discussed in regards to FIGS. 14-17, the graphical user interface 1800 may also include a filter selector area 1810. The filter selector area 1810 may include a target selector 1812, a server selector 1814, and an interceptor selector 1816.

In response to a user selecting one or more values from one or more of the target selector 1812, the server selector 1814, or the interceptor selector 1816, the graphical user interface 1800 may modify the display of the adapter icons 1440, the segments 1443, 1444, 1445, 1446, 1447, or any of the graphical elements associated therewith, to visually distinguish the components that satisfy the values selected by the target selector 1812, the server selector 1814, or the interceptor selector 1816. For example, in the graphical user interface 1800, a user selected the value "ADT Messages" in the interceptor selector 1816, and in response thereto, the color of each segment of each of the adapters 320 that corresponds to a plug-in point where the "ADT Messages" interceptor is being applied is modified such that the segments where the selected interceptor is being applied are visually distinguishable from the other segments. For example, the color of the segments may be changed to red.

The graphical user interface 1800 also illustrates a post InQueue tooltip 1815 that is displayed to the user in response to the user selecting, or hovering a pointing device over, the post InQueue segment 1447. Similarly, the graphical user interface 1800 may display a tool tip corresponding to one of the other segments 1443, 1444, 1445, 1446, when a user selects, or hovers a pointing device over, one of the other segments 1443, 1444, 1445, 1446.

FIG. 19 is an illustration of an exemplary graphical user interface 1900 that presents information associated with a selected adapter of a CCS, and that provides for control and modification thereof, according to certain aspects of the present disclosure. The graphical user interface 1900 may be displayed in response to a user selecting the adapter configuration selector 1422, such as in FIG. 14. In addition to the elements discussed in regards to FIGS. 14-17, the graphical user interface 1900 may also include an adapter information area 1910 and an adapter status selector 1920.

The adapter information area 1910 may display information and controls related to the adapter 320 corresponding to the selected adapter icon 1440. For example, the adapter information area 1910 may display the status of the adapter 320, message statistics for the adapter 320, mappings for the adapter 320, or generally any information corresponding to the adapter 320. In addition, the user may modify the status of the adapter 320 corresponding to the selected adapter icon 1440 by selecting the adapter status selector 1920. For example, if the status of the adapter 320 is started, the CCS 300 may change the status of the adapter 320 to stopped, in response to a user selecting the adapter status selector 1920, and vice-versa.

Figure 20:
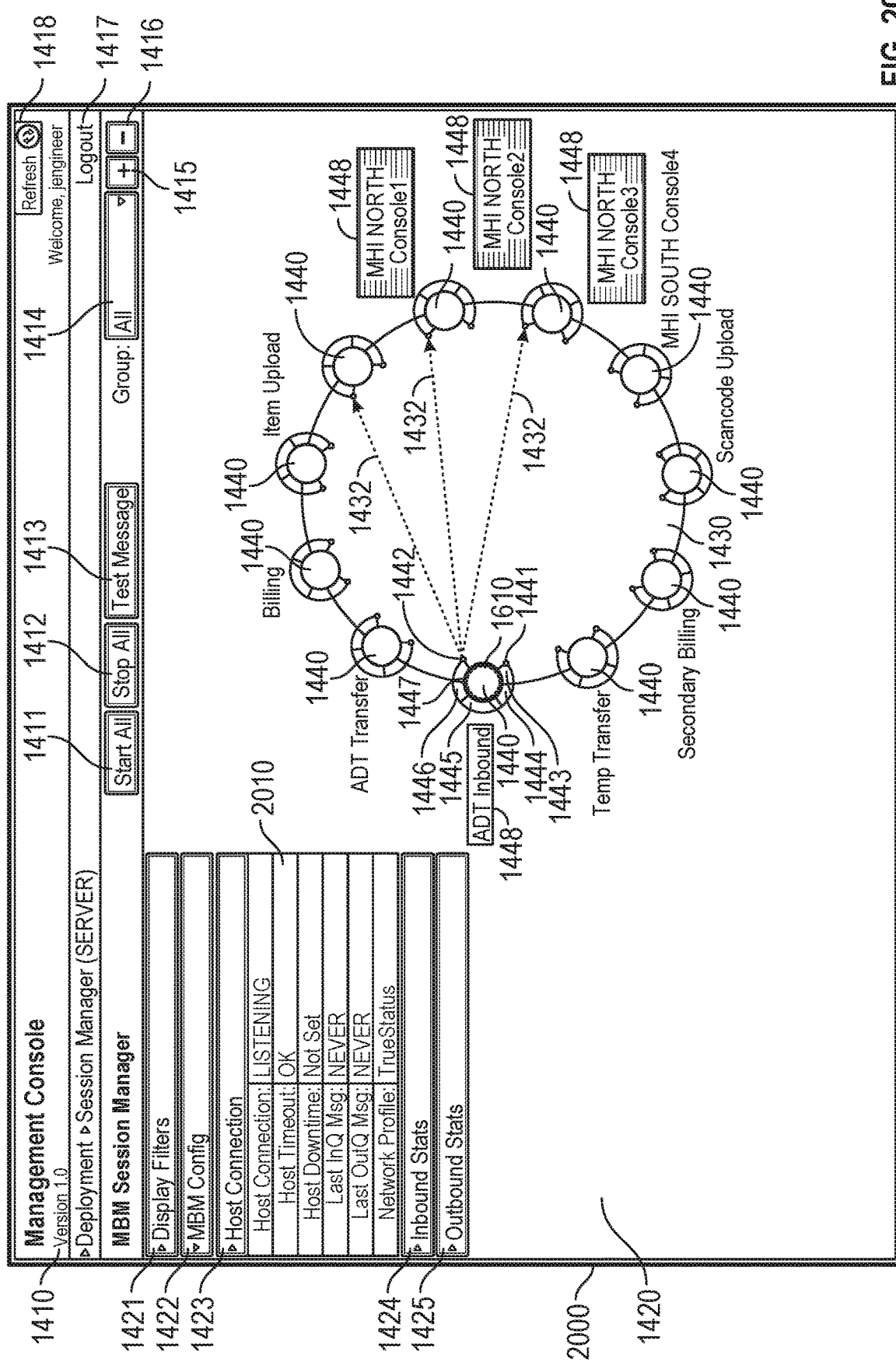
FIG. 20 is an illustration of an exemplary graphical user interface that presents information associated with a device communicating with a selected adapter of a CCS, and that provides for control and modification thereof, according to certain aspects of the present disclosure.

FIG. 20 is an illustration of an exemplary graphical user interface 2000 that presents information associated with a device communicating with a selected adapter of a CCS, and that provides for control and modification thereof, according to certain aspects of the present disclosure. The graphical user interface 2000 may be displayed in response to a user selecting the host connection information selector 1423, such as in FIG. 14. In addition to the elements discussed in regards to FIGS. 14-17, the graphical user interface 2000 may include a host connection display area 2010. The host connection display area 2010 may display information and controls related to the device that is communicating with, or hosting, the adapter 320 corresponding to the selected adapter icon 1440. For example, the host connection display area 2010 may display downtime information, connection status information, timeout information, or generally any information related to the device communicating with, or hosting, the adapter 320 corresponding to the selected adapter icon 1440.

FIG. 21 is an illustration of an exemplary graphical user interface 2100 that presents inbound messaging information associated with a selected adapter of a CCS, and that provides for control and modification thereof, according to certain aspects of the present disclosure. The graphical user interface 2100 may be displayed in response to a user selecting the inbound messages information selector 1424, such as in FIG. 14. In addition to the elements discussed in regards to FIGS. 14-17, the graphical user interface 2100 may include an inbound messages information area 2110. The inbound messages information area 2110 may display information and controls related to the inbound messages of the adapter 320 corresponding to the selected adapter icon 1440. For example, the inbound messages information area 2110 may display message counts for each of the inbound message sources for the adapter 320 corresponding to the selected adapter icon 1440.

FIG. 22 is an illustration of an exemplary graphical user interface 2200 that presents outbound messaging information associated with a selected adapter of a CCS, and that provides for control and modification thereof, according to certain aspects of the present disclosure. The graphical user interface 2200 may be displayed in response to a user selecting the outbound messages information selector 1425, such as in FIG. 14. In addition to the elements discussed in regards to FIGS. 14-17, the graphical user interface 2200 may include an outbound messages information area 2210. The outbound messages information area 2210 may display information and controls related to the outbound messages of the adapter 320 corresponding to the selected adapter icon 1440. For example, the outbound messages information area 2210 may display message counts for each of the outbound message destinations for the adapter 320 corresponding to the selected adapter icon 1440.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

A computer system further includes a data storage device such as a magnetic disk or optical disk, coupled to a bus for storing information and instructions. Computer systems may be coupled via input/output modules to various devices. The input/output module can be any input/output module, such as USB ports. The input/output module is configured to connect to a communications module, such as networking interface cards, as Ethernet cards, and modems. In certain aspects, the computer system includes an input/output module such as a keyboard and a pointing device, e.g., a mouse or a trackball, by which a user can provide input to the computer system. Other kinds of input devices can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Exemplary output devices include display devices, such as a CRT (cathode ray tube) or LCD (liquid crystal display) monitor, for displaying information to the user.

According to one aspect of the present disclosure, the disclosed processes can be implemented using a processor executing one or more sequences of one or more instructions contained in memory. Such instructions may be read into memory from another machine-readable medium, such as a magnetic disk or an optical disk. Execution of the sequences of instructions contained in main memory causes processor to perform the process steps described herein. One or more processors in a multi-processing arrangement may also be employed to execute the sequences of instructions contained in memory. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

A computing system can include clients and servers. A client and server are generally remote from each other and typically interact through a communication network. The relationship of client and server arises by virtue of computer programs running on the respective computers and having a client-server relationship to each other. Computing systems can be, for example, and without limitation, a desktop computer, laptop computer, or tablet computer. Computing systems can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions to a processor for execution. Such a medium may take many forms, including, but not limited to, non-volatile media, volatile media, and transmission media. Non-volatile media include, for example, optical or magnetic disks. Volatile media include dynamic memory. Transmission media include coaxial cables, copper wire, and fiber optics. Common forms of machine-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

While operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A method of interfacing a plurality of adapter interfaces for medical systems using a centralized communication system, the method comprising the steps of:
   receiving from a first adapter interface of a plurality of adapter interfaces, an external message in a first native message format of the first medical device, the first adapter interface being communicatively coupled to the first medical device and configured to receive and transmit messages to and from the first medical device;
   filtering the external message to leave out a portion of external message;
   mapping the portion of the external message into a first internal message in an internal messaging format having a different field structure than the first native message format;
   mapping at least a portion of the first internal message into a second message in a second native message format of a second medical device;
   providing the second message to a second adapter interface of the plurality of adapter interfaces, the second adapter interface being communicatively coupled to the second medical device;
   store information pertaining to message routing of internal messages transmitted between the plurality of interface adapter interfaces;
   determine a communication topology of the centralized communication system based on the message routing of internal messages transmitted between the plurality of adapter interfaces; and
   providing for display a graphical representation of the determined communication topology associated with the plurality of adapter interfaces, including a graphical representation of a communication path between the first medical device and the adapter interface associated with the second medical device based on providing the second message to the adapter interface, wherein the graphical representation is configure to enable a user to select a graphical icon corresponding to a respective interface of the plurality of adapter interfaces;
   receiving a first user selection of the graphical icon corresponding to the first adapter interface and an indication to modify the selected adapter interface within the communication topology to display routing information; and,
   in response to the first user selection, presenting for display message routing information for the first adapter interface.

2. The method of claim 1, wherein mapping the portion of the external message comprises splitting a single field of the first native message format into separate fields and concatenating multiple fields of the first native message format into a second single field.

3. The method of claim 1, further comprising:
   receiving a second user selection of a graphical element corresponding to the first adapter and an indication to modify the first adapter interface within the communication topology; and
   modifying, responsive to receiving the second user selection, a location of the first adapter interface within the topology.

4. The method of claim 1, further comprising:
   receiving a second user selection of a location in the graphical representation of the communication topology and an indication to inject a message at the location; and
   injecting, responsive to receiving the second user selection, the message into a message flow path associated with the location.

5. The method of claim 1, further comprising:
   receiving a second user selection of a graphical element corresponding to the first adapter interface and an indication to filter the graphical representation of the communication topology to display only message routing information related to messages transmitted to or from the first adapter interface; and
   filtering, responsive to receiving the second user selection, the graphical representation to display only message routing information related to the messages transmitted to or from the first adapter interface.

6. The method of claim 5, further comprising:
graphically displaying messages transmitted to the first adapter interface in a first color and messages transmitted from the first adapter interface in a second color.

7. A system for managing a communication system, the system comprising:
a non-transitory machine-readable memory comprising instructions stored thereon; and
one or more processors configured to execute the instructions to perform operations, comprising:
providing, in a centralized communication system, a plurality of adapter interfaces configured to adapt message communications between a plurality of medical devices and one or more external systems, a respective adapter interface being configured to receive a first message in a first format from a first device, convert a first portion of the first message into second format different than the first format, and send the converted portion in a second message to a second device different than the first device;
monitor internal messages transmitted between the plurality of adapter interfaces in the centralized communication system;
store, in a memory device, based on monitoring the internal messages, routing information associated with active communication connections between the adapter interfaces;
determine a communication topology of the centralized communication system based on the message routing information;
provide a graphical representation of the determined communication topology of the centralized communication system, with each adapter interface being represented in the graphical representation by one or more graphical elements;
receive a first user selection of the graphical icon corresponding to the first adapter interface and an indication to modify the selected adapter interface within the communication topology to display routing information; and
in response to the user selection, present for display message routing information for the first adapter interface.

8. The system of claim 7, wherein the plurality of adapter interfaces are further configured to:
convert the first portion of the first message into second format the second format based on splitting a single field of the first format into separate fields and concatenating multiple fields of the first format into a second single field.

9. The system of claim 7, wherein the communication topology includes a plurality of plug-in points at which transmitted messages are accessible by an interceptor module.

10. The system of claim 7, wherein each graphical element includes a color indicative of a status of a corresponding adapter interface of the plurality of adapter interfaces, wherein the operations further comprise:
receiving a second user selection of a graphical element corresponding to a first adapter interface and an indication to modify a status of the first adapter interface; and
modifying the status of the first adapter interface according to the user selection.

11. The system of claim 7, wherein the operations further comprise:
receiving a second user selection of a graphical element corresponding to a first adapter interface not currently operating within the centralized communication system, and an indication to add the first adapter interface to the centralized communication system; and
modifying, responsive to receiving the second user selection, the communication topology of the centralized communication system by adding the first adapter interface to the plurality of adapter interfaces within the centralized communication system.

12. The system of claim 7, wherein the operations further comprise:
receiving a second user selection of a graphical element corresponding to a first adapter interface and an indication to remove the first adapter interface from the centralized communication system; and
modifying, responsive to receiving the second user selection, the communication topology of the centralized communication system by removing the first adapter interface from the centralized communication system.

13. The system of claim 7, wherein the operations further comprise:
receiving a second user selection of a location in the graphical representation of the determined communication topology and an indication to inject a message into the centralized communication system at the location; and
injecting the message into a message flow path associated with the location.

14. The system of claim 7, wherein the operations further comprise:
receiving a second user selection of a graphical element corresponding to a first adapter interface and an indication to filter the graphical representation of the determined communication topology to display only message routing information related to messages transmitted to or from the first adapter interface; and
filtering, responsive to receiving the user selection, the graphical representation to display only message routing information related to the messages transmitted to or from the first adapter interface.

15. The system of claim 14, wherein the operations further comprise:
graphically displaying messages transmitted to the first adapter interface in a first color and messages transmitted from the first adapter interface in a second color.

16. The system of claim 7, wherein the operations further comprise:
receiving a second user selection of a graphical element corresponding to a first adapter interface and an indication to display configuration information for the first adapter interface; and
providing for display, responsive to receiving the user selection, the configuration information.

17. The system of claim 7, wherein the operations further comprise:
receiving a second user selection of a graphical element corresponding to a first adapter interface and an indication to display host information; and
providing for display, responsive to receiving the second user selection, host information associated with a device communicating with the first adapter interface.

18. The system of claim 7, wherein the operations further comprise:

receiving a second user selection of a graphical element corresponding to a first adapter interface and an indication to display inbound message information associated with the first adapter interface; and provide for display, responsive to receiving the second user selection, information pertaining to messages inbound to the first adapter interface.

19. The system of claim 7, wherein the operations further comprise:

receiving a second user selection of a graphical element corresponding to a first adapter interface and an indication to display outbound message information associated with the first adapter interface; and provide for display, responsive to receiving the second user selection, information pertaining to messages outbound from the first adapter interface.

20. The system of claim 7, wherein the operations further comprise:

determining the message routing information from connections between the plurality of adapter interfaces, irrespective of whether any internal messages have been transmitted over the connections.

21. A non-transitory computer readable medium having instructions stored thereon that, when executed by a computing device, perform a method for managing a communication system, the method comprising:

presenting a graphical representation of a communication topology of a centralized communication system comprising a plurality of adapter interfaces;

identifying a user interaction with the graphical representation of the communication topology of the centralized communication system;

receiving a first user selection of a graphical element corresponding to a first adapter interface and an indication to modify the first adapter interface within the communication topology; and modifying, responsive to receiving the first user selection, a location of the first adapter interface within the communication topology, wherein modifying the location comprises modifying the communication topology of the centralized communication system, wherein centralized communication system is configured to receive messages from respective adapter interfaces of the plurality of adapter interfaces in external messaging formats of medical devices in at least one of a plurality of different types, filter a first portion of a received message to leave out a second portion of the received message, and convert the second portion of the received message to an internal message in an internal messaging format, transmit the internal message to a core, wherein core is configured to transfer the internal message to a different adapter interface based on information provided by a respective interface module, and wherein messages in the internal messaging format have a different field structure than the external messaging formats, the different field structure including having a first single field of a respective external messaging format split into separate fields and having multiple fields of the respective external messaging format concatenated into a second single field, wherein the centralized communication system comprises a plurality of plug-in points at which transmitted messages are accessible by an interceptor module.

22. The non-transitory computer readable medium of claim 21, wherein the method further comprises:

receiving a second user selection of a location in the graphical representation of the communication topology and an indication to inject a message at the location; and injecting, responsive to receiving the second user selection, the message into a message flow path associated with the location.

23. The non-transitory computer readable medium of claim 21, wherein the method further comprises:

receiving a second user selection of a graphical element corresponding to a first adapter interface and an indication to filter the graphical representation of the communication topology to display only message routing information related to messages transmitted to or from the first adapter interface; and filtering, responsive to receiving the second user selection, the graphical representation to display only message routing information related to the messages transmitted to or from the first adapter interface.

24. The non-transitory computer readable medium of claim 23, wherein the method further comprises:

graphically displaying messages transmitted to the first adapter interface in a first color and messages transmitted from the first adapter interface in a second color.

\* \* \* \* \*